US009089606B2

(12) United States Patent
Kurihara et al.

(10) Patent No.: US 9,089,606 B2
(45) Date of Patent: *Jul. 28, 2015

(54) BRAIN-DERIVED NEUROTROPHIC FACTOR OR NEUROTROPHIN-4/5 TO TREAT PERIODONTAL DISEASES AND PULPAL DISEASES

(75) Inventors: Hidemi Kurihara, Hiroshima (JP); Hiroyuki Kawaguchi, Hiroshima (JP); Katsuhiro Takeda, Hiroshima (JP); Hideki Shiba, Hiroshima (JP); Noriyoshi Mizuno, Hiroshima (JP); Hiroshi Yoshino, Hiroshima (JP); Naohiko Hasegawa, Hiroshima (JP); Hiroaki Shinohara, Fukuyama (JP)

(73) Assignees: TWO CELLS CO., LTD., Hiroshima (JP); Hidemi Kurihara, Hiroshima (JP)

( * ) Notice: Subject to any disclaimer, the term of this patent is extended or adjusted under 35 U.S.C. 154(b) by 380 days.

This patent is subject to a terminal disclaimer.

(21) Appl. No.: 13/422,363

(22) Filed: Mar. 16, 2012

(65) Prior Publication Data

US 2012/0214738 A1    Aug. 23, 2012

Related U.S. Application Data

(63) Continuation of application No. 10/571,069, filed as application No. PCT/JP2004/013023 on Sep. 8, 2004, now Pat. No. 8,158,752.

(30) Foreign Application Priority Data

Sep. 9, 2003   (JP) .................. 2003-316719

(51) Int. Cl.
*A61K 38/18*    (2006.01)
*C07K 14/475*   (2006.01)
*A61K 45/06*    (2006.01)

(52) U.S. Cl.
CPC ............... *A61K 45/06* (2013.01); *A61K 38/185* (2013.01); *Y10S 530/812* (2013.01)

(58) Field of Classification Search
None
See application file for complete search history.

(56) References Cited

U.S. PATENT DOCUMENTS 5,372,503 A    12/1994  Elia
5,707,647 A    1/1998   Dunn et al.
5,717,030 A *  2/1998   Dunn et al. .................. 523/111

FOREIGN PATENT DOCUMENTS

WO    WO-96/39202 A1    12/1996

OTHER PUBLICATIONS

The website downloaded Jan. 10, 2014 from biomaterial.co.jp/en/products/teruplug/product.html; 2 pages total.*
The abstract by Harada et al., "Depletion of BDNF Induces Delay of Regeneration of the Periodontal Ruffini Endings"; Society for Neuroscience 2002; abstract #849.4; 1 page total.*

(Continued)

*Primary Examiner* — Christina Borgeest
(74) *Attorney, Agent, or Firm* — Birch, Stewart, Kolasch & Birch, LLP

(57) ABSTRACT

The objects of the present invention are: to provide a therapeutic agent and a therapeutic method for periodontal diseases and pulpal diseases, a transplant for periodontal tissue regeneration, and a method for regenerating the periodontal tissue.

According to the present invention, there are provided therapeutic agents for periodontal diseases and pulpal diseases which comprise neurotrophic factors as an active ingredient.

8 Claims, 43 Drawing Sheets

(A)

GAPDH

HPL cell    Human periodontal ligament (B)

BDNF  TrkB

Human periodontal ligament (C)

BDNF  TrkB

HPL cell

(56) References Cited

OTHER PUBLICATIONS

Kurihara, H. et al., "Neurotrophins in cultured cells from periodontal tissues", Journal of Periodontology, 2003, vol. 74, No. 1, pp. 76-84.
Harada F. et al., "The involvement of brain-derived neurotrophic factor (BDNF) in the regeneration of periodontal Ruffini endings following transaction of the inferior alveolar nerve", Archives of History and Cytology, 2003, vol. 66, No. 3, pp. 183-194.
Tsuboi, Y. et al., "Mitogenic Effects of Neurotrophins on a Periodontal Ligament Cell Line", Journal of Dental Research, 2001, vol. 80, No. 3, pp. 881-886.
Yoshino, H., Recent topics, Regeneration of periodontal tissue and neurotrophin, Journal of Hiroshima University Faculty of Dentistry, 1998, vol. 30, p. 236 (in Japanese).
K. Asaumi et al., Bone vol. 26, No. 6, 2000, pp. 625-633.
Excerpt of Program and Abstracts for Spring Conference (45th), 2002 of Japanese Society of Periodontology, Journal of the Japanese Society of Periodontology, vol. 44, Apr. 2002 (with English translation).
Bu et al., J. Modern Stomatol, vol. 16, No. 1, pp. 21-23 (Jan. 2002).
Nishimura, Hiroshi, et at., "Long-term obersvation of periodontal healing after application of rhBMP-2," Journal of the Japanese Society of Periodontology, 2002, vol. 44-suppl: pp. 118.
Nakane, K. et al., "Periodontal Regeneration Using rhBMP-2 in Middle-aged Beagles", Journal of Japanese Society of Periodontology, 2003, vol. 45 (1), pp. 33-42.
Kato, Hiroshi, "Periodontal Regenerative Therapy Using Bine Morphogenetic Protein (BMP)", Journal of the Japanese Society of Periodontology, 2003, vol. 45(1), pp. 9-21.
Japanese Office Action issued Mar. 25, 2010.
Kirker-Head, Advanced Drug Delivery Reviews, 43:65-92 (2000).
Wikesjo et al., J Periodontal. May 2003; 74: 635-647.
Magloire, et al., Adv Dent Res, (2001), vol. 15, pp. 46-50.
Thoenen, et al., Nature Neuroscience, (2002), vol. 5(suppl), pp. 1046-1050.
Dechant, et al., Adv Exper Med Bio, (2002), vol. 513, pp. 303-334.
Supplementary European Search Report dated Jul. 22, 2009.
Blomlof and Lindskog, J Peridontol. 1998; 69: pp. 392-395.
Yaegashi, T. et al., "Effect of Hydroxylapatite Particles During Healing of Experimental Furcation Involvement in Beagle Dogs", Nihon Shishubyo Gakkai Kaishi, vol. 31, No. 1, pp. 83-99, Mar. 1989.
Takeda, K. et al., "Characteristics of High-Molecular-Weight Hyaluronic Acid as a Brain-Derived Neurotrophic Gactor Scaffold in Periodontal Tissue Regeneration", Tissue Engineering: Part A, vol. 17, pp. 955-967, 2011.
Takeda, K. et al., "Brain-Derived Neurotrophic Factor Enhances Periodontal Tissue Regeneration", Tissue Engineering, vol. 11, No. 9/10, pp. 1618-1629, 2005.
Kajiya, M. et al., "Brain-derived Neurotrophic Factor Stimulates Bone/Cementum-related Protein Gene Expression in Cementoblasts", Journal of Biol. Chem., vol. 283, No. 23, pp. 16259-16267, 2008.
Mizuno, N. et al., "Effect of Neurotrophin-4/5 on Bone/Cementum-Related Protein Expressions and DNA Synthesis in Culture of Human Periodontal Ligament Cells", Journal of Periodontol., vol. 79, No. 11, pp. 2182-2189, 2008.
Xu, W. et al., "Promotion of Functioning of Human Periodontal Ligament Cells and Human Endothelial Cells by Nerve Growth Factor", Journal of Periodontol., vol. 77, No. 5, pp. 800-807, 2006.
Bakos, D. et al., "Hydroxyapatite-collagen-hyaluronic acid composite", Biomaterials, vol. 20, pp. 191-195, 1999.
Fujishita, K. et al., "Grape Seed Extract Acting on Astrocytes Reveals Neuronal Protection Against Oxidative Stress via Interleukin-6-mediated Mechanism", Cell Mol Neruobiol, vol. 29, pp. 1121-1129, 2009.
Fujita, T. et al., P2Y1 Receptor Signaling Enhances Neuroprotection by Astrocytes Oxidative Stress via IL-6 Release in Hippocampal Cultures, GLIA, vol. 57, pp. 244-257, 2009.
Clinical Periodontology 8th edition (1996), Fermin A. Carranza et al., eds., W.B. Saunders Company, Philadelphia.
Scheres, N. et al., "Gingival and periodontal ligament fibroblasts differ in their inflammatory response to viable Porphyromonas gingivalis", Journal of Periodontol., vol. 45, pp. 262-270, 2010.
Wikesjö et al. (1999) "Periodontal Repair in Dogs: Effect of Rhbmp-2 Concentration on Regeneration of Alveolar Bone and Periodontal Attachment," J. Clin. Periodontol 26: 392-400.
Niita, Shika-gikou, (2003), vol. 31(9), pp. 1102-1105.
Kinoshita, Saishin-igaku, (2003), vol. 58, pp. 777-788.
Luukko et al., "Neurotrophin mRNA Expression in the Developing Tooth Suggests Multiple Roles in Innervation and Organogenesis", Developmental Dynamics, vol. 210, 1997, pp. 117-129.

\* cited by examiner

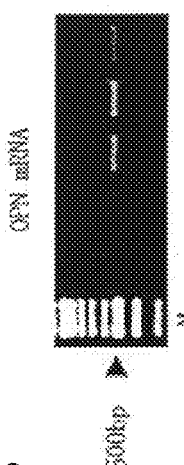
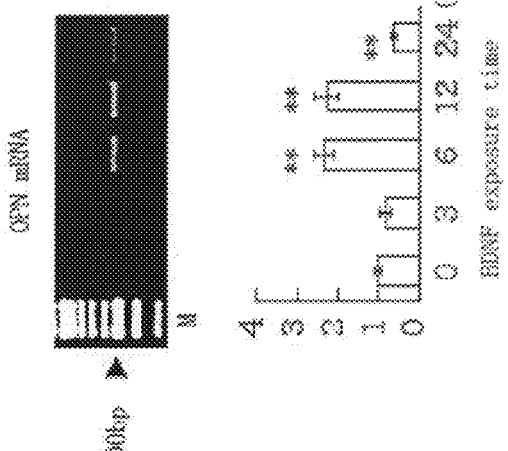
Fig. 2A
Fig. 2B
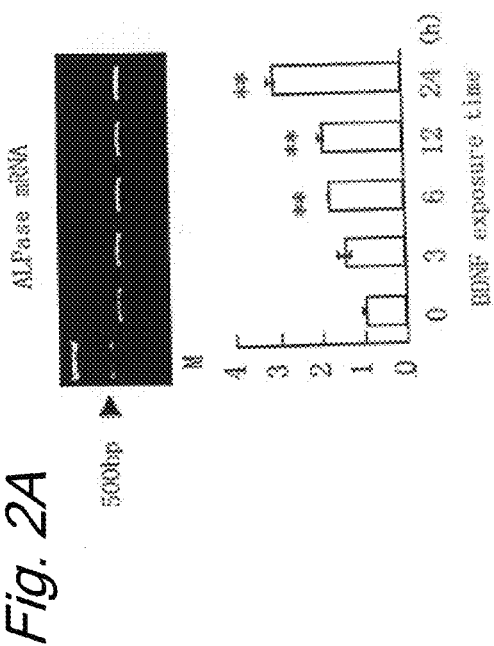
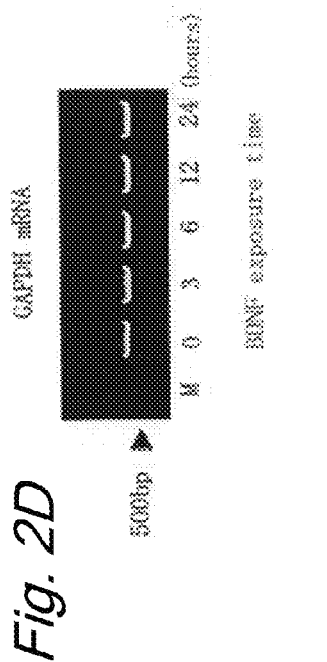
Fig. 2C
Fig. 2D
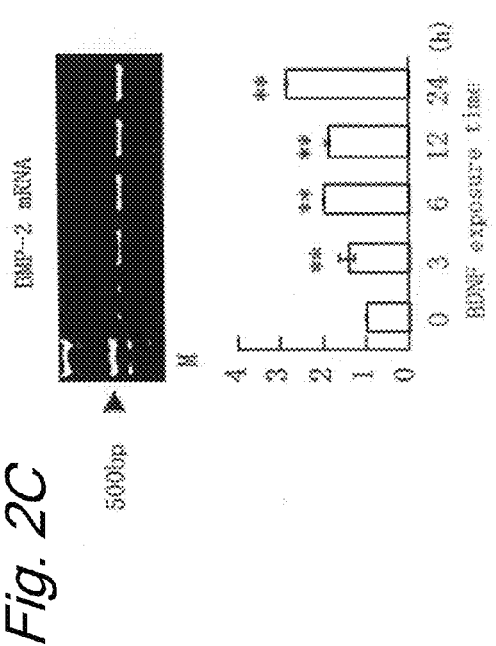

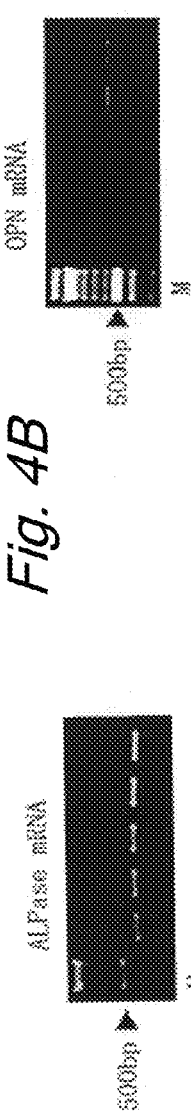
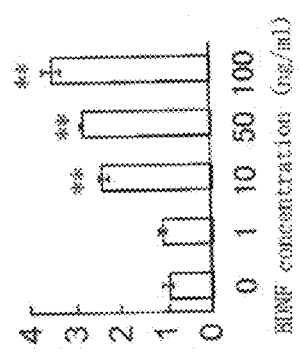
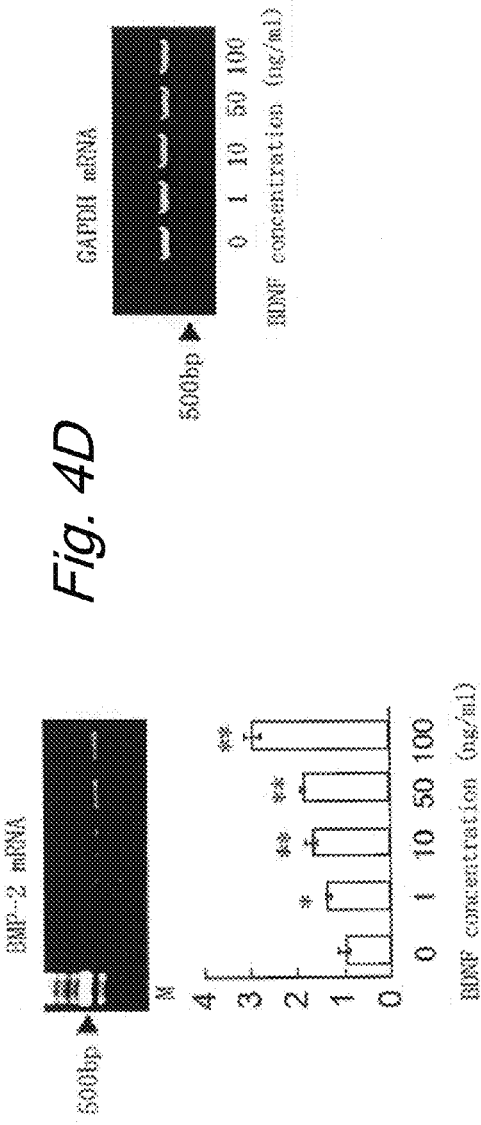
Fig. 4A
Fig. 4B
Fig. 4C
Fig. 4D (A)

(B)

(A)

(B)

(A)

(B)

(A)

(B)

NT-3 (100 ng/ml)

NGF 100μg/ml

NT-3 100µg/ml

BRAIN-DERIVED NEUROTROPHIC FACTOR OR NEUROTROPHIN-4/5 TO TREAT PERIODONTAL DISEASES AND PULPAL DISEASES

This application is a Continuation of co-pending application Ser. No. 10/571,069 filed on Dec. 7, 2006, and for which priority is claimed under 35 U.S.C. §120. application Ser. No. 10/571,069 is the national phase of PCT International Application No. PCT/JP2004/013023 filed on Sep. 8, 2004 under 35 U.S.C. §371. This application also claims priority of Application No. 316719/2003 filed in Japan on Sep. 9, 2003 under 35 U.S.C. §119. The entire contents of each of the above-identified applications are hereby incorporated by reference.

TECHNICAL FIELD

This invention relates to a therapeutic agent and a therapeutic method for periodontal diseases and pulpal diseases, a transplant for periodontal tissue regeneration, and a method for regenerating the periodontal tissue.

BACKGROUND ART

The periodontal tissue which is composed of gingiva, alveolar bone, periodontal ligament (periodontal membrane), cementum, dental pulp, etc. is essential for erecting teeth and maintaining their functions such as mastication and occlusion, and its damage or destruction will lead to the loss of teeth. Consider, for example, a periodontal disease which is reportedly afflicting about 30 million people in Japan; as the disease progresses, the periodontal, tissue becomes increasingly damaged or destroyed resulting in tooth loss. To treat damaged or destroyed periodontal tissue including the dental pulp, various methods comprising medication and surgical operation are being attempted but none of the medicaments and therapeutic methods are sufficiently effective to regenerate the damaged or destroyed periodontal tissue including the dental pulp.

Neurotrophic factors include brain-derived neurotrophic factor (BDNF), nerve growth factor (NGF), neurotrophin-3 (NT-3) and neurotrophin-4/5 (NT-4/5) and are involved in differentiation, survival, regeneration and functional maintenance of neuron. BDNF and NT-4/5 bind to the high-affinity receptor TrkB (tropomyosin receptor kinase B), NGF to TrkA, and NT-3 to TrkC.

BDNF, NGF and NT-3 are neurotrophic factors mostly present in the brain and the efficacy of BDNF and NGF has been demonstrated in experiments with animals of various disease models such as a motor neuropathy model, a Parkinson's disease model, and an Alzheimer disease model. In particular, BDNF is expected as an effective therapeutic drug for motor and peripheral nervous diseases such as amyotrophic lateral sclerosis (ALS) and peripheral neuropathies due to diabetes and chemotherapeutic agents, and for diseases involving the central nervous system such as the Alzheimer disease, the Parkinson's disease, and retina-related diseases.

These neurotrophic factors are said to play an important role not only in the central nervous system but also in the peripheral nervous system. It has been reported that the expression of BDNF, NGF, NT-3, TrkC and TrkA increased during the healing process of fractured mouse ribs (K. Asaumi et al., Bone, Vol. 26, No. 6, 625-633, 2000) and that BDNF, NGF and NT-3 enhanced the proliferation of mouse periodontal ligament cells (Y. Tsuboi et al., J Dent Res 80(3): 881-886, 2001). However, there are no detailed reports on the behavior of those neurotrophic factors in the periodontal tissue and pulp tissue.

DISCLOSURE OF THE INVENTION

Problems to be Solved by the Invention

The objects of the present invention are: to provide therapeutic agent and a therapeutic method for periodontal diseases and pulpal diseases, a transplant for periodontal tissue regeneration, and a method for regenerating the periodontal tissue.

Means for Solving the Problems

The present inventors made intensive studies with a view to solving the above-mentioned problems and found that neurotrophic factors enhanced the proliferation of human periodontal ligament cells, the expression of mRNA for bone-related proteins, and the regeneration of the periodontal tissue in dog models of a lesion in furcation regions. The present invention has been accomplished on the basis of these findings.

Thus, according to the present invention, there is provided a therapeutic agent for periodontal diseases which comprises a neurotrophic factor as an active ingredient.

The therapeutic agent of the present invention preferably regenerates the periodontal tissue.

The therapeutic agent of the present invention preferably regenerates the cementum, periodontal ligament, alveolar bone, or dental pulp.

The therapeutic agent of the present invention preferably prevents the apical invasion of gingival epithelium along the dental root surface.

The therapeutic agent of the present invention preferably enhances the production of repaired dentin in the pulp cavity. It is also preferred for the therapeutic agent to enhance the addition of repaired dentin to the inner surfaces of the pulp cavity.

In the therapeutic agent of the present invention, the neurotrophic factor is preferably a brain-derived neurotrophic factor, a nerve growth factor, neurotrophin-3, or neurotrophin-4/5.

According to another aspect of the present invention, there is provided a transplant for periodontal tissue regeneration which comprises a neurotrophic factor.

The transplant of the present invention preferably regenerates the periodontal tissue.

The transplant of the present invention preferably regenerates the cementum, periodontal ligament, alveolar bone, or dental pulp.

The transplant of the present invention preferably prevents the apical invasion of gingival epithelium along the dental root surface.

The transplant of the present invention preferably enhances the production of repaired dentin in the pulp cavity. It is also preferred for the transplant to promote the addition of repaired dentin to the inner surfaces of the pulp cavity.

In the transplant of the present invention, the neurotrophic factor is preferably a brain-derived neurotrophic factor, a nerve growth factor, neurotrophin-3, or neurotrophin-4/5.

According to still another aspect of the present invention, there is provided a method for regenerating the periodontal tissue which comprises using a neurotrophic factor.

The regenerating method of the present invention preferably regenerates the periodontal tissue.

The regenerating method of the present invention preferably regenerates the cementum, periodontal ligament, alveolar bone, or dental pulp.

The regenerating method of the present invention preferably prevents the apical invasion of gingival epithelium along the dental root surface.

In the regenerating method of the present invention, the neurotrophic factor is preferably a brain-derived neurotrophic factor, a nerve growth factor, neurotrophin-3, or neurotrophin-4/5.

According to yet another aspect of the present invention, there is provided a therapeutic method for periodontal disease which comprises administering a therapeutically effective amount of a neurotrophic factor to a subject who is suffering or prone to suffer from the disease.

The therapeutic method of the present invention preferably regenerates the periodontal tissue.

The therapeutic method of the present invention preferably regenerates the cementum, periodontal ligament, alveolar bone, or dental pulp.

The therapeutic method of the present invention preferably prevents the apical invasion of gingival epithelium along the dental root surface.

The therapeutic method of the present invention preferably enhances the production of repaired dentin in the pulp cavity. It is also preferred for the method to enhance the addition of repaired dentin to the inner surfaces of the pulp cavity.

In the therapeutic method of the present invention, the neurotrophic factor is preferably a brain-derived neurotrophic factor, a nerve growth factor, neurotrophin-3, or neurotrophin-4/5.

According to a further aspect of the present invention, there is provided use of a neurotrophic factor for producing a medicament to be used in the therapy of periodontal diseases.

The medicament preferably regenerates the periodontal tissue, in particular, the cementum, periodontal ligament, alveolar bone, or dental pulp. The medicament preferably prevents the apical invasion of gingival epithelium along the dental root surface. The medicament preferably enhances the production of repaired dentin in the pulp cavity. It is also preferred for the medicament to enhance the addition of repaired dentin to the inner surfaces of the pulp cavity. The neurotrophic factor is preferably a brain-derived neurotrophic factor, a nerve growth factor, neurotrophin-3, or neurotrophin-4/5.

According to yet a further aspect of the present invention, there is provided a repaired dentin morphogenesis enhancer comprising a neurotrophic factor as an active ingredient. The neurotrophic factor is preferably a brain-derived neurotrophic factor, a nerve growth factor, neurotrophin-3, or neurotrophin-4/5. Repaired dentin is preferably added to the inner surfaces of the pulp cavity.

According to another aspect of the present invention, there is provided a therapeutic method for pulpal disease which comprises administering a therapeutically effective amount of a neurotrophic factor to a subject who is suffering or prone to suffer from the disease in order to enhance the morphogenesis of repaired dentin. The neurotrophic factor is preferably a brain-derived neurotrophic factor, a nerve growth factor, neurotrophin-3, or neurotrophin-4/5. Repaired dentin is preferably added to the inner surfaces of the pulp cavity.

According to yet another aspect of the present invention, there is provided use of a neurotrophic factor for producing a medicament to be used for enhancing the morphogenesis of repaired dentin. The neurotrophic factor is preferably a brain-derived neurotrophic factor, a nerve growth factor, neurotrophin-3, or neurotrophin-4/5. Repaired dentin is preferably added to the inner surfaces of the pulp cavity.

BRIEF DESCRIPTION OF THE DRAWINGS

FIG. 2A shows by an electrophoretogram and a bar graph the relationship between the exposure time of BDNF and the amount of ALPase mRNA (381 bp) expression in HPL cells; HPL cells were all treated with BDNF at a final concentration of 50 ng/ml; the lane at the left end of the electrophoretogram is the marker; the vertical axis of the graph plots the relative amount of mRNA expression for each exposure time, with the amount of mRNA expression for exposure time zero being taken as unity; the horizontal axis of the graph plots the exposure time of BDNF; the vertical lines on the bars in the graph each represents the range of mean±standard deviation; ** means the statistically significant difference at $p<0.01$ (in t-test).

FIG. 2B shows by an electrophoretogram and a bar graph the relationship between the exposure time of BDNF and the amount of OPN mRNA (532 bp) expression in HPL cells; HPL cells were all treated with BDNF at a final concentration of 50 ng/ml; the lane at the left end of the electrophoretogram is the marker; the vertical axis of the graph plots the relative amount of mRNA expression for each exposure time, with the amount of mRNA expression for exposure time zero being taken as unity; the horizontal axis of the graph plots the exposure time of BDNF; the vertical lines on the bars in the graph each represents the range of mean±standard deviation; ** means the statistically significant difference at $p<0.01$ (in t-test).

FIG. 2C shows by an electrophoretogram and a bar graph the relationship between the exposure time of BDNF and the amount of BMP-2 mRNA (440 bp) expression in HPL cells; HPL cells were all treated with BDNF at a final concentration of 50 ng/ml; the lane at the left end of the electrophoretogram is the marker; the vertical axis of the graph plots the relative amount of mRNA expression for each exposure time, with the amount of mRNA expression for exposure time zero being taken as unity; the horizontal axis of the graph plots the exposure time of BDNF; the vertical lines on the bars in the graph each represents the range of mean±standard deviation; ** means the statistically significant difference at $p<0.01$ (in t-test).

FIG. 2D is an electrophoretogram showing the relationship between the exposure time of BDNF and the amount of GAPDH mRNA expression in HPL cells; HPL cells were all treated with BDNF at a final concentration of 50 ng/ml; the lane at the left end of the electrophoretogram is the marker.

FIG. 4A shows by an electrophoretogram and a bar graph the relationship between the dose at which BDNF was administered to HPL cells and the amount in which ALPase mRNA was expressed; the respective concentrations of BDNF were allowed to act on the HPL cells for 24 hours; the lane at the left end of the electrophoretogram is the marker; the vertical axis of the graph plots the relative amount of mRNA expression at each dose of BDNF, with the amount of mRNA expression for zero dose being taken as unity; the horizontal axis of the graph plots the concentration of BDNF (ng/ml); the vertical lines on the bars in the graph each represents the range of mean±standard deviation; ** means the statistically significant difference at $p<0.01$ (in t-test).

FIG. 4B shows by an electrophoretogram and a bar graph the relationship between the dose at which BDNF was administered to HPL cells and the amount in which OPN mRNA was expressed; the respective concentrations of BDNF were allowed to act on the HPL cells for 12 hours; the lane at the left end of the electrophoretogram is the marker; the vertical axis of the graph plots the relative amount of mRNA expression at each dose of BDNF, with the amount of mRNA expression for zero dose being taken as unity; the horizontal axis of the graph plots the concentration of BDNF (ng/ml); the vertical lines on the bars in the graph each represents the range of mean±standard deviation; ** means the statistically significant difference at $p<0.01$ (in t-test).

FIG. 4C shows by an electrophoretogram and a bar graph the relationship between the dose at which BDNF was administered to HPL cells and the amount in which BMP-2 mRNA was expressed; the respective concentrations of BDNF were allowed to act on the HPL cells for 24 hours; the lane at the left end of the electrophoretogram is the marker; the vertical axis of the graph plots the relative amount of mRNA expression at each dose of BDNF, with the amount of mRNA expression for zero dose being taken as unity; the horizontal axis of the graph plots the concentration of BDNF (ng/ml); the vertical lines on the bars in the graph each represents the range of mean±standard deviation; * and ** mean the statistically significant differences at $p<0.05$ and $p<0.01$, respectively (in t-test).

FIG. 4D is an electrophoretogram showing the relationship between the dose at which BDNF was administered to HPL cells and the amount at which GAPDH mRNA (613 bp) was expressed.

FIG. 5 (B) is a bar graph showing the relationship between the dose at which BDNF was administered to HPL cells and the amount in which BMP-2 was secreted; the respective concentrations of BDNF were allowed to act on the HPL cells for 24 hours; the vertical axis plots the amount of BMP-2 secretion (pg/ml) and the horizontal axis plots the concentration of BDNF (ng/ml); FIG. 5 (C) is a bar graph showing the relationship between the exposure time of BDNF and the amount in which BMP-2 was secreted in HPL cells; the cells were treated with BDNF at a final concentration of 50 ng/ml; the vertical axis plots the amount of BMP-2 secretion (pg/ml) and the horizontal axis plots the exposure time of BDNF; the vertical lines on the bars in the graphs (A)-(C) each represents the range of mean±standard deviation; ** means the statistically significant difference at $p<0.01$ (in t-test).

FIG. 7 (B) is a bar graph showing the relationship between the exposure time of BDNF and the amount in which type I collagen was synthesized; the cells were treated with BDNF at a final concentration of 50 ng/ml; the vertical axis plots the amount (μg/ml) in which type I collagen was synthesized and the horizontal axis plots the exposure time of BDNF; the vertical lines on the bars in the graphs (A) and (B) each represents the range of mean±standard deviation; * and ** mean the statistically significant differences at $p<0.05$ and $p<0.01$, respectively (in t-test).

BEST MODES FOR CARRYING OUT THE INVENTION

Figure 1:
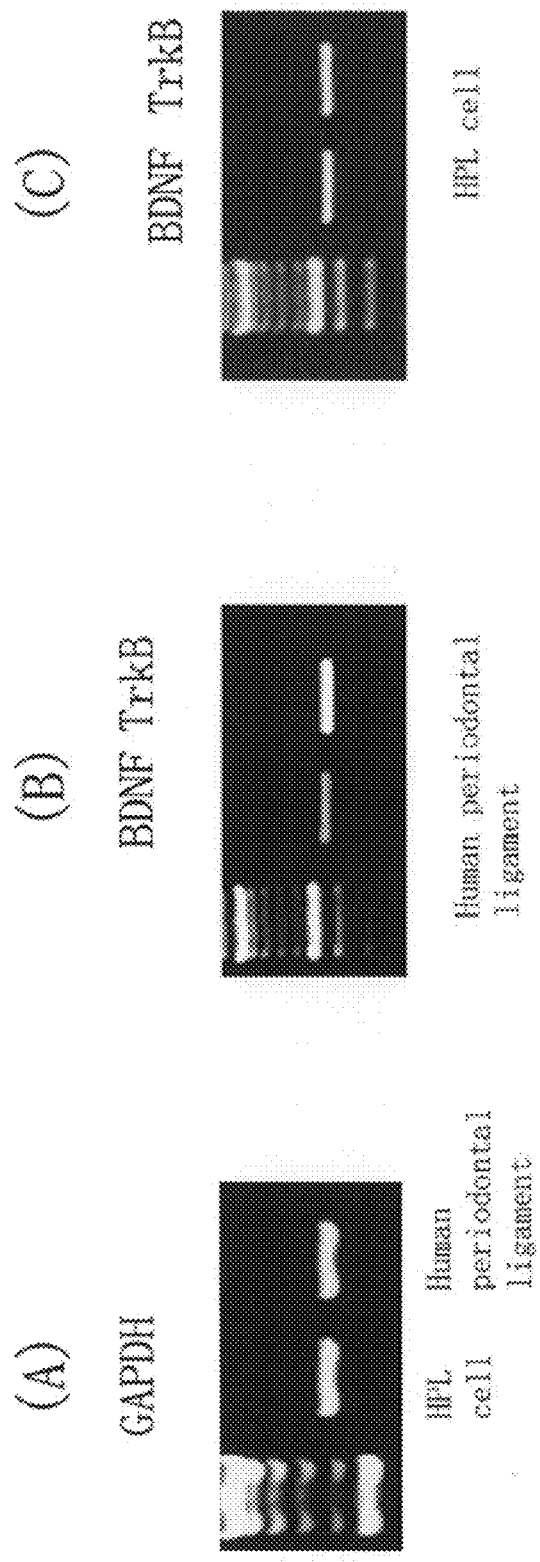
FIG. 1 is a set of electrophoretograms showing the expression of mRNA for BDNF and TrkB in HPL cells and human periodontal ligament; the lane at the left end of each electrophoretogram is the marker; (A) shows the expression of mRNA (613 bp) of glyceraldehyde 3-phosphate dehydrogenase (GAPDH) in human periodontal ligament and HPL cells; (B) shows the expressions of mRNA (438 bp) of BDNF and mRNA (434 bp) of TrkB in human periodontal ligament; (C) shows the expression of mRNA for BDNF and TrkB in HPL cells.
Figures 3A, 3B:
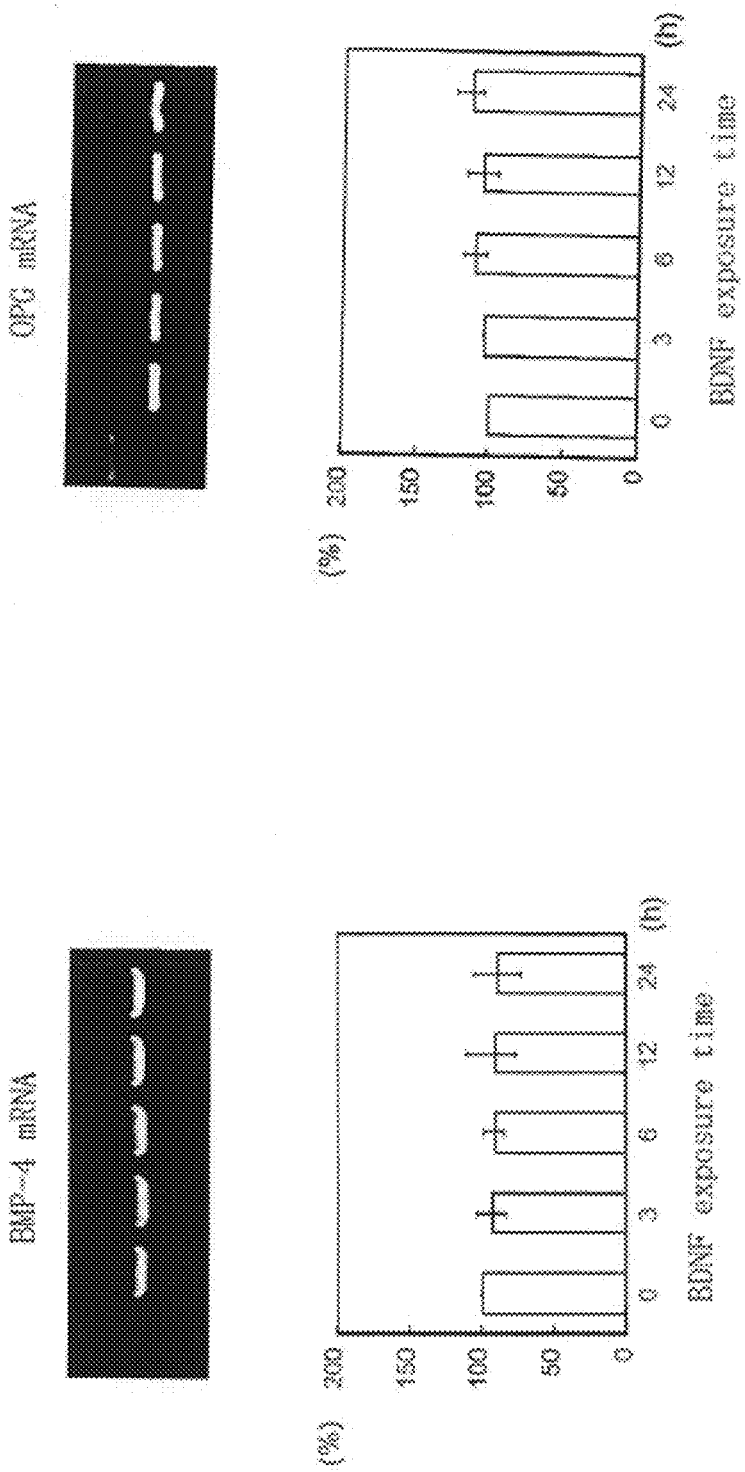
FIG. 3A shows by an electrophoretogram and a bar graph the relationship between the exposure time of BDNF and the amount of BMP-4 mRNA (339 bp) expression in HPL cells; HPL cells were all treated with BDNF at a final concentration of 50 ng/ml; the lane at the left end of the electrophoretogram is the marker; the vertical axis of the graph plots the percentage of the amount of mRNA expression for each exposure time, with the amount of mRNA expression for exposure time zero being taken as 100; the horizontal axis of the graph plots the exposure time of BDNF; the vertical lines on the bars in the graph each represents the range of mean±standard deviation.
FIG. 3B shows by an electrophoretogram and a bar graph the relationship between the exposure time of BDNF and the amount of OPG mRNA (736 bp) expression in HPL cells; HPL cells were all treated with BDNF at a final concentration of 50 ng/ml; the lane at the left end of the electrophoretogram is the marker; the vertical axis of the graph plots the percentage of the amount of mRNA expression for each exposure time, with the amount of mRNA expression for exposure time zero being taken as 100; the horizontal axis of the graph plots the exposure time of BDNF; the vertical lines on the bars in the graph each represents the range of mean±standard deviation.

On the following pages, more specific embodiments of the present invention and methods for carrying out the invention are described.

The term "periodontal tissue" as used herein means a tissue composed of the gingiva, alveolar bone, periodontal ligament (periodontal membrane), and cementum.

"Gingiva" means the soft tissue that covers the cervical root surface and part of the alveolar bone; it consists of the gingival epithelium and the gingival lamina propria.

"Periodontal ligament" means the connective tissue that bridges the alveolar bone and the cementum and is also known as the periodontal membrane.

"Alveolar bone" is classified into the alveolar bone proper corresponding to the compact bone of the alveolar wall surrounding the dental root and the outer supporting alveolar bone consisting of the spongiosa and the compact bone.

"Cementum" is the hard tissue in the outermost layer of the dental root and is classified into the cellular cementum that contains cementocytes and the acellular cementum that has no cementocytes.

"Dental pulp" is a tissue that controls the vital reactions of the teeth and forms dentin as it reacts to physiological or pathological stimuli. It is composed of pulp cells, nerve fibers, extracellular matrix, blood vessels, etc.

"Regeneration" means reconstruction and reproduction of lost tissues, destroyed tissues and damaged tissues; "regeneration of the periodontal tissue" means restoring the periodontal tissue to an initial state so that it functions properly.

"Repair" means healing of a wounded tissue as in case where in, the structure and functions of the wound have not yet been fully restored; and "repair of the periodontal tissue" includes the formation of an epithelial attachment to the dental root surface.

"Preventing apical invasion of gingival epithelium along the dental root surface" means preventing gingival epithelium cells from growing toward the root apex along the dental root surface.

"Transplant for periodontal tissue regeneration" is a material that enhances the regeneration of the periodontal tissue. In order to cause neurotrophic factors such as BDNF to act on a given in vivo site (e.g. a missing site of the alveolar bone) at a specified concentration, a certain scaffold is necessary. A material working as such a scaffold is combined with a neurotrophic factor such as BDNF to provide the transplant of the present invention.

"Periodontal diseases" means inflammatory diseases involving the periodontal tissue that are caused by localized bacteria and the like.

"Repaired dentin" means dentin formed as the result of external stimuli.

"Pulpal diseases" means inflammatory diseases, retroplasia, etc. of the dental pulp.

The present invention is applicable to warm-blooded animals such as humans and it is particularly preferred to apply to humans.

The neurotrophic factors such as BDNF, NGF, NT-3 and NT-4/5, which are to be used in the present invention, may be artificially produced by gene recombination or chemical synthesis; alternatively, they may be of native types.

The therapeutic agent for periodontal diseases of the present invention is preferably applied topically in the form of a drug for external application. If desired, the therapeutic agent may be filled into a syringe or the like and injected into a periodontal pocket. It is also possible to administer the therapeutic agent to a missing part of the periodontal tissue during periodontal surgery. In this case, in order to assure a prolonged action at a specified concentration, it is also preferred to use the therapeutic agent of the present invention with an absorbable material such as a sheet, or a sponge, etc. The therapeutic agent is preferably administered after removing the infected periodontal tissue. The therapeutic agent of the present invention can also be administered locally in the form of an injection. For example, it may be injected into the gingiva of a periodontal pocket or it may be injected into a cavity in the periodontal membrane near the alveolar crest. It may also be injected near the root apex.

The repaired dentin morphogenesis enhancer of the present invention is preferably administered topically in the form of a drug for external application. For example, the repaired dentin morphogenesis enhancer in liquid, cream, paste or other form may be applied to the pulp exposure; alternatively, it may be applied to the pulp amputation or extirpation of the pulp. If desired, a sheet or sponge impregnated with the active ingredient may be applied to provide temporary seal for a certain period. Alternatively, in the case of replanting a tooth that dropped due to trauma or other cause, the enhancer may be applied to the root apex or the like.

The therapeutic agent for periodontal diseases and the repaired dentin morphogenesis enhancer according to the present invention may assume a variety of dosage forms including those for external application such as cream, ointment and lotion which are produced by conventional pharmaceutical formulating procedures using pharmaceutically acceptable carriers or diluents; they may also include injections based on aqueous solvents. The therapeutic agent and the enhancer may also be in a powder dosage form and dissolved in a solubilizing fluid such as purified water just prior to use.

The therapeutic agent for periodontal diseases and the repaired dentin morphogenesis enhancer according to the present invention may be administered in doses that vary with the age of the subject, their sex, severity of the disease and other factors; in topical administration, normally, the dose is preferably in the range of $1 \times 10^{-12}$ g to $1 \times 10^{-3}$ g, more preferably $1 \times 10^{-11}$ g to $1 \times 10^{-7}$ g, most preferably $1 \times 10^{-10}$ g to $1 \times 10^{-8}$ g, as a neurotrophic factor per tooth. Generally speaking, doses for local application by injection may be smaller than those used for external application.

The transplant of the present invention preferably contains $1 \times 10^{-12}$ g to $1 \times 10^{-3}$ g, more preferably $1 \times 10^{-11}$ g to $1 \times 10^{-8}$ g, most preferably $1 \times 10^{-10}$ g to $1 \times 10^{-9}$ g, of neurotrophic factors in a dose to be applied to one defect at furcation.

The therapeutic agent for a periodontal disease, the repaired dentin morphogenesis enhancer and the transplant according to the present invention may be used in combination with other drugs as long as their efficacy is not impaired. BDNF, NGF, NT-3 and NT-4/5 may be used in combination with each other. They may also be used in combination with bone marrow derived mesemchymal stem cells (MSC), periodontal ligament cells, gingival fibroblasts, vascular endothelial cells, etc. They may also be combined with calcium hydroxide preparations, antibacterial agents, etc.

The material to be combined with the neurotrophic factor in the transplant of the present invention may be any material that causes no damage to the living body and can maintain the neurotrophic factor at the site to which it has been administered; preferred examples are a porous sheet and sponge. More preferred are biodegradable protein materials (collagen, gelatin, albumin, and platelet-rich plasma (PRP)) and tissue absorbing materials (polyglycolic acid (PGA), polylactic acid (PLA), poly(lactic acid-co-glycolic acid) (PLGA), hyaluronic acid (HA), and tricalcium phosphate (TCP)) since they need not be extracted later. Examples include TERU-PLUG®️ (trade name of TERUMO CORPORATION), GC Membrane (trade name of GC Co., Ltd.) and Osferion (trade name of OLYMPUS CORPORATION).

EXAMPLES

The present invention is described in greater detail by means of the following examples.

Example 1

The effects of BDNF on human periodontal ligament cells (HPL cells) and human gingival keratinocytes (HGK) were investigated.

(1) Cells Used
(i) Human Periodontal Ligament Cells (HPL Cells)

HPL cells were separated from the periodontal ligament of a healthy human premolar that had been extracted for the sake of convenience in orthodontic treatment. In order to prevent the entrance of cells from other connective tissues around the periodontal ligament, the healthy periodontal ligament at the middle of the dental root excluding the cervical root surface and root apex of the extracted human premolar was detached with a scalpel and shredded. The shredded tissue was attached to a cell culture Petri dish of 60 mm diameter (CORNING, N.Y.) and cultivated at 37° C. in a 5% $CO_2$ gas phase. The culture medium was Dulbecco's modified Eagle's medium (DMEM, NISSUI PHARMACEUTICAL CO., LTD., Tokyo) supplemented with 10% FBS (GIBCO, Buffalo, N.Y.), penicillin (100 U/ml; MEIJI SEIKA KAISHA, LTD., Tokyo), streptomycin (100 μg/ml; MEIJI SEIKA KAISHA, LTD., Tokyo), and amphotericin B (1 μg/ml; GIBCO); this culture medium is hereinafter designated "medium A". The HPL cells in culture at passage 4-8 were used for the following experiment.

(ii) Human Gingival Keratinocytes (HGK)

Gingiva was obtained from patients after having their informed consent about the need to perform experiments using human cultured cells and the purpose of using the gingiva. The patients were suffering from pericoronitis of the wisdom teeth and when the causative wisdom teeth were being extracted, gingival pieces were acquired from an excess gingival flap. The obtained gingival pieces were treated with Dulbecco's PBS(−) (PBS(−) of NISSUI PHARMACEUTICAL CO., LTD.) supplemented with 0.01% ethylenediaminetetraacetic acid (EDTA) and 0.025% trypsin at 4° C. for 24 hours to separate HGK. Primary culture was performed on MCDB 153 medium (Sigma) supplemented with bovine insulin (10 μg/ml; Sigma, St. Louis, Mo., USA), human transferrin (5 μg/ml; Sigma), 2-mercaptoethanol (10 μM), 2-aminoethanol (10 μM), sodium selenite (10 μM), bovine pituitary gland extract (50 μg/ml), penicillin (100 U/ml), streptomycin (100 μg/ml), and amphotericin B (50 ng/ml); this culture medium is hereinafter designated "medium C". The culture was performed on a Petri dish of 60 mm diameter (SUMILON CELTITE C-1 of SUMITOMO BAKELIGHT COMPANY LIMITED, Tokyo) coated with bovine type I collagen at 37° C. in a 5% $CO_2$ gas phase. The HGK in culture at passage 3-4 were used for the following experiment.

(2) Expression of BDNF and its Receptor in HPL Cells

The expression of mRNA for BDNF and TrkB in HPL cells and human periodontal ligament was investigated by reverse transcriptase PCR using a 1st Strand cDNA Synthesis Kit for RT-PCR (Roche, Indianapolis).

The HPL cells obtained in (1)(i) above were recovered at the time when they reached confluence; the cells were then dissolved in ISOGEN (Nippon Gene, Tokyo) and centrifuged after adding chloroform; to the resulting aqueous phase, isopropanol was added to extract total RNA.

The human periodontal ligament obtained in (1)(i) above was homogenized in ISOGEN and centrifuged after adding chloroform; to the resulting aqueous phase, isopropanol was added to extract total RNA.

Portions (1 μg each) of the purified total RNA were reverse transcribed using oligo dT primers; the resulting cDNA was amplified by 30 cycles of PCR and electrophoresed on 1.5% agarose gel. Glyceraldehyde 3-phosphate dehydrogenase (GAPDH) was used as a control.

The results are shown in FIG. 1. The control was glyceraldehyde 3-phosphate dehydrogenase (GAPDH). As is clear from the electrophoretograms, mRNAs of BDNF and TrkB were expressed in the human periodontal ligament and it was confirmed that mRNAs of BDNF and TrkB had also been expressed in the HPL cells cultured after being separated from the human periodontal ligament.

(3) Treatment of the Cells with BDNF
(i) HPL Cells

The HPL cells obtained in (1)(i) above were cultivated on Petri dishes of 60 mm diameter (SUMILON CELTITE C-1) coated with bovine type I collagen at 37° C. in a 5% $CO_2$ gas phase for 13 days at a density of $3.5 \times 10^5$ cells per Petri dish using medium A supplemented with 50 μg/ml of L-ascorbic acid. The culture medium used in this cultivation is designated "medium B". The medium was changed once every two days. At 0, 3, 6, 12 and 24 hours before the end of cultivation at day 14, the cells were washed twice with DMEM and medium was changed for a serum-free culture medium containing BDNF (Recombinant Human BDNF, R&D System, Minneapolis, USA) at a final concentration of 0, 1, 10, 50 or 100 ng/ml (the medium being DMEM supplemented with penicillin (100 U/ml), streptomycin (100 μg/ml), amphotericin B (1 μg/ml; GIBCO) and L-ascorbic acid (50 μg/ml)). This culture medium is designated "medium D".

(ii) HGK

The HGK obtained in (1)(ii) above were inoculated on a 96-well plate (SUMILON CELTITE C-1 Plate 96F of SUMITOMO BAKELIGHT COMPANY LIMITED) coated with bovine type I collagen at a density of $2 \times 10^3$ cells/well and cultivated at 37° C. in a 5% $CO_2$ gas using medium C. The medium was changed once every two days. At day 4 or 5 in a cell proliferation phase, the cells on the plate were washed twice with MCDB 153 medium and medium was changed for a culture medium containing BDNF at a final concentration of 0, 1, 10, 25, 50 or 100 ng/ml (the medium having the same composition as medium C except that it did not contain a bovine pituitary extract). The cell was cultured for 24 hours.

(4) Expression of Bone-Related Proteins in HPL Cells
(i) Expression of mRNA

HPL cells were treated with BDNF at a final concentration of 0, 1, 10, 50 or 100 ng/ml by the same procedure as described in (3)(i) above and total RNA was extracted from the thus treated HPL cells with ISOGEN and purified. The expression of mRNA for alkali phosphatase (ALPase), bone morphogenetic protein-2 (BMP-2), bone morphogenetic protein-4 (BMP-4), osteopontin (OPN) and osteoprotegerin (OPG) was quantitatively analyzed by monitoring the process of generation of PCR products in real-time using ABI PRISM 7700 (Applied Biosystems, Tokyo) (real-time PCR method). GAHPD was used as a control.

The results of measuring the time course effect of BDNF on the expression of mRNA for the respective bone-related proteins are shown in FIGS. 2A-2C, 3A and 3B, and the results of measuring the dose effect of BDNF are shown in FIGS. 4A-4C. In each graph, * and ** mean $p < 0.05$ and $p < 0.01$, respectively (statistical testing by t-test).

As is clear from those Figures, BDNF had no effect on the expression of mRNA for OPG and BMP-4 but increased the amount of mRNA expression for ALPase, BMP-2 and OPN in both a dose- and a time-dependent manner.

(ii) Expression of Proteins

The HPL cells obtained in (1)(i) above were seeded on a 48-well plate (SUMILON CELTITE C-1 Plate 48F of SUMITOMO BAKELITE COMPANY LIMITED) coated with bovine type I collagen at a density of $1 \times 10^4$ cells/well and cultivated for 13 days using medium B. The medium was changed once every two days. Twenty-four hours before the end of cultivation at day 14, the cells on the plate were washed twice with DMEM and medium was changed for serum-free medium D containing BDNF at a final concentration of 0, 1, 10, 25, 50 or 100 ng/ml. After the end of culture, the supernatant was recovered and the amounts of OPN and BMP-2 secreted in the supernatant were measured by ELISA. For measuring the secreted OPN, a sandwich ELISA kit (IBL, Gunma) was used, and a sandwich ELISA kit (R&D System) was used to measure the secreted BMP-2.

Figure 5:
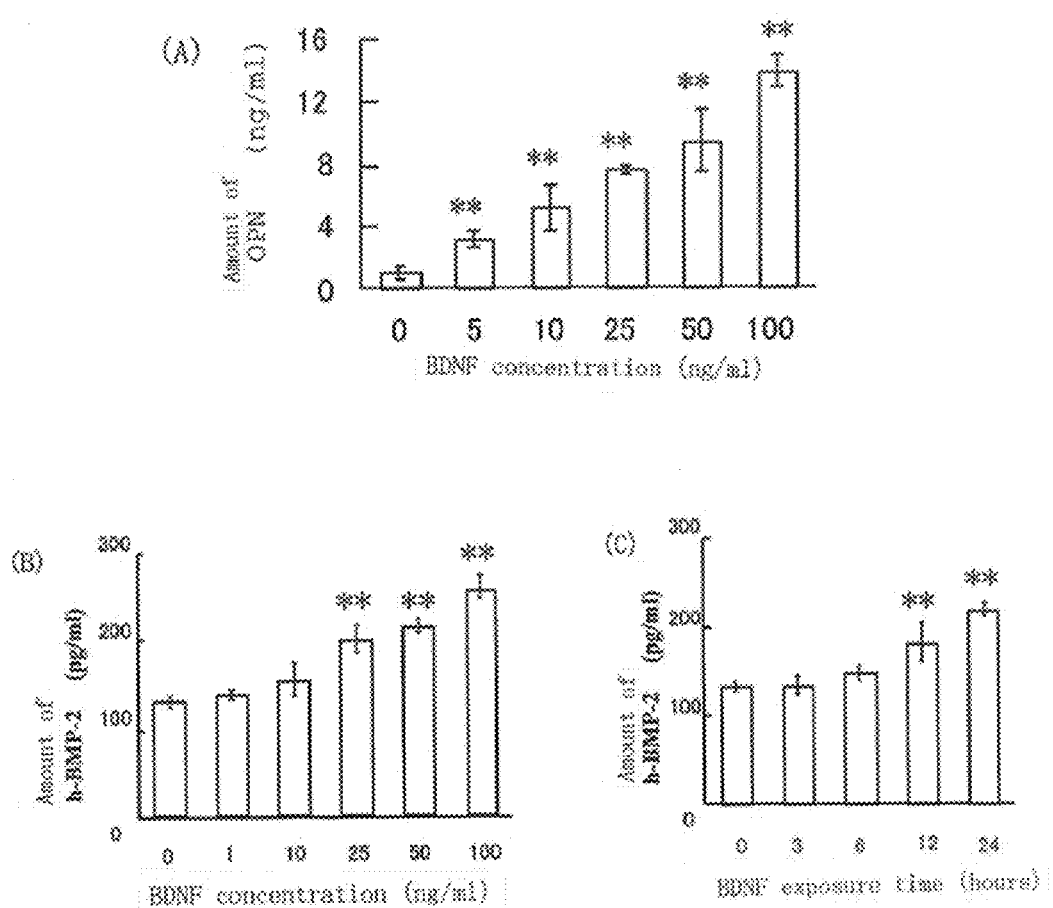
FIG. 5 (A) is a bar graph showing the relationship between the dose at which BDNF was administered to HPL cells and the amount in which OPN was secreted; the respective concentrations of BDNF were allowed to act on the HPL cells for 12 hours; the vertical axis plots the amount of OPN secretion (ng/ml) and the horizontal axis plots the concentration of BDNF (ng/ml)

FIG. 5 shows the results of measuring the time course effect and the dose effect of BDNF on the secretion of OPN and BMP-2 in HPL cells. In each graph, * and ** mean $p<0.05$ and $p<0.01$, respectively (statistical testing by t-test). As is clear from FIG. 5, BDNF enhanced the secretion of OPN and BMP-2 in HPL cells.

(5) Proliferation of HPL Cells and HGK

The effects of BDNF on the ability of HPL cells and HGK to synthesize DNA were measured by ELISA using a Cell Proliferation ELISA System, Version 2 (Amersham Pharmacia Biotech).

The HPL cells obtained in (1)(i) above were seeded on a 96-well plate (SUMILON CELTITE C-1 Plate 96F) coated with bovine type I collagen at a density of $5 \times 10^3$ cells/well and cultivated for 10 days using medium B. The cells were washed twice with DMEM and cultivated for 24 hours on medium B (supplemented with 0.3% FBS instead of 10% FBS); thereafter, the medium was changed for a medium prepared by adding BDNF to the same medium at a final concentration of 0, 1, 10, 25, 50 or 100 ng/ml; the cell was cultured for an additional 24 hours. Two hours before the end of the culture (viz. 22 hours after the addition of BDNF), bromodeoxyuridine (BrdU) was added to each well at a concentration of 10 ng/ml so that it was incorporated into the cells. The culture was performed at 37° C. in a 5% $CO_2$ gas phase.

The HGK obtained in (1)(ii) above were cultivated and treated with BDNF by the same procedures as in (3)(ii) above. Two hours before the end of the culture (viz. 22 hours after the addition of BDNF), bromodeoxyuridine (BrdU) was added to each well at a concentration of 10 ng/ml so that it was incorporated into the cells.

After the end of culture, the HPL cells and HGK were fixed and then blocking was performed; a peroxidase labeled anti-BrdU antibody was allowed to act on the cells at room temperature for 2 hours and a TMB (3,3',5,5'-tetramethylbenzidine) substrate was added to measure the absorbance at a wavelength of 450 nm with an absorptiometer (MICRO PLATE READER, TOSOH). As a control, cells on which basic fibroblast growth factor (bFGF) had been allowed to act at final concentrations of 0, 0.3, 1, 3, 5 and 10 ng/ml for 24 hours were treated in the same way so as to measure their ability to synthesize DNA.

Figure 6:
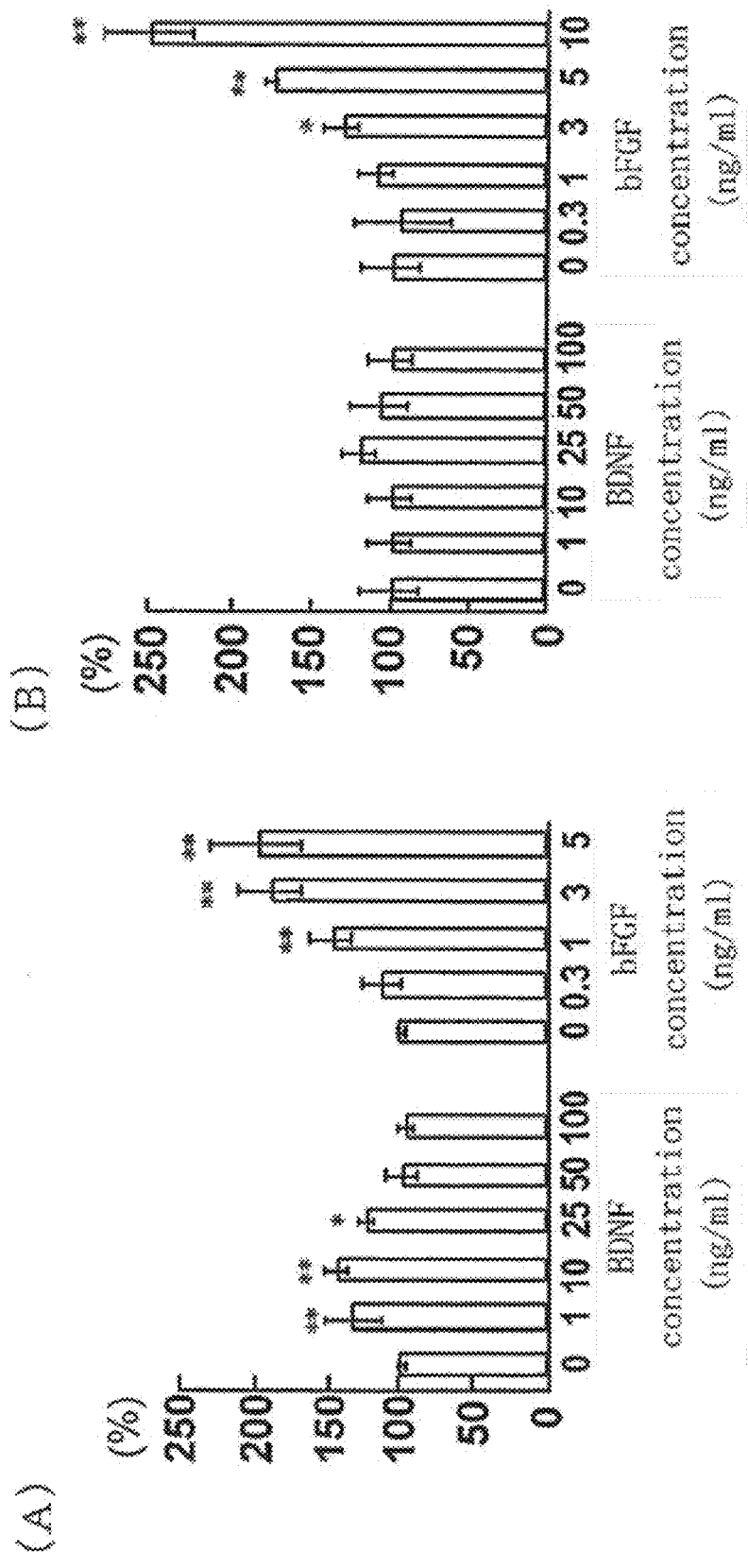
FIG. 6 shows by means of a bar graph the relationship between the dose at which BDNF was administered and the ability of HPL cells and HGK to synthesize DNA; the respective concentrations of BDNF were allowed to act on HPL cells and HGK for 24 hours; the vertical axis of each graph plots the relative ability to synthesize DNA at each dose of BDNF or bFGF, with the ability to synthesize DNA in the absence of BDNF or bFGF (i.e. at zero concentration of BDNF or bFGF) being taken as 100; the horizontal axis plots the concentration of BDNF or bFGF (ng/ml); the vertical lines on the bars in the graphs each represents the range of mean±standard deviation; * and ** mean the statistically significant differences at $p<0.05$ and $p<0.01$, respectively (in t-test); (A) shows the ability to synthesize DNA in HPL cells, and (B) shows the ability to synthesize DNA in HGK.

The results are shown in FIG. 6; (A) is a bar graph showing the effects on HPL cells, and (B) is a bar graph showing the effects on HGK. In each graph, * and ** mean $p<0.05$ and $p<0.01$, respectively (statistical testing by t-test).

As is clear from FIG. 6, BDNF enhanced the DNA synthesizing ability of HPL cells but had no effect on the DNA synthesizing ability of HGK.

(6) Collagen Synthesis by HPL Cells

The HPL cells obtained in (1)(i) above were seeded on a 48-well plate coated with bovine type I collagen and cultivated for 13 days using medium B. The medium was changed once every two days. At 0, 3, 6, 12 or 24 hours before the end of cultivation at day 14, the cells on the plate were washed twice with DMEM and medium was changed for serum-free medium D containing BDNF at a final concentration of 0, 1, 10, 25, 50 or 100 ng/ml.

Using a Procollagen type I C-peptide (PIP) EIA Kit (TAKARA), the amount in which the HPL cells synthesized collagen was measured by ELISA. Using a monoclonal antibody (peroxidase-labeled) specific to type I procollagen C-terminal propeptide (PIP), the amount of collagen synthesized in the supernatant of the culture of HPL cells was determined by measuring the absorbance at a wavelength of 450 nm with an absorptiometer (MICRO PLATE READER).

Figure 7:
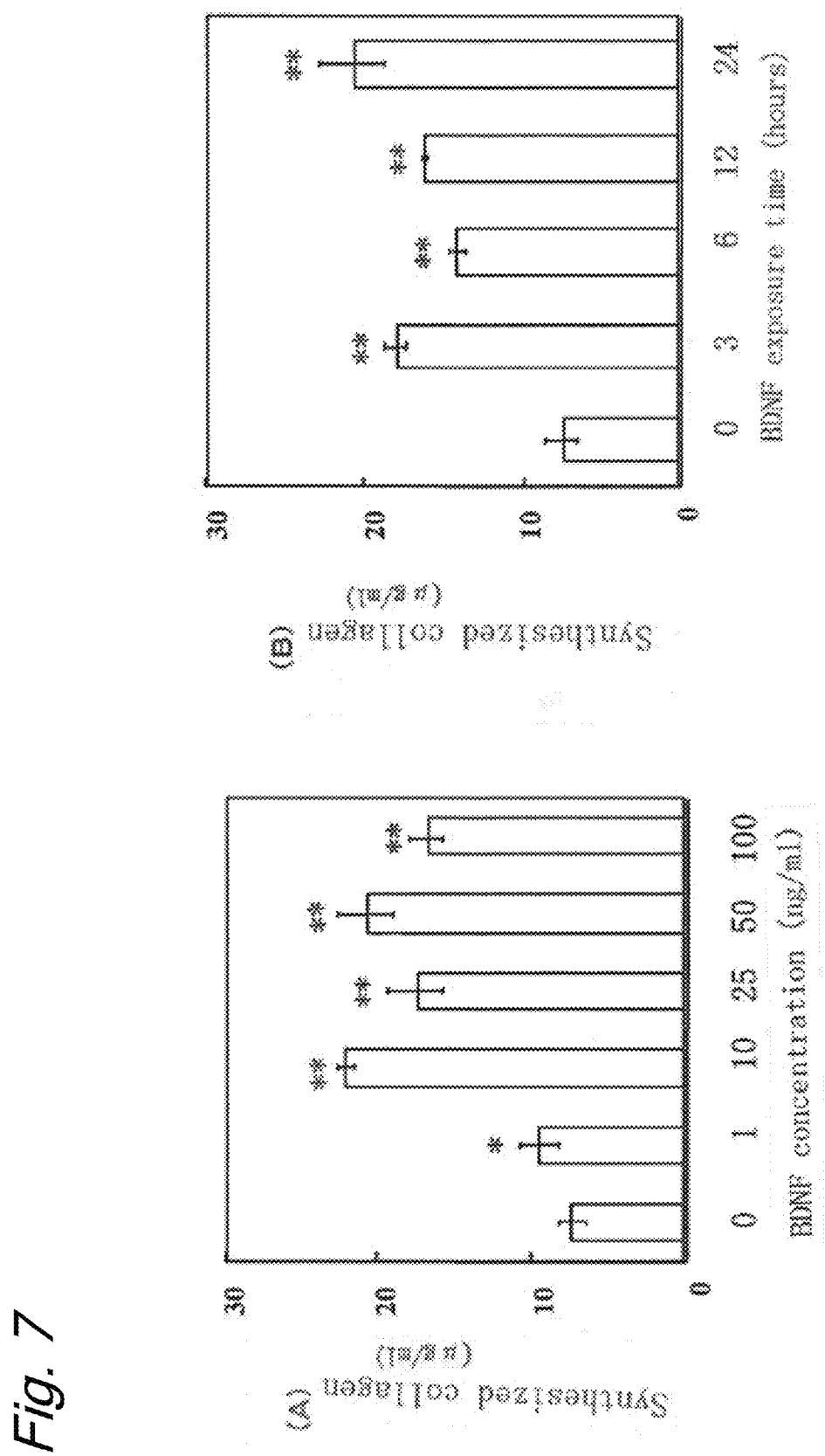
FIG. 7 (A) is a bar graph showing the relationship between the dose at which BDNF was administered to HPL cells and the amount in which type I collagen was synthesized; the respective concentrations of BDNF were allowed to act on HPL cells for 24 hours; the vertical axis plots the amount (μg/ml) in which type I collagen was synthesized and the horizontal axis plots the concentration of BDNF (ng/ml)

The results are shown in FIG. 7; (A) shows the results of measuring the dose effect of BDNF on the synthesis of type I collagen, and (B) shows the results of measuring the time course effect. As is clear from FIG. 7, BDNF increased the amount of type I collagen synthesized by HPL cells.

Example 2

The effect of BDNF on beagle dogs as a model of class III furcation defect was investigated.

TERUPLUG® (trade name of TERUMO CORPORATION) of 8 mm diameter×5 mm was impregnated with 25 µl each of BDNF solutions (in sterile physiological saline) at concentrations of 5, 25 and 50 µg/ml to prepare transplants.

Seven female beagle dogs (12-20 months old, weighing 10-14 kg) were subjected to scaling and root planning of the teeth with a hand scaler while they were under sedation with intramuscularly injected DOMITOR (MEIJI SEIKA KAISHA, LTD.) Thereafter, at a frequency of once every two days, the oral cavity of each animal was brushed and cleaned by the gargle ISOJIN (trade name of MEIJI SEIKA KAISHA, LTD.) containing povidone iodine as an active ingredient; this practice was continued for a month to establish a clinically healthy periodontal tissue in each animal.

The beagle dogs were subjected to general anesthesia by intravenous injection of a pentobarbital-containing anesthetic and local infiltrated anesthesia was applied to the mandibular buccal gingiva on both the right and left sides; the gingival sulcus was incised between the distal part of the first premolar and the mesial part of the first molar and the gingiva was detached to form a mucoperiosteal flap. Subsequently, the alveolar bones at the furcation regions of the second, third and fourth premolars on both the right and left sides were removed with a round bur and a bone chisel to prepare bone defects at furcation of class III (according to the classification by Lindhe & Nyman). The size of each bone defect was such that it extended from the area beneath the untreated furcation to about 4 mm toward the root apex.

The residual cementum on the exposed dental root surface was removed with a hand scaler and the interior of each bone defect at the furcation was thoroughly washed with physiological saline to rinse off the debris, followed by packing with the TERUPLUG® transplant of 8 mm diameter×5 mm per site. A TERUPLUG® transplant of 8 mm diameter×5 mm that did not contain BDNF but which was only impregnated with 25 µl of sterile physiological saline was packed into the same bone defect to prepare a control.

Six weeks after the operation, the animals were systemically perfused with 4% paraformaldehyde under general anesthesia by intravenous injection of a pentobarbital-containing anesthetic. After the perfusion, the mandible of each animal was dissected and the treated teeth and periodontal tissue were extracted en bloc. The obtained sample was fixed with 4% paraformaldehyde, decalcified with 10% EDTA, followed by dehydration with graded alcohol and embedding in paraffin in accordance with the usual practice. From this specimen, serial sections (about 5 µm thick) were cut in the mesial-distal plane through the buccal-lingual extension of the tooth and they were stained with hematoxylin and eosin (H&E).

Among the thus prepared tissue specimens, those which were cut in the mesial-distal plane through the buccal-lingual extension of the tooth and which had been cut near the midroot were chosen and subjected to tissue examination and measurement with an optical microscope (ECLIPSE E600, NIKON). The percent bone regeneration was expressed as the ratio (in percentage) of the area of the regenerated alveolar bone to the area of the exposed defect at furcation. The percent cementum regeneration was expressed as the ratio (in percentage) of the length of the regenerated cementum to the length of the exposed dental root surface.

Figure 8:
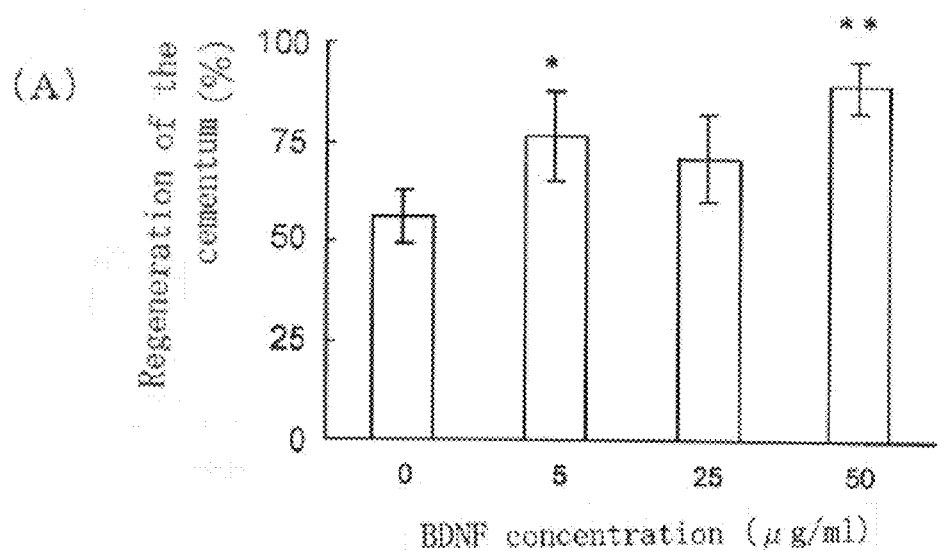
FIG. 8 shows by means of a bar graph the relationship between the dose at which BDNF was administered to a dog model of class III furcation defect and the regeneration of the cementum and the alveolar bone; the vertical axis plots the percent regeneration of the cementum or bone, and the horizontal axis plots the concentration of BDNF (μg/ml); the vertical lines on the bars in the graphs each represents the range of mean±standard deviation; * and ** mean the statistically significant differences at $p<0.05$ and $p<0.01$, respectively (in t-test); (A) shows the relationship with the percent regeneration of the cementum and (B) shows the relationship with the percent regeneration of the bone.
Figure 8:
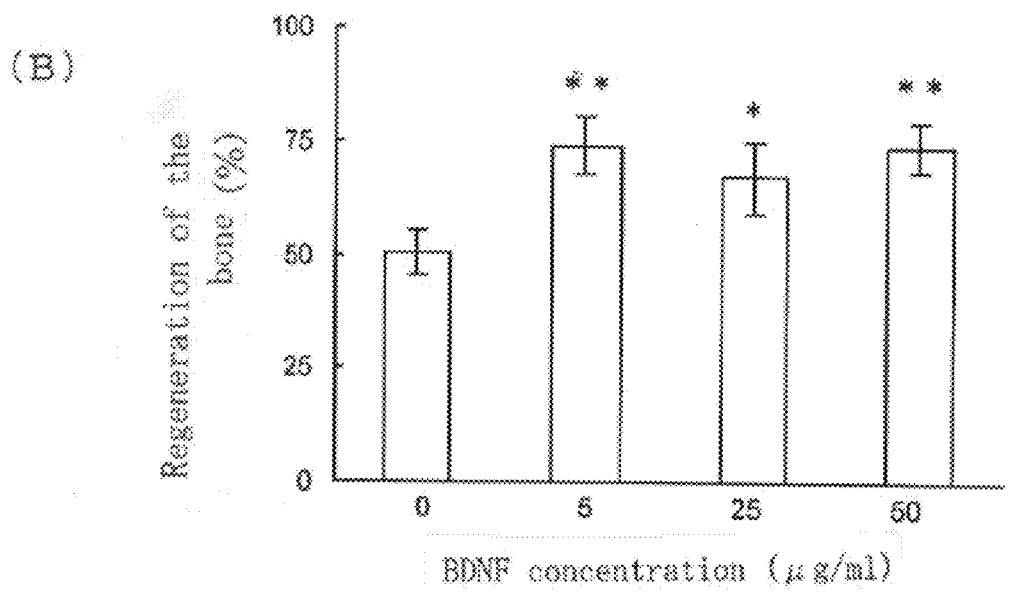
Figure 9A:
FIG. 9A is an optical microscopic view (×20) of a hematoxylin-eosin stained specimen of a bone defect at furcation and packed with a BDNF-free TERUPLUG R (CONTROL), prepared in Example 2.
Figure 9B:
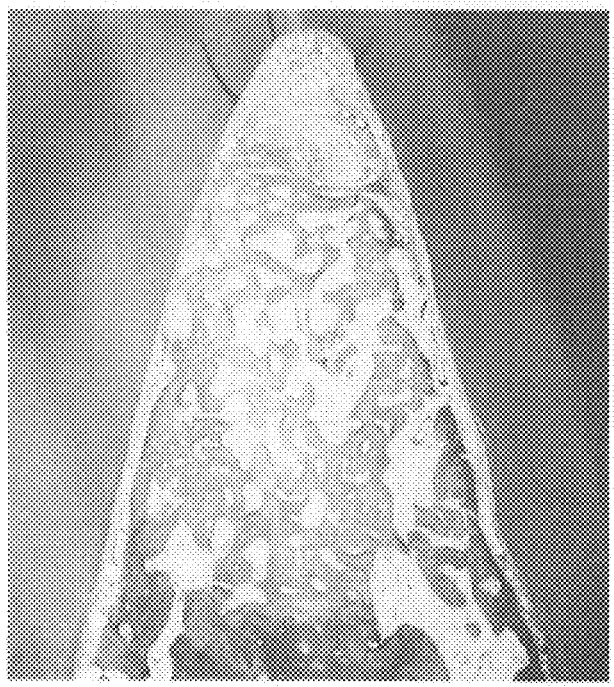
FIG. 9B is a microscopic view (×20) of a bone defect at furcation and packed with a transplant containing BDNF (5 μg/ml), prepared in Example 2.
Figure 10:
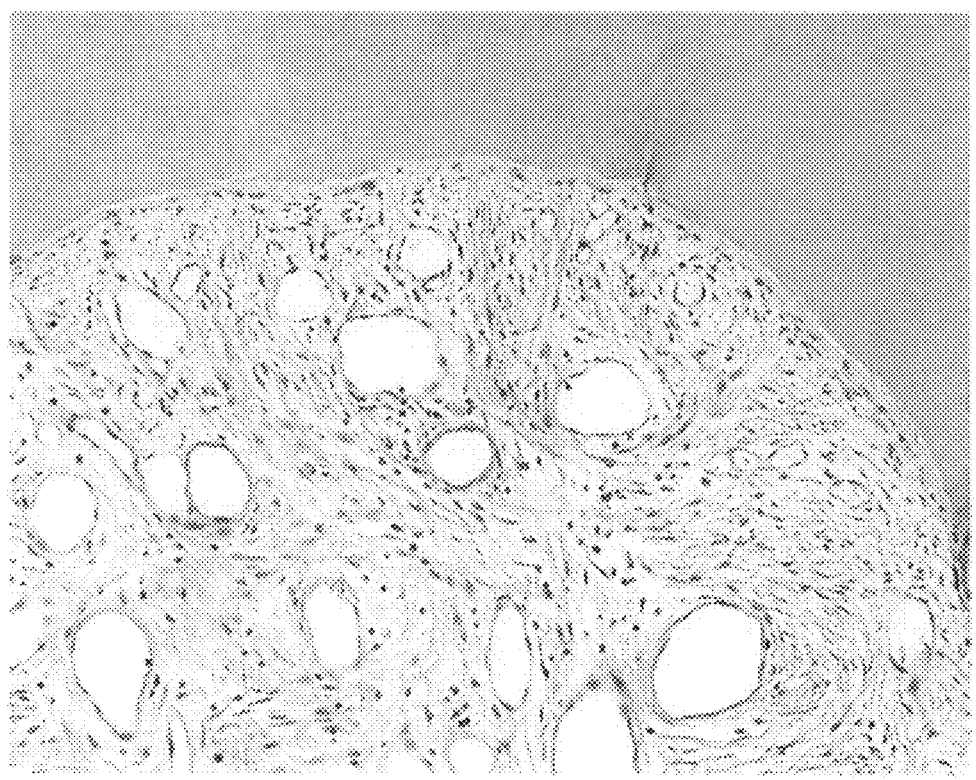
FIG. 10 is a partial enlarged view (×200) of the area right under the furcation shown in FIG. 9B; in that area and in almost all parts of the exposed dental root surface, cementum had been regenerated with collagen fibers embedded therein and there was no invasion of epithelium.

The results are shown in FIGS. 8, 9A, 9B and 10. FIG. 8 (A) shows the results of measuring the effect of BDNF on the regeneration of cementum; FIG. 8 (B) shows the results of measuring the effect of BDNF on the regeneration of alveolar bone. FIG. 9A shows a hematoxylin-eosin stained specimen of the bone defect at furcation which was not administered BDNF (control), and FIG. 9B is an optical microscopic view (×20) of the bone defect at furcation which was administered BDNF (packed with the transplant containing BDNF (5 μg/ml)). FIG. 10 is a partial enlarged view (×200) of the area just beneath the furcation in FIG. 9B.

As is clear from FIG. 8, when administered BDNF, the dog model of class III furcation defect had discernible regeneration of the cementum and the alveolar bone.

In the control specimen shown in FIG. 9A, some degree of regeneration was observed in the cementum, alveolar bone and periodontal ligament but it merely extended from the bottom of the bone defect to approximately one half the way toward the corona. In the defective area right under the furcation, there was no discernible regeneration of the cementum and the alveolar bone but there was observed an invasion of the epithelium; that area was practically occupied with a connective tissue mainly consisting of fibroblasts, collagen fibers and blood vessels.

In the specimen of the bone defect at furcation which was administered BDNF shown in FIGS. 9B and 10, the cementum was regenerated in almost all parts of the exposed dental root surface and there was no discernible invasion of the epithelium. In addition, a periodontal ligament maintaining a certain width was observed between the regenerated cementum and the regenerated alveolar bone.

Example 3

The effects of NGF on HPL cells and HGK were investigated.

(1) Expression of NGF and its Receptor in HPL Cells

By the same procedures as in Example 1(2) described above, total RNA was recovered from HPL cells and purified. With the obtained total RNA being used as a sample, the expression of mRNA for NGF and TrkA was measured by Northern blotting. GAPDH was used as a control.

Figure 11A:
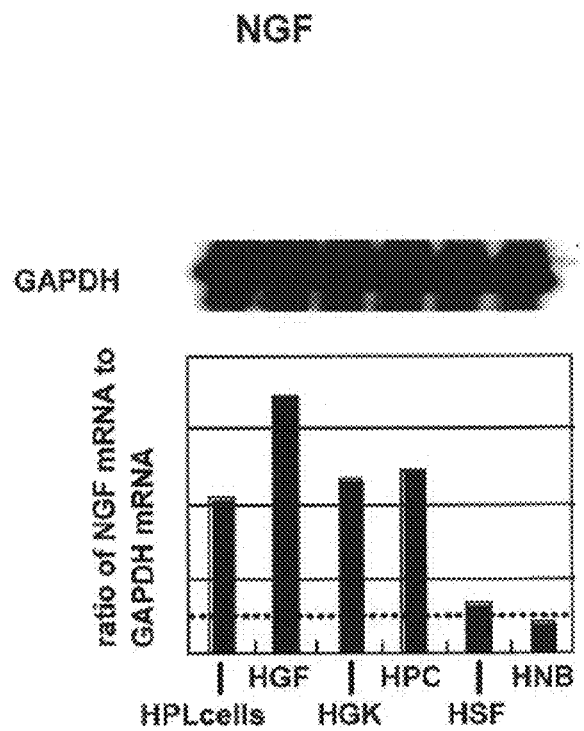
FIG. 11A shows by a radioactivity band and a bar graph the amount at which NGF mRNA was expressed in HPL cells; the vertical axis of the graph plots the amount of NGF mRNA expression relative to the amount of GAPDH mRNA expression; in the graph, HGF designates gingival fibroblasts, HPC, pulp cells, HSF, human skin fibroblasts, and HNB, human neuroblastoma cells.
Figure 11B:
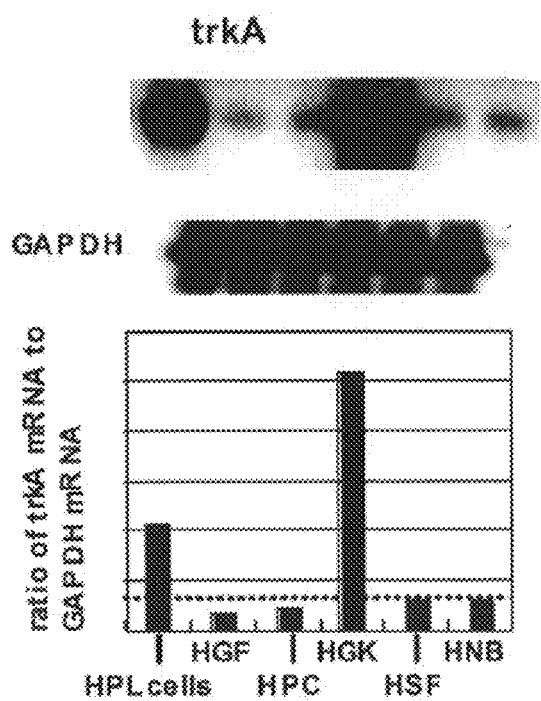
FIG. 11B shows by a radioactivity band and a bar graph the amount at which TrkA mRNA was expressed in HPL cells; the vertical axis of the graph plots the amount of TrkA mRNA expression relative to the amount of GAPDH mRNA expression; in the graph, HGF designates gingival fibroblasts, HPC, pulp cells, HSF, human skin fibroblasts, and HNB, human neuroblastoma cells.

The results are shown in FIGS. 11A and 11B. FIG. 11A shows the expression of mRNA for NGF, and FIG. 11B shows the expression of mRNA for TrkA. As is clear from the Figures, it was confirmed that mRNA of NGF and mRNA of TrkA had been expressed in the HPL cells.

(2) Expression of Bone-related Proteins in HPL Cells

The effects of NGF on the expression of mRNA for bone-related proteins in HPL cells were investigated.

HPL cells were treated by the same procedure as in Example 1(4)(i) except that BDNF was replaced by NGF (Recombinant Human NGF, R&D System, Minneapolis, USA) at final concentrations of 0, 5, 10, 25, 50 and 100 ng/ml. The amounts in which the NGF-treated HPL cells expressed the mRNAs of ALPase, BMP-2 and OPN were measured by the same method as in Example 1(4)(i).

Figure 12:
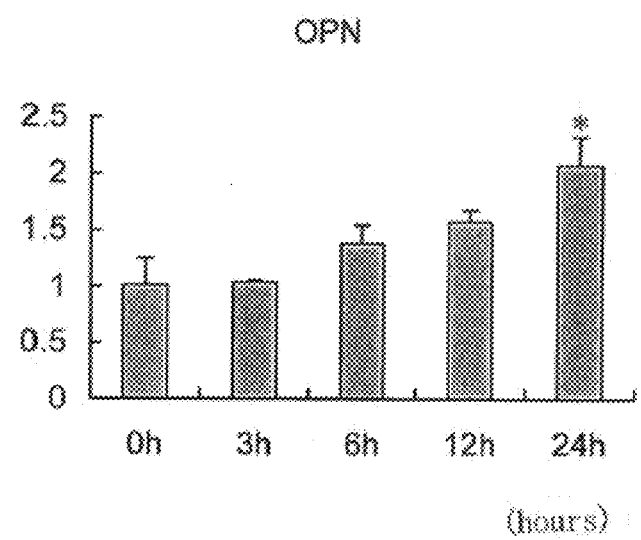
FIG. 12 shows by means of a bar graph the effects of NGF on the amount of OPN mRNA expression in HPL cells; (A) is a graph showing the results of measuring the time course effect of NGF; the vertical axis of the graph plots the relative amount of OPN mRNA expression for each exposure time of NGF, with the amount of mRNA expression for exposure time zero being taken as unity; the horizontal axis of the graph plots the exposure time of NGF; all cells were treated with NGF at a final concentration of 100 ng/ml; (B) is a graph showing the results of measuring the dose effect; the vertical axis of the graph plots the relative amount of OPN mRNA expression at each concentration of NGF, with the amount of mRNA expression at zero concentration being taken as unity; the horizontal axis of the graph plots the concentration of NGF (ng/ml); NGF exposure time was 24 hours in all cases.
Figure 12:
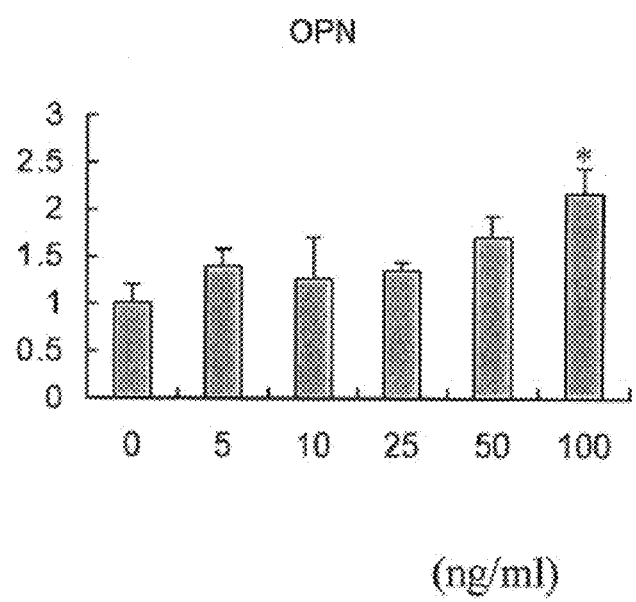
Figure 13:
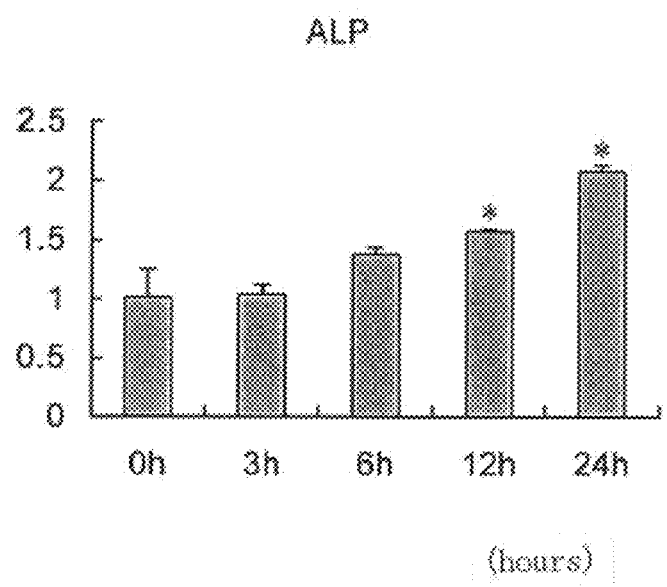
FIG. 13 shows by means of a bar graph the effects of NGF on the amount of ALPase mRNA expression in HPL cells; (A) is a graph showing the results of measuring the time course effect of NGF; the vertical axis of the graph plots the relative amount of ALPase mRNA expression for each exposure time of NGF, with the amount of ALPase mRNA expression for exposure time zero being taken as unity; the horizontal axis of the graph plots the exposure time of NGF; (B) is a graph showing the results of measuring the dose effect; the vertical axis of the graph plots the relative amount of ALPase mRNA expression at each concentration of NGF, with the amount of ALPase mRNA expression at zero concentration being taken as unity; the horizontal axis of the graph plots the concentration of NGF (ng/ml).
Figure 13:
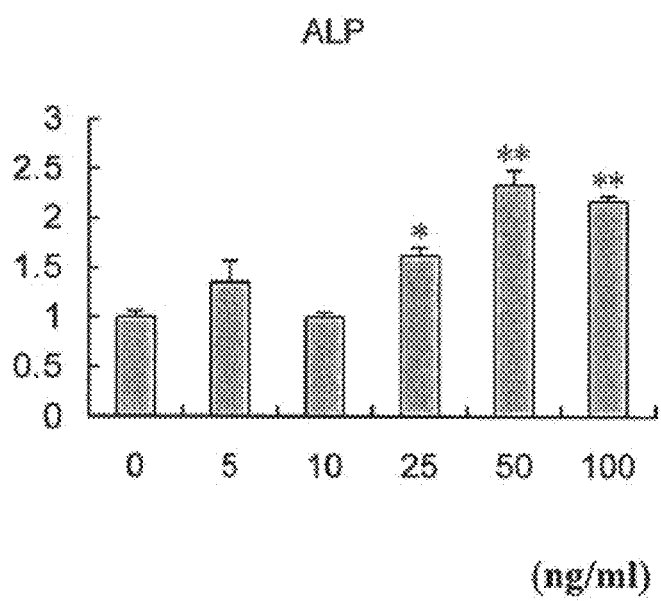
Figure 14:
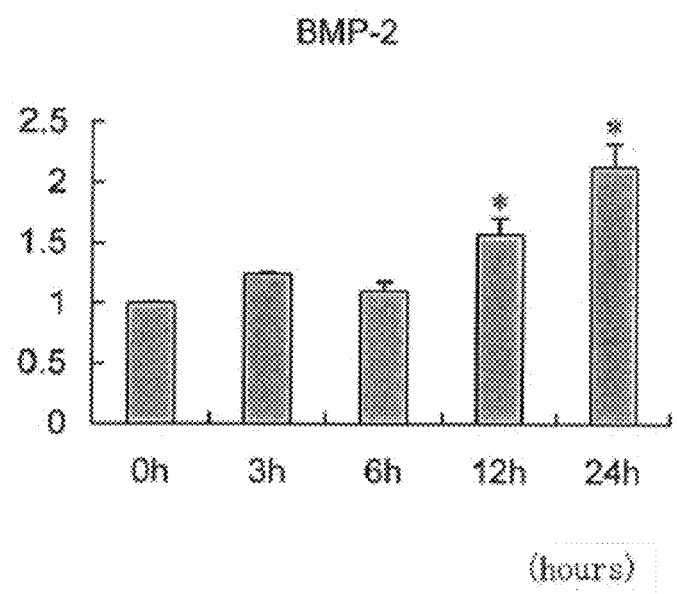
FIG. 14 shows by means of a bar graph the effects of NGF on the amount of BMP-2 mRNA expression in HPL cells; (A) is a graph showing the results of measuring the time course effect of NGF; the vertical axis of the graph plots the relative amount of BMP-2 mRNA expression for each exposure time of NGF, with the amount of BMP-2 mRNA expression for exposure time zero being taken as unity; the horizontal axis of the graph plots the exposure time of NGF; (B) is a graph showing the results of measuring the dose effect; the vertical axis of the graph plots the relative amount of BMP-2 mRNA expression at each concentration of NGF, with the amount of BMP-2 mRNA expression at zero concentration being taken as unity; the horizontal axis of the graph plots the concentration of NGF (ng/ml).
Figure 14:
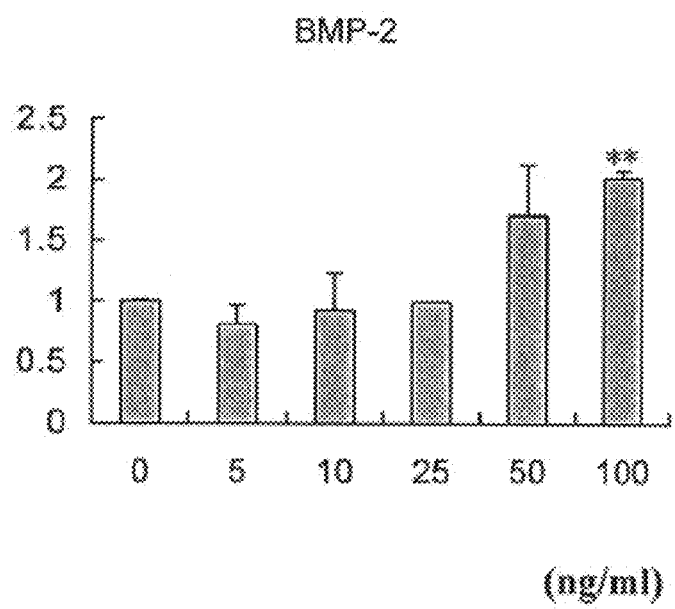

FIGS. 12, 13 and 14 show the results of measuring the time course effect and the dose effect of NGF on the expression of mRNA for OPN, ALPase and BMP-2, respectively. In each graph, * and ** mean $p<0.05$ and $p<0.01$, respectively. Testing was done by t-test.

As is clear from FIGS. 12, 13 and 14, NGF increased the expression of mRNA for ALPase, BMP-2 and OPN in both a dose- and a time-dependent manner.

(3) Proliferation of HPL Cells and HGK

The effects of NGF on the ability of HPL cells and HGK to synthesize DNA were measured.

HPL cells and HGK were treated by the same method as in Example 1(5) except that BDNF was replaced by NGF at final concentrations of 0, 5, 10, 25, 50 and 100 ng/ml. The ability of the NGF-treated HPL cells and HGK to synthesize DNA was measured by the same method as in Example 1(5).

Figure 15:
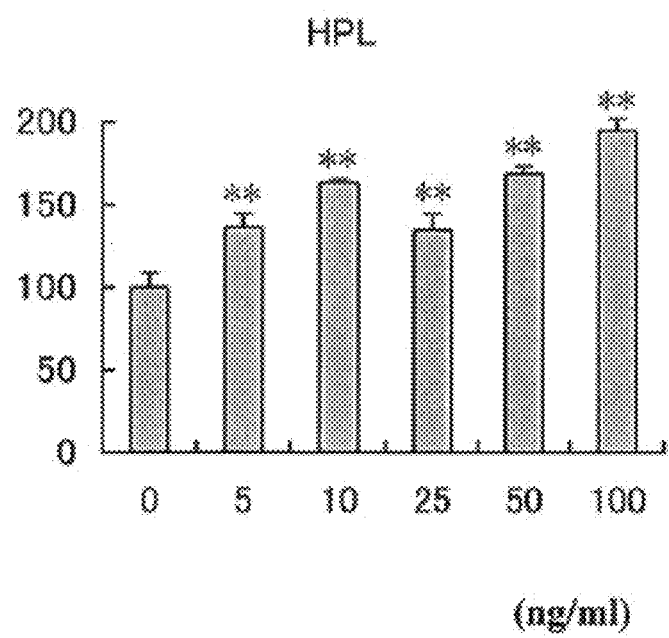
FIG. 15 shows by means of a bar graph the relationship between the dose at which NGF was administered and the ability of HPL cells and HGK to synthesize DNA; the respective concentrations of NGF were administered to HPL cells and HGK for 24 hours; the vertical axis of each graph plots the relative ability to synthesize DNA at each dose of NGF, with the ability to synthesize DNA at zero concentration of NGF being taken as 100; the horizontal axis plots the concentration of NGF (ng/ml); (A) shows the ability to synthesize DNA in HPL cells, and (B) shows the ability to synthesize DNA in HGK.
Figure 15:
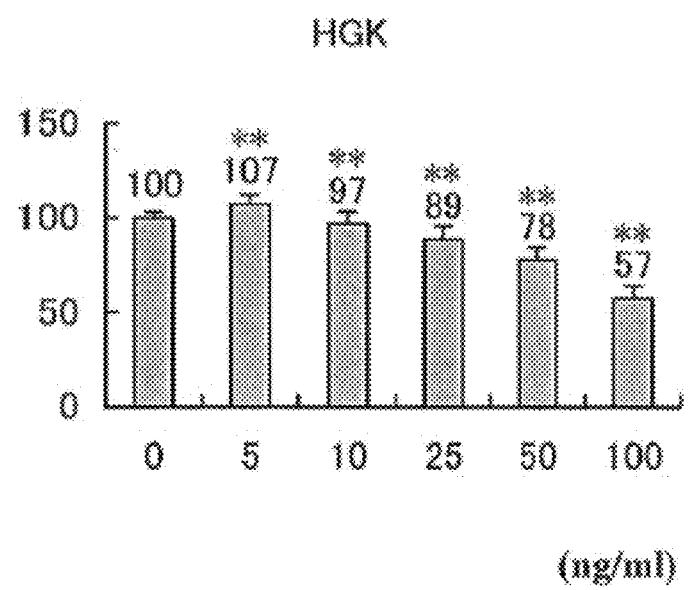

The results are shown in FIG. 15. The exposure time of NGF was 24 hours in all runs; (A) shows the effects on HPL cells, and (B) shows the effects on HGK. In each graph, * and ** mean $p<0.05$ and $p<0.01$, respectively. Testing was done by t-test.

As is clear from FIG. 15, NGF enhanced the DNA synthesizing ability of HPL cells but lowered the DNA synthesizing ability of HGK.

Example 4

The effects of NT-3 on HPL cells and HGK were investigated.

(1) Expression of NT-3 and its Receptor in HPL Cells

By the same procedures as in Example 1(2) described above, total RNA was recovered from HPL cells and purified. With the obtained total RNA being used as a sample, the expression of mRNA for NT-3 and TrkC was measured by Northern blotting. GAPDH was used as a control.

Figure 16A:
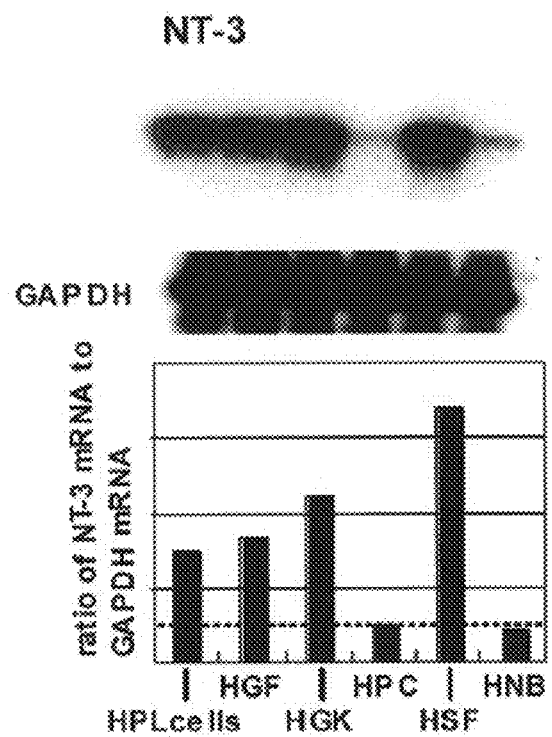
FIG. 16A shows by a radioactivity band and a bar graph the amount of NT-3 mRNA expression in HPL cells; the vertical axis of the graph plots the relative amount of NT-3 mRNA expression, with the amount of GAPDH mRNA expression being taken as unity; in the graph, HGF designates gingival fibroblasts, HPC, pulp cells, HSF, human skin fibroblasts, and HNB, human neuroblastoma cells.
Figure 16B:
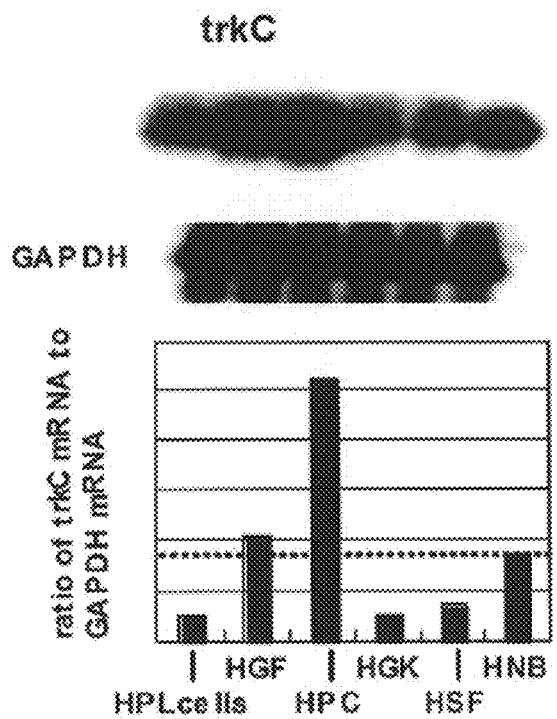
FIG. 16B shows by a radioactivity band and a bar graph the amount of TrkC mRNA expression in HPL cells; the vertical axis of the graph plots the relative amount of TrkC mRNA expression, with the amount of GAPDH mRNA expression being taken as unity; in the graph, HGF designates gingival fibroblasts, HPC, pulp cells, HSF, human skin fibroblasts, and HNB, human neuroblastoma cells.

The results are shown in FIGS. 16A and 16B. FIG. 16A shows the expression of mRNA for NT-3, and FIG. 16B shows the expression of mRNA for TrkC. As is clear from the Figures, it was confirmed that mRNA of NT-3 and mRNA of TrkC had been expressed in the HPL cells.

(2) Expression of Bone-Related Protein in HPL Cells

The effects of NT-3 on the ALPase activity in HPL cells were investigated.

HPL cells were treated by the same procedure as in Example 1(3)(i) except that BDNF was replaced by NT-3 (Recombinant Human NT-3, R&D System, Minneapolis, USA) at final concentrations of 0, 1, 10 and 50 ng/ml, and their ALPase activity was quantitated in accordance with the Bessey-Lowry method. Stated more specifically, the NT-3 treated HPL cells were washed three times with a phosphate buffer and after adding 10 mM Tris-HCl buffer, the cells were sonicated under ice cooling to prepare a sample. The ALPase activity in the sample was measured with an ALPase measuring kit (Wako Pure Chemical Industries, Ltd.) using p-nitrophenyl phosphate as a substrate.

Figure 17:
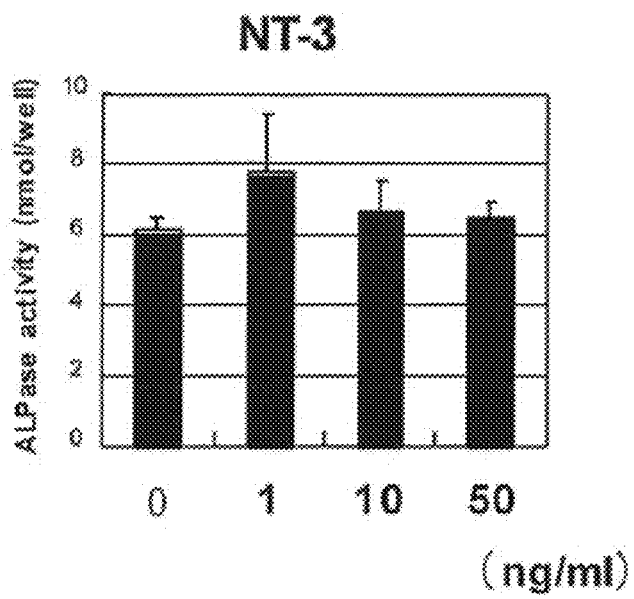
FIG. 17 is a bar graph showing the relationship between the dose at which NT-3 was administered and the ALPase activity in HPL cells; the vertical axis of the graph plots the ALPase activity (nmol/well) and the horizontal axis plots the concentration of NT-3 (ng/ml).

FIG. 17 shows the results of measuring the dose effect of NT-3 on ALPase activity. The exposure time of NT-3 was 24 hours in all runs. As is clear from the Figure, NT-3 did not have much effect on ALPase activity.

(3) Proliferation of HPL Cells

HPL cells separated by the same method as in Example 1(1) were treated by the same method as in Example 1(5) except that BDNF was replaced by NT-3 at final concentrations of 0, 1, 5, 10, 50 and 100 ng/ml. Their ability to synthesize DNA was measured by the same method as in Example 1(5).

Figure 18:
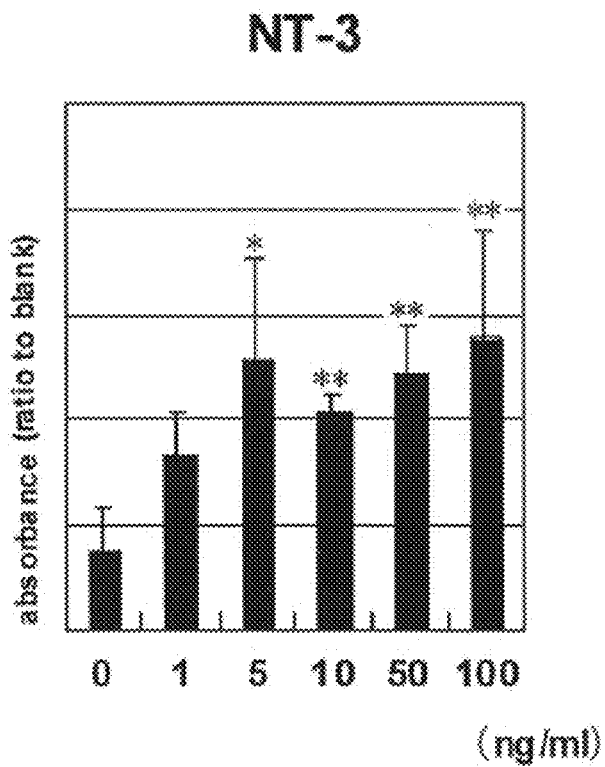
FIG. 18 is a bar graph showing the relationship between the dose at which NT-3 was administered and the ability to synthesize DNA in HPL cells; the vertical axis of the graph compares by absorbance the ability of HPL cells to synthesize DNA at various concentrations of NT-3; and the horizontal axis plots the concentration of NT-3 (ng/ml).

The results are shown in FIG. 18. The exposure time of NT-3 was 24 hours in all runs. In the graph, * and ** mean $p<0.05$ and $p<0.01$, respectively. Testing was done by t-test. As is clear from the Figure, NT-3 enhanced the DNA synthesizing ability of HPL cells.

Example 5

The expression of mRNA for bone-related proteins by NT-4/5 in human periodontal ligament cells (HPL cells) was investigated.

(1) Treatment of HPL Cells with NT-4/5

The HPL cells obtained in Example 1(1)(i) above were cultivated on Petri dishes of 60 mm diameter (SUMILON CELTITE C-1) coated with bovine type I collagen at 37° C. in a 5% $CO_2$ gas phase for 13 days at a density of $3.5 \times 10^5$ cells per Petri dish using medium B (50 μg/ml). The medium was changed once every two days. At 0, 3, 6, 12 and 24 hours before the end of cultivation at day 14, the cells were washed twice with DMEM and medium was changed for medium D containing NT-4/5 (R&D) at a final concentration of 50 ng/ml.

(2) Expression of mRNA in HPL Cells

HPL cells were treated with NT-4/5 at a final concentration of 50 ng/ml by the same procedure as described in (3)(i) above and total RNA was extracted from the thus treated HPL cells with ISOGEN and purified. The expression of mRNA for ALPase, BMP-2, OPN, osteocalcin (OCN), BMP-7, BMP-4 and OPG was quantitatively analyzed by monitoring the process of generation of PCR products in real-time using ABI PRISM 7700 (Applied Biosystems, Tokyo) (real-time PCR method). GAPDH was used as a control.

Figure 19A:
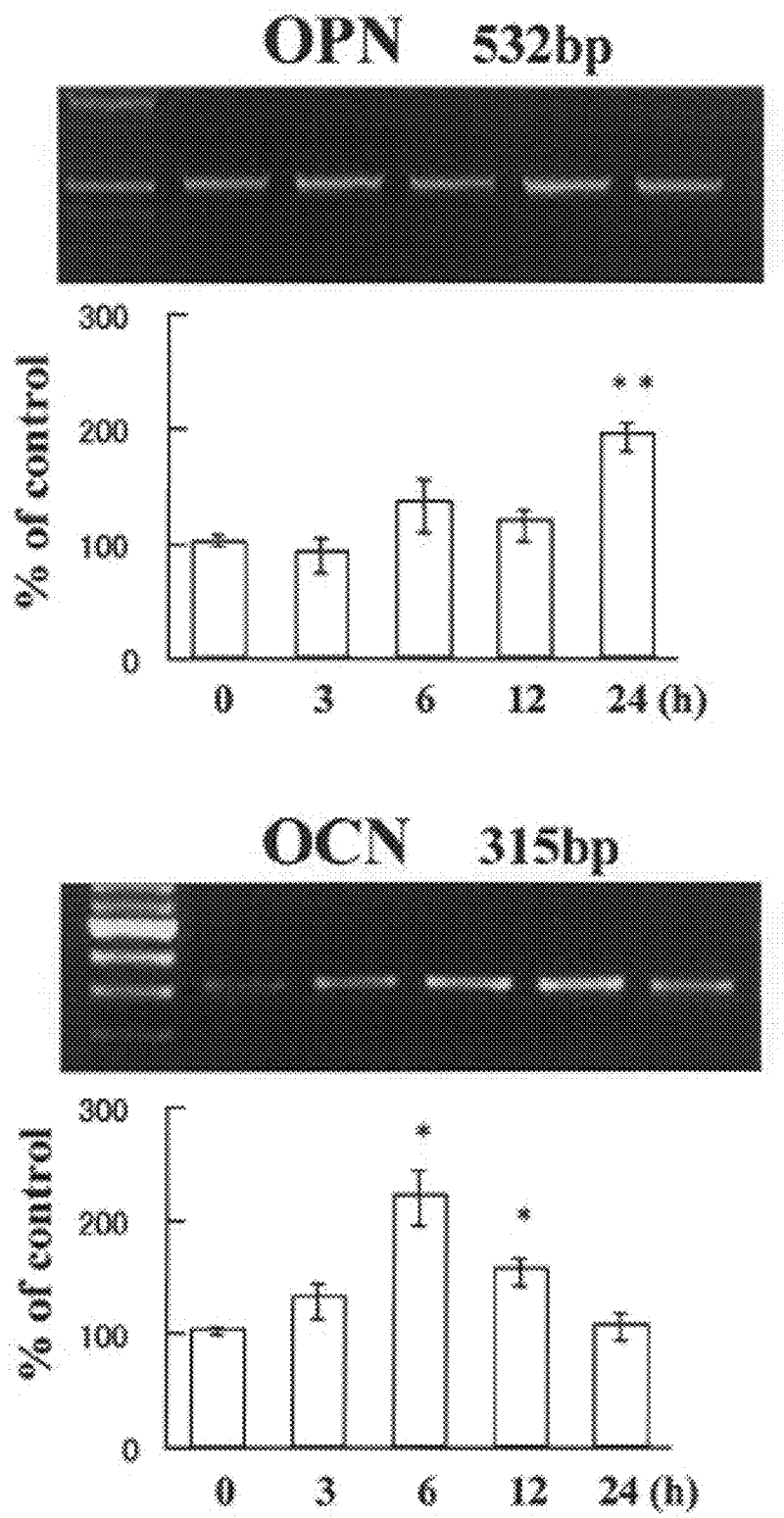
FIG. 19A shows by an electrophoretogram and a bar graph the relationship between the exposure time of NT-4/5 and the amounts in which mRNAs of OPN and OCN were expressed in HPL cells; the final concentration of NT-4/5 was adjusted at 50 ng/ml; the lane at the left end of each electrophoretogram is the marker; the vertical axis of each graph plots the relative amount of mRNA expression for exposure time, with the amount of mRNA expression for exposure time zero being taken as 100; the horizontal axis of each graph plots the exposure time of NT-4/5; the vertical lines on the bars in each graph represent the range of mean±standard deviation; in each graph, * and ** mean $p<0.05$ and $p<0.01$, respectively (statistical testing by t-test).
Figure 19B:
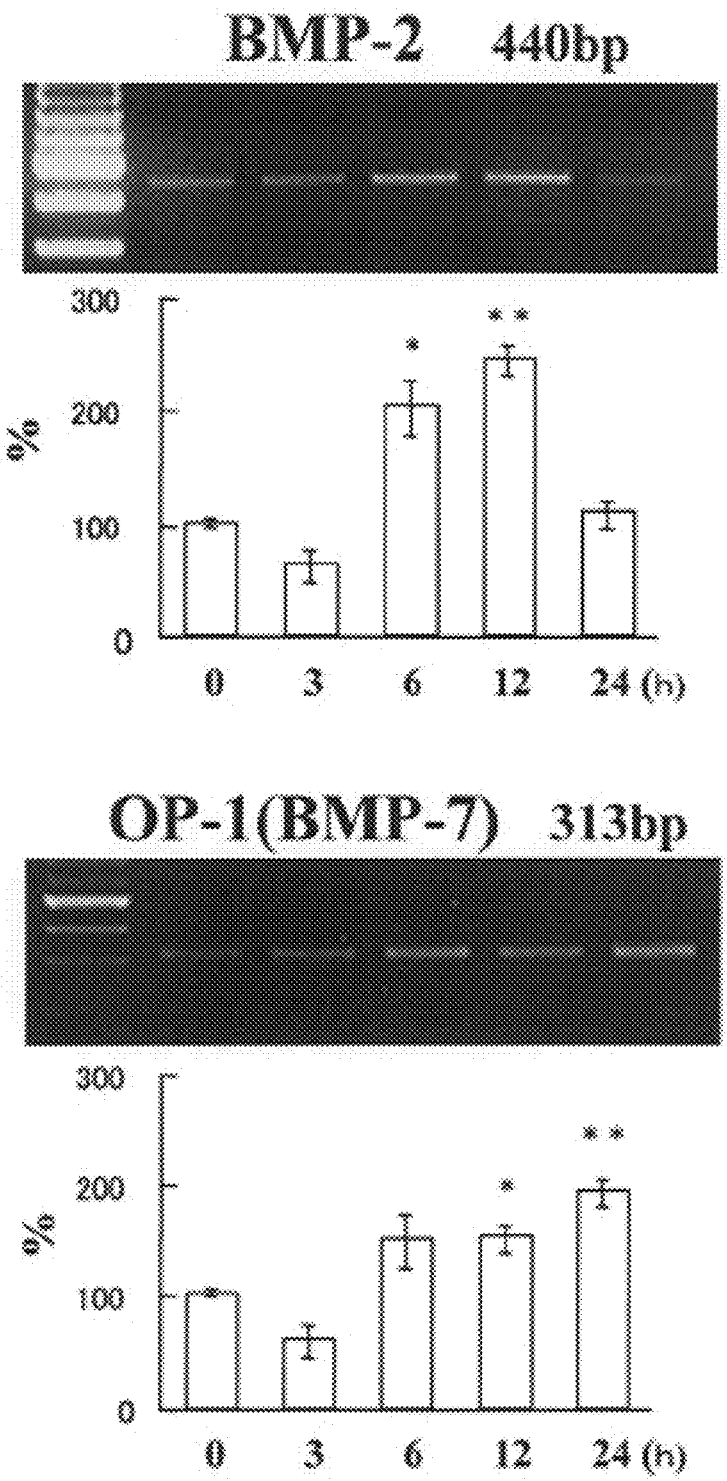
FIG. 19B shows by an electrophoretogram and a bar graph the relationship between the exposure time of NT-4/5 and the amounts in which mRNAs of BMP-2 and BMP-7 were expressed in HPL cells; the final concentration of NT-4/5 was adjusted at 50 ng/ml; the lane at the left end of each electrophoretogram is the marker; the vertical axis of each graph plots the relative amount of mRNA expression for each exposure time, with the amount of mRNA expression for exposure time zero being taken as 100; the horizontal axis of each graph plots the exposure time of NT-4/5; the vertical lines on the bars in each graph represent the range of mean±standard deviation; in each graph, * and ** mean $p<0.05$ and $p<0.01$, respectively (statistical testing by t-test).
Figure 19C:
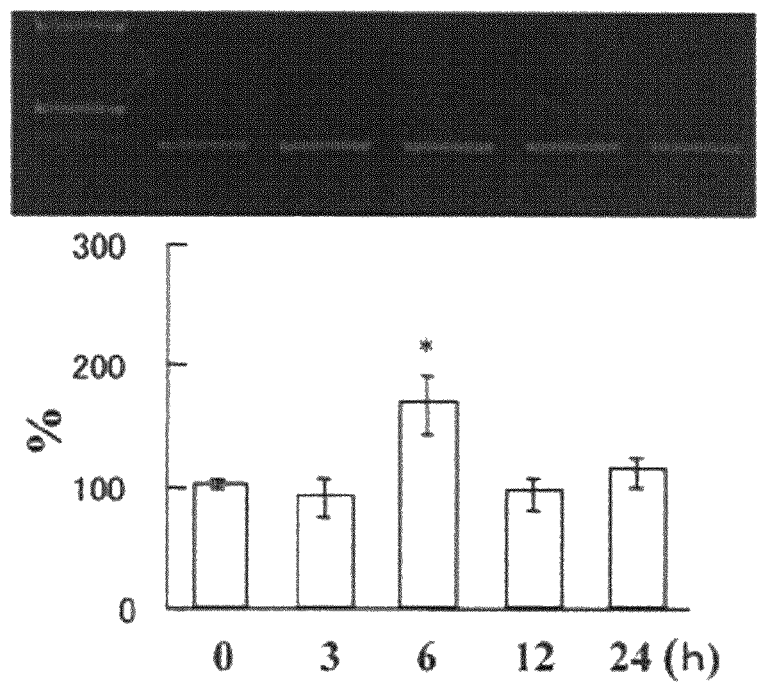
FIG. 19C shows by an electrophoretogram and a bar graph the relationship between the exposure time of NT-4/5 and the amount in which mRNA of ALPase was expressed in HPL cells; it also shows by an electrophoretogram the relationship between the exposure time of NT-4/5 and the amount of GAPDH expression; the final concentration of NT-4/5 was adjusted at 50 ng/ml; the lane at the left end of each electrophoretogram is the marker; the vertical axis of the graph plots the relative amount of mRNA expression for each exposure time, with the amount of mRNA expression for exposure time zero being taken as 100; the horizontal axis of the graph plots the exposure time of NT-4/5; the vertical lines on the bars in the graph represent the range of mean±standard deviation; * means $p<0.05$ (statistical testing by t-test).
Figure 19C:
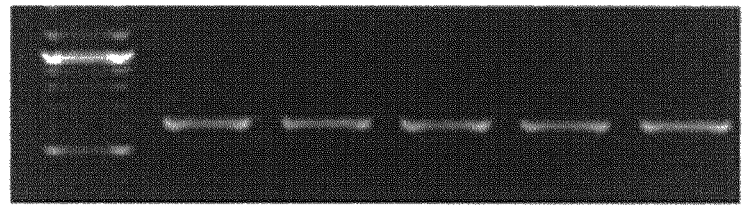
Figure 20:
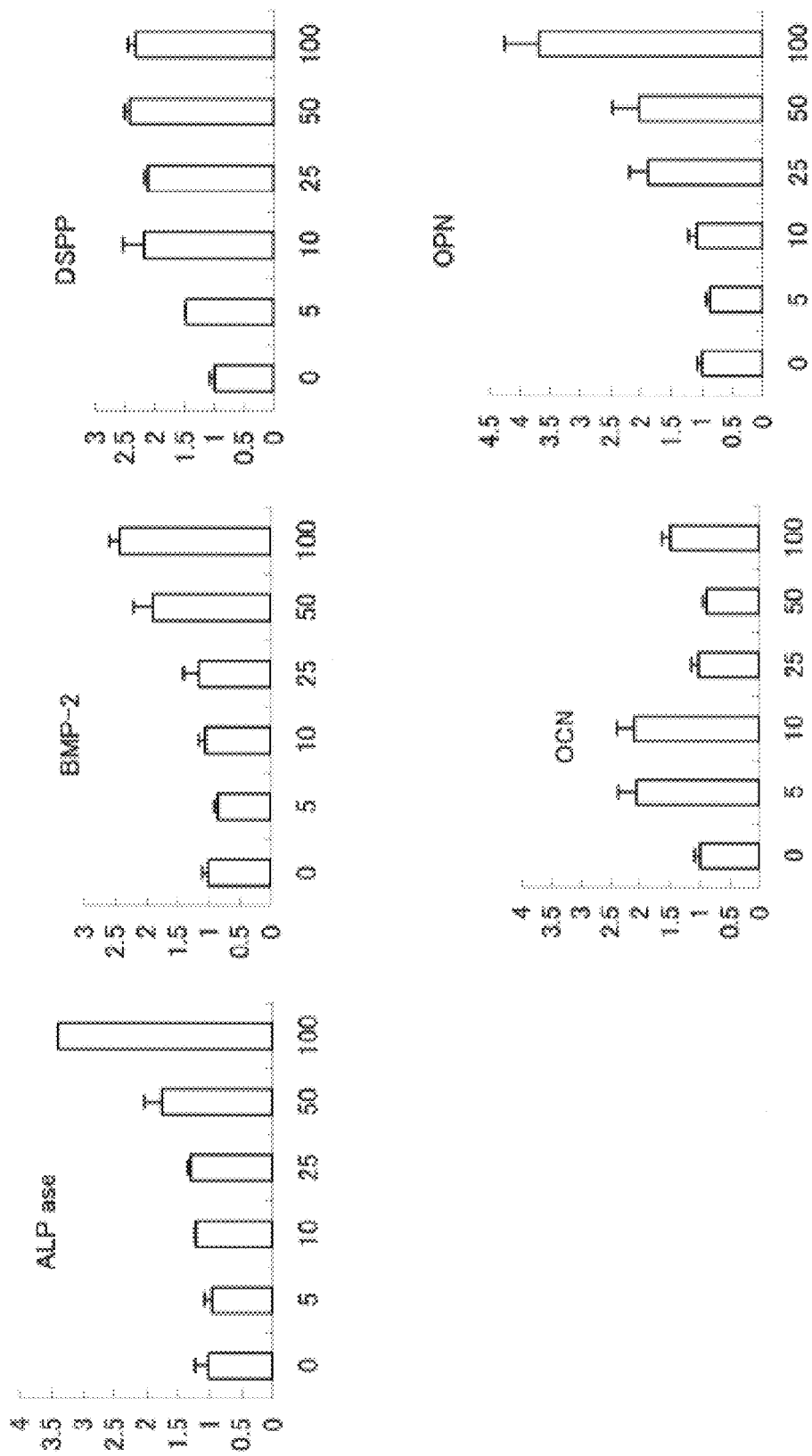
FIG. 20 is a set of graphs showing the results of measuring the dose effect of NGF on the expression of mRNA for various bone-related proteins (ALPase, BMP-2, DSPP, OPN, and OCN) in HP cells; the exposure time of NGP was 24 hours; the vertical axis of each graph plots the relative amount of mRNA expression at each concentration of NGF, with the amount of mRNA expression at zero concentration being taken as unity; the horizontal axis plots the concentration of NGF (ng/ml); the vertical lines on the bars in each graph represent the range of mean±standard deviation.
Figure 21:
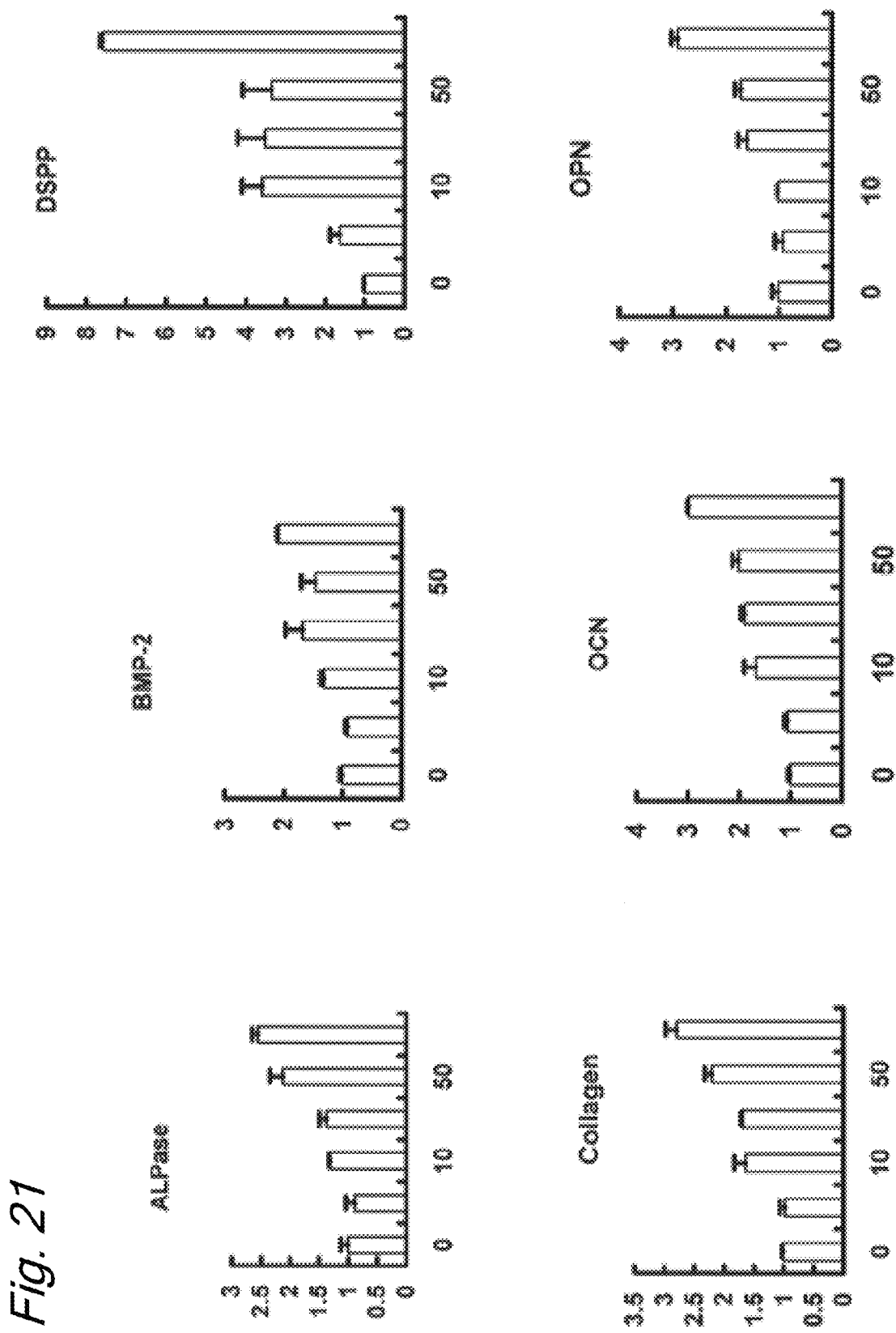
FIG. 21 is a set of graphs showing the results of measuring the dose effect of BDNF on the expression of mRNA for various bone-related proteins (ALPase, BMP-2, DSPP, type I collagen, OPN, and OCN) in HP cells; the vertical axis of each graph plots the relative amount of mRNA expression at each concentration of BDNF, with the amount of mRNA expression at zero concentration being taken as unity; the horizontal axis plots the concentration of BDNF (ng/ml); the vertical lines on the bars in each graph represent the range of mean±standard deviation.
Figure 22:
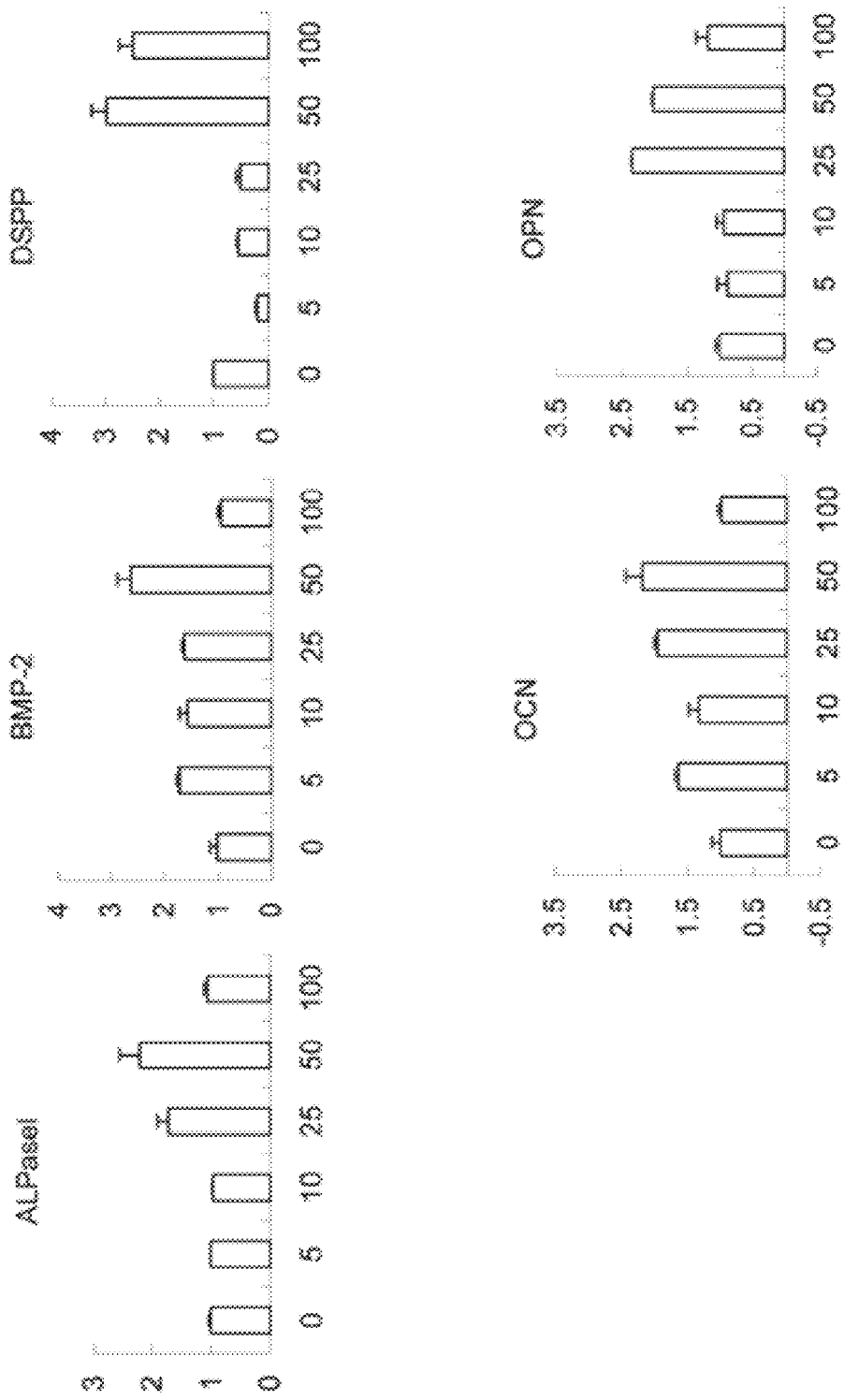
FIG. 22 is a set of graphs showing the results of measuring the dose effect of NT-3 on the expression of mRNA for various bone-related proteins (ALPase, BMP-2, DSPP, OPN, and OCN) in HP cells; the vertical axis of each graph plots the relative amount of mRNA expression at each concentration of NT-3, with the amount of mRNA expression at zero concentration being taken as unity; the horizontal axis plots the concentration of NT-3 (ng/ml); the vertical lines on the bars in each graph represent the range of mean±standard deviation.
Figure 23:
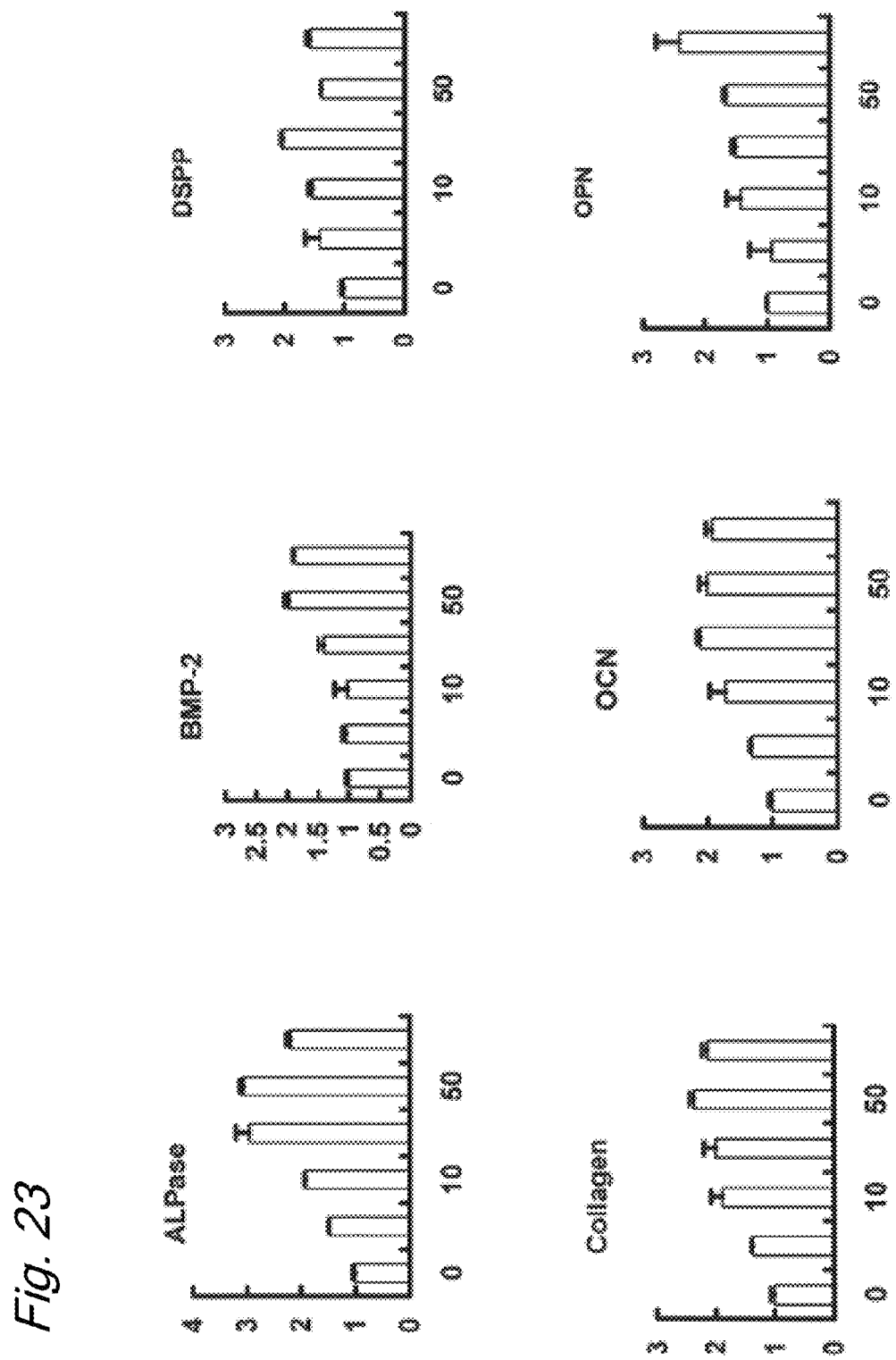
FIG. 23 is a set of graphs showing the results of measuring the dose effect of NT-4/5 on the expression of mRNA for various bone-related proteins (ALPase, BMP-2, DSPP, type I collagen, OPN, and OCN) in HP cells; the vertical axis of each graph plots the relative amount of mRNA expression at each concentration of NT-4/5, with the amount of mRNA expression at zero concentration being taken as unity; the horizontal axis plots the concentration of NT-4/5 (ng/ml); the vertical lines on the bars in each graph represent the range of mean±standard deviation.

The results of measuring the time course effect of NT-4/5 on the expression of mRNA for the respective bone-related proteins are shown in FIGS. 19A, 19B and 19C. In each graph, * and ** mean $p<0.05$ and $p<0.01$, respectively (statistical testing by t-test). As is clear from those Figures, NT-4/5 enhanced the expression of mRNA for OPN, BMP-2, ALPase, OCN and BMP-7 in HPL cells but had no effect on the expression of mRNA for BMP-4 and OPG (data not shown).

Example 6

The effects of NGF, BDNF, NT-3 and NT-4/5 on human pulp cells (HP cells) were investigated.

(1) Cells Used

Healthy dental pulp that had been obtained for the sake of convenience in dental pulp removal was shredded. The shredded tissue was attached to a cell culture Petri dish of 60 mm diameter (CORNING, N.Y.) and cultivated on medium A at 37° C. in a 5% $CO_2$ gas phase. HP cells in culture at passage 4-8 were used for the following experiment.

(2) Treatment of the Cells with NGF, BDNF, NT-3 and NT-4/5

NGF, BDNF, NT-3 or NT-4/5 was added to medium D at final concentrations of 0, 5, 10, 25, 50 and 100 ng/ml to prepare culture mediums containing those neurotrophic factors at the indicated concentrations. The HP cells obtained in (1) above were cultivated on Petri dishes of 60 mm diameter (SUMILON CELTITE C-1) coated with bovine type I collagen at 37° C. in a 5% $CO_2$ gas phase for 13 days at a density of $3.5 \times 10^5$ cells per Petri dish, using medium B. The medium was changed once every two days. Twenty-four hours before the end of cultivation at day 14, the cells were washed twice with DMEM and medium was changed for either one of the neurotrophic factors containing culture mediums.

(3) Expression of mRNA in HP Cells

From the HP cells of (1) above treated with NGF, BDNF, NT-3 or NT-4/5 at the indicated concentrations for 24 hours, total RNA was extracted using ISOGEN and purified. The expression of mRNA for ALPase, BMP-2, dentin sialophosphoprotein (DSPP), type I collagen, OPN and OCN was quantitatively analyzed by monitoring the process of generation of PCR products in real-time using ABI PRISM 7700 (Applied Biosystems, Tokyo) (real-time PCR method). GAPDH was used as a control.

The results of measuring the dose effects of NGF, BDNF, NT-3 and NT-4/5 on the expression of mRNA for the respective bone-related proteins are shown in FIGS. 20, 21, 22 and 23, respectively. As is clear from those Figures, NGF, BDNF, NT-3 and NT-4/5 enhanced the expression of mRNA for ALPase, BMP-2, DSPP, OPN and OCN in HP cells. BDNF and NT-4/5 also enhanced the expression of mRNA for type I collagen.

(4) Proliferation of HP Cells

The effects of NGF, BDNF, NT-3 and NT-4/5 on the ability of HP cells to synthesize DNA were measured by ELISA using a Cell Proliferation ELISA System, Version 2 (Amersham Pharmacia Biotech).

To medium B supplemented with 0.3% FBS instead of 10% FBS, each of NGF, BDNF, NT-3 and NT-4/5 was added at final concentrations of 0, 5, 10, 25, 50 and 100 ng/ml to prepare culture mediums containing those neurotrophic factors.

The HP cells obtained in (1) above were seeded on a 96-well plate (SUMILON CELTITE C-1 Plate 96F) coated with bovine type I collagen at a density of $5 \times 10^3$ cells/well and cultivated for 10 days using medium B. The cells were washed twice with DMEM and cultivated for 24 hours on medium B, except that it was supplemented with 0.3% FBS instead of 10% FBS; thereafter, the medium was changed for either one of the above-described neurotrophic factors containing culture mediums, and culture was continued for an additional 24 hours. Two hours before the end of the culture (viz. 22 hours after the addition of the neurotrophic factors), bromodeoxyuridine (BrdU) was added to each well at a concentration of 10 ng/ml so that it was incorporated into the cells. Culture was performed at 37° C. in a 5% $CO_2$ gas phase. After the end of culture, the HP cells were fixed and then blocking was performed; a peroxidase labeled anti-BrdU antibody was allowed to act on the cells at room temperature for 2 hours and a TMB (3,3',5,5'-tetramethylbenzidine) substrate was added to measure the absorbance at a wavelength of 450 nm with an absorptiometer (MICRO PLATE READER, TOSOH).

Figure 24:
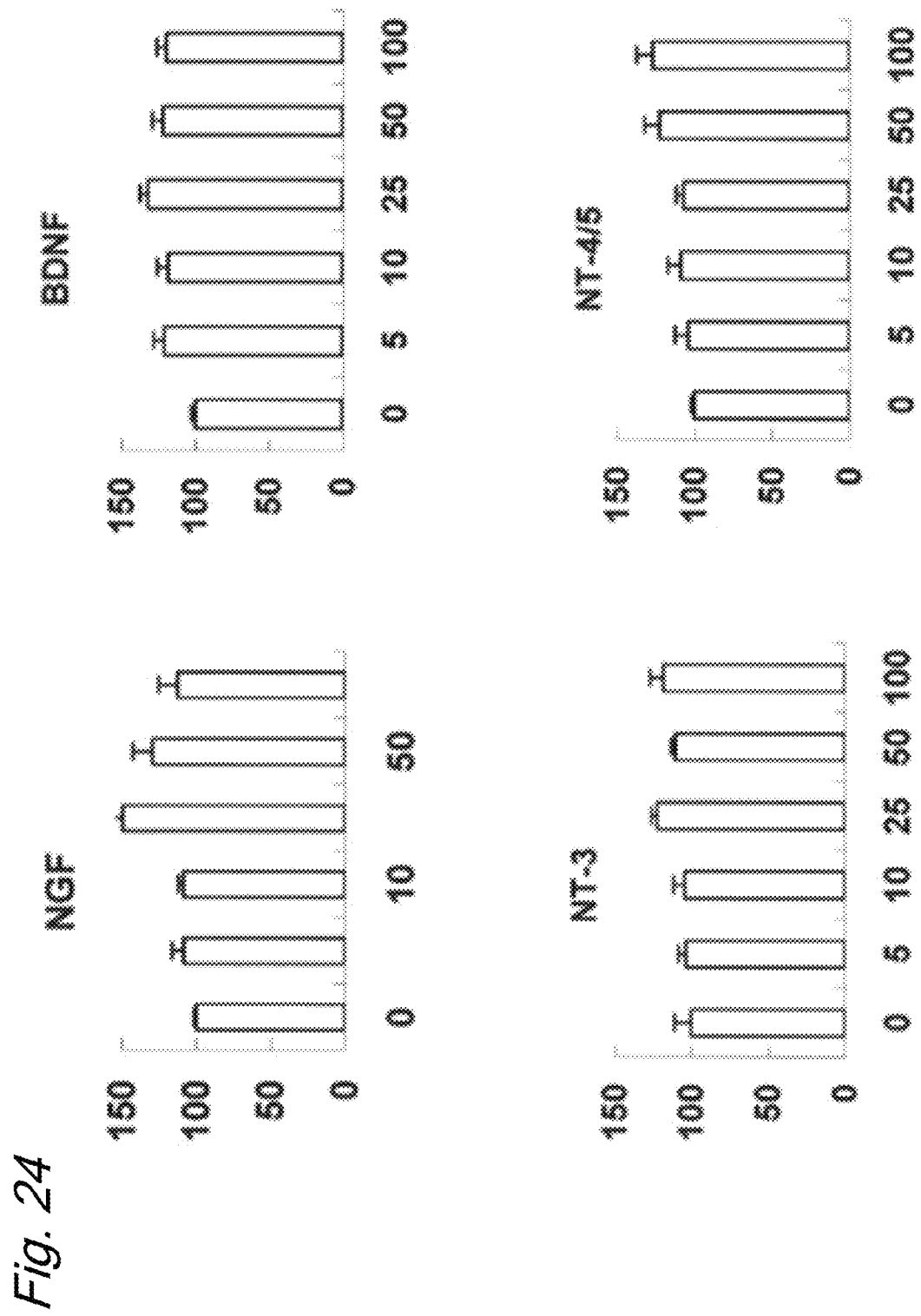
FIG. 24 is a set of bar graphs showing the relationship between the dose at which various neurotrophic factors (NGF, BDNF, NT-3, and NT-4/5) were administered and the ability of HP cells to synthesize DNA; the respective concentrations of the neurotrophic factors were allowed to act on HP cells for 24 hours; the vertical axis of each graph plots the relative absorbance at each dose of a neurotrophic factor, with the absorbance without a neurotrophic factor (i.e. at zero concentration of a neurotrophic factor) being taken as 100; the horizontal axis plots the concentration of each neurotrophic factor (ng/ml); the vertical lines on the bars in each graph represent the range of mean±standard deviation.
Figure 25A:
FIG. 25A shows by an electrophoretogram and a bar graph the relationship between the exposure time of NGF and the amount of ALPase mRNA expression in HMS cells; it also shows an electrophoretogram depicting the relationship with the amount of GAPDH mRNA expression as control; HMS cells were all treated with NGF at a final concentration of 100 ng/ml; the lane at the left end of each electrophoretogram is the marker; the vertical axis of the graph plots the percentage of the amount of mRNA expression for each exposure time of NGF, with the amount of mRNA expression for exposure time zero being taken as 100%; the horizontal axis plots the exposure time of NGF.
Figure 25A:
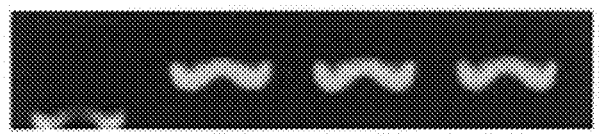
Figure 25A:
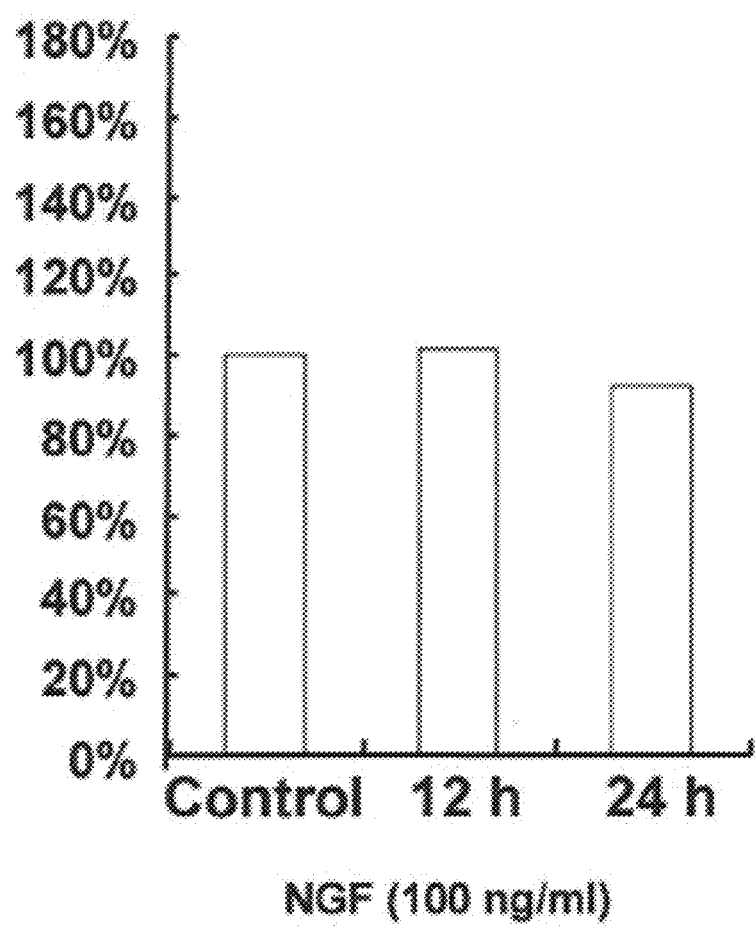
Figure 25B:
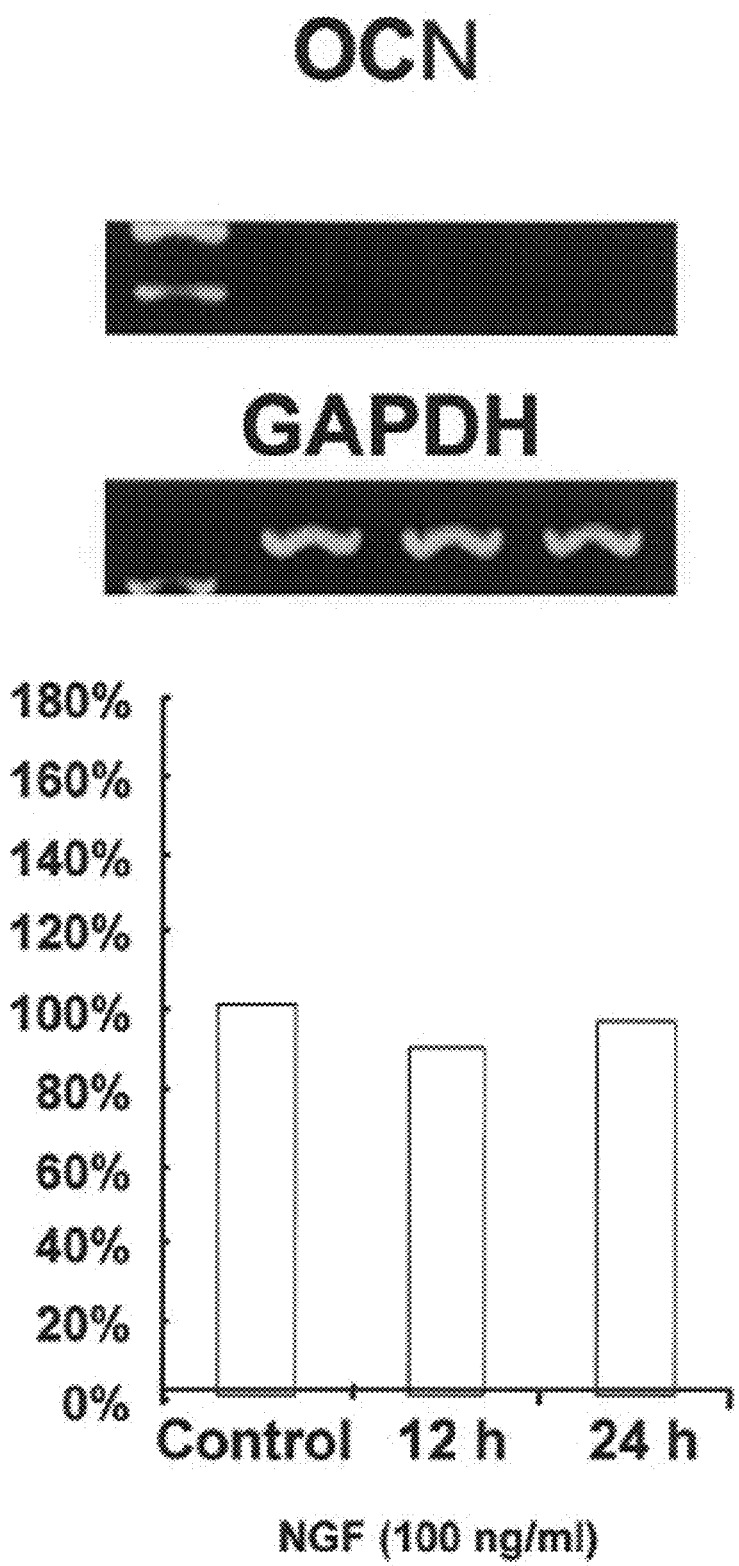
FIG. 25B shows by an electrophoretogram and a bar graph the relationship between the exposure time of NGF and the amount of OCN mRNA expression in HMS cells; it also shows an electrophoretogram depicting the relationship with the amount of GAPDH mRNA expression; HMS cells were all treated with NGF at a final concentration of 100 ng/ml; the lane at the left end of each electrophoretogram is the marker; the vertical axis of the graph plots the percentage of the amount of mRNA expression for each exposure time of NGF, with the amount of mRNA expression for exposure time zero being taken as 100%; the horizontal axis plots the exposure time of NGF.
Figure 25C:
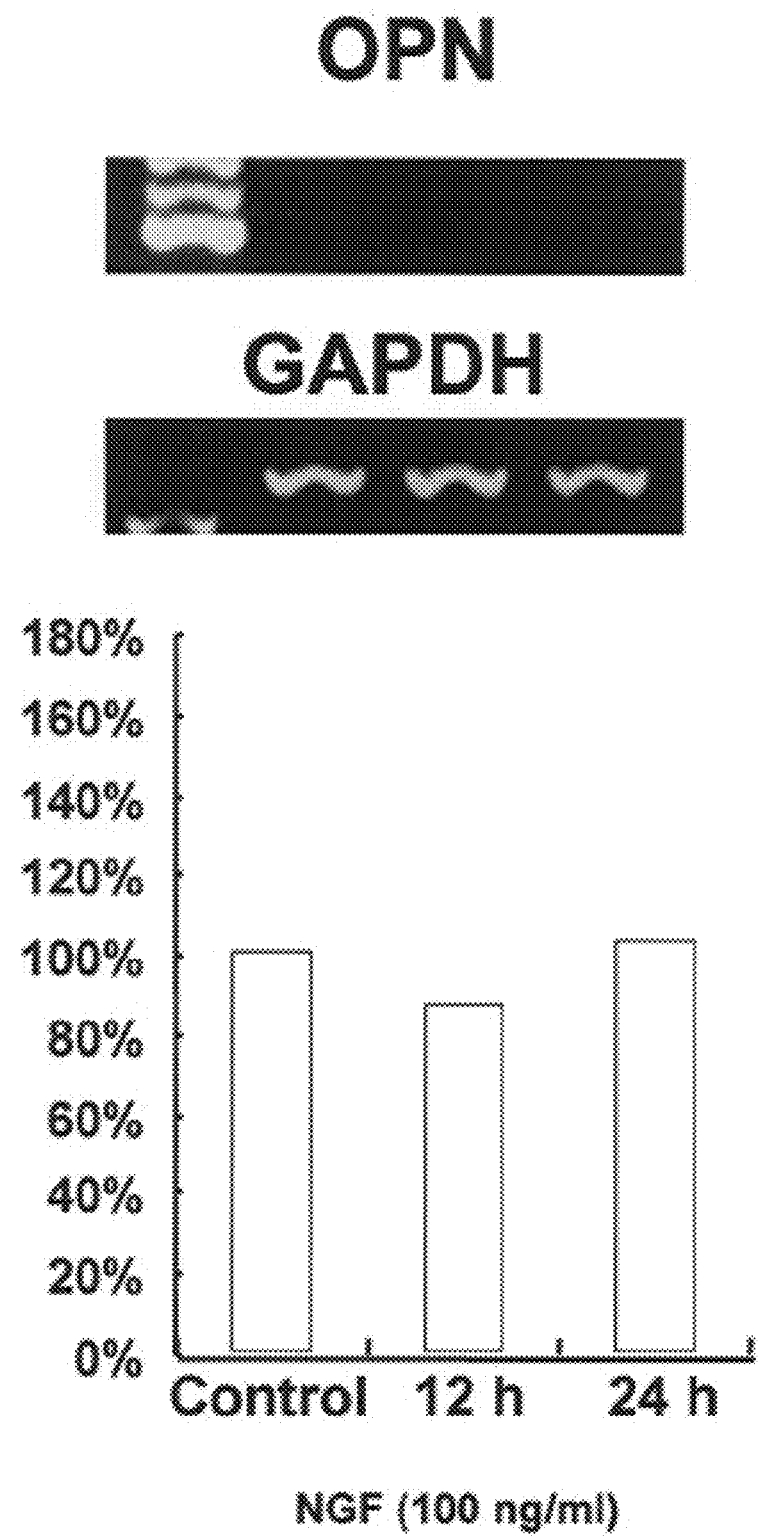
FIG. 25C shows by an electrophoretogram and a bar graph the relationship between the exposure time of NGF and the amount of OPN mRNA expression in HMS cells; it also shows an electrophoretogram depicting the relationship with the amount of GAPDH mRNA expression; HMS cells were all treated with NGF at a final concentration of 100 ng/ml; the lane at the left end of each electrophoretogram is the marker; the vertical axis of the graph plots the percentage of the amount of mRNA expression for each exposure time of NGF, with the amount of mRNA expression for exposure time zero being taken as 100%; the horizontal axis plots the exposure time of NGF.
Figure 25D:
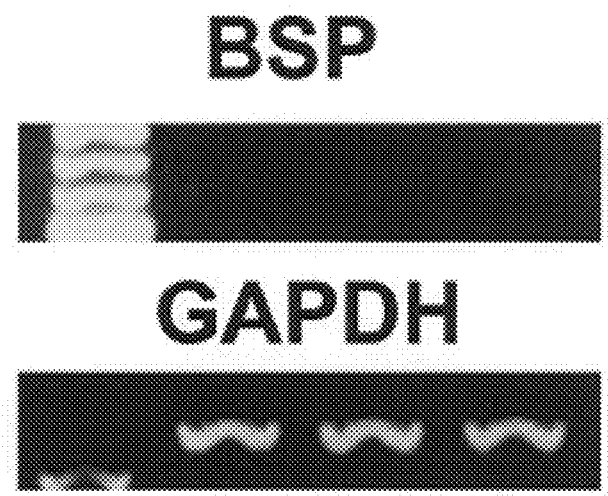
FIG. 25D shows by an electrophoretogram and a bar graph the relationship between the exposure time of NGF and the amount of BSP mRNA expression in HMS cells; it also shows an electrophoretogram depicting the relationship with the amount of GAPDH mRNA expression; HMS cells were all treated with NGF at a final concentration of 100 ng/ml; the lane at the left end of each electrophoretogram is the marker; the vertical axis of the graph plots the percentage of the amount of mRNA expression for each exposure time of NGF, with the amount of mRNA expression for exposure time zero being taken as 100%; the horizontal axis plots the exposure time of NGF.
Figure 25D:
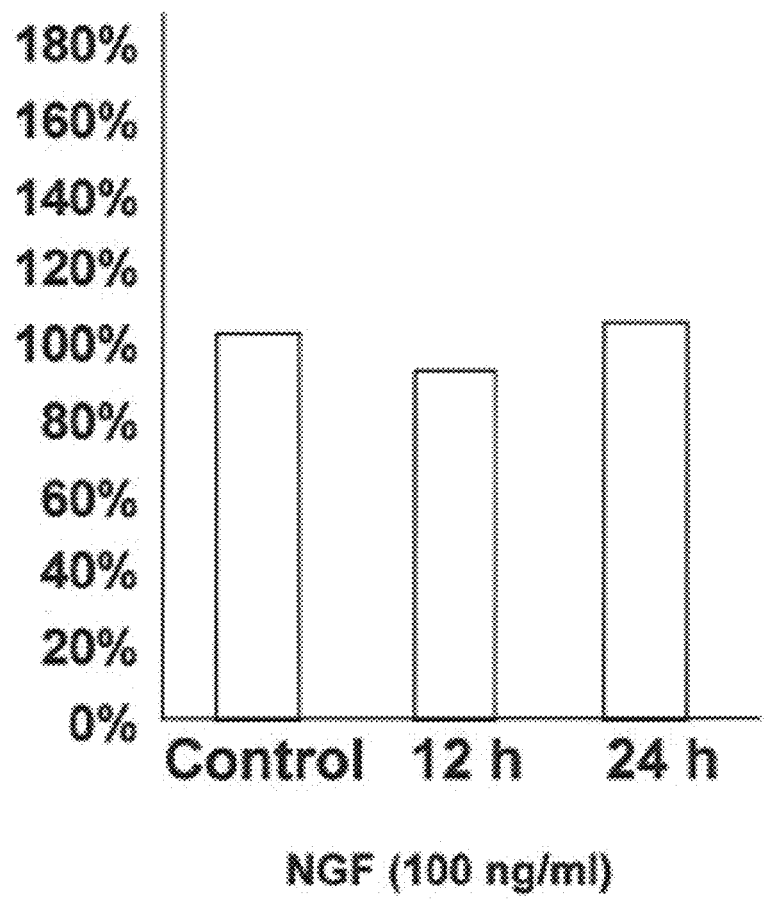
Figure 25E:
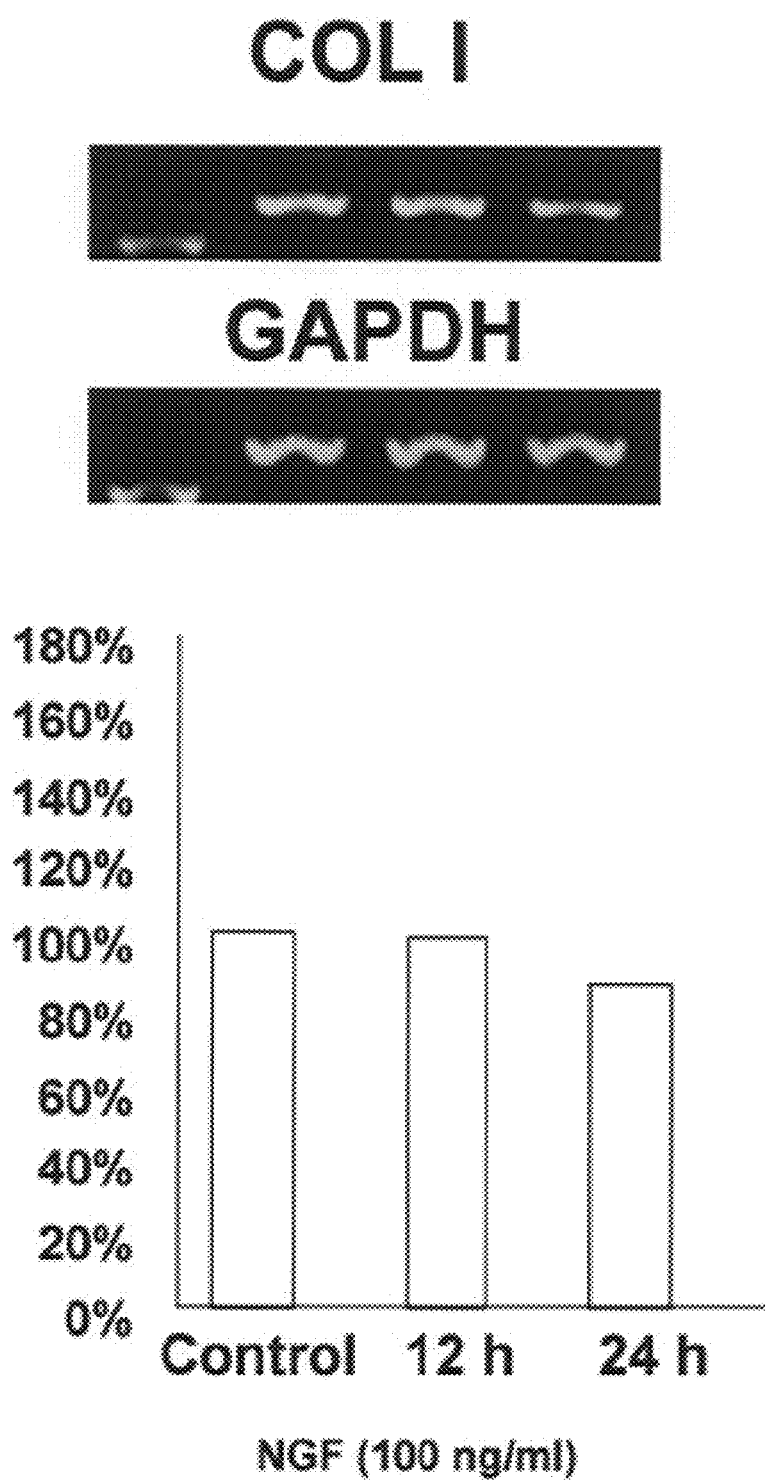
FIG. 25E shows by an electrophoretogram and a bar graph the relationship between the exposure time of NGF and the amount of type I collagen mRNA expression in HMS cells; it also shows an electrophoretogram depicting the relationship with the amount of GAPDH mRNA expression; HMS cells were all treated with NGF at a final concentration of 100 ng/ml; the lane at the left end of each electrophoretogram is the marker; the vertical axis of the graph plots the percentage of the amount of mRNA expression for each exposure time of NGF, with the amount of mRNA expression for exposure time zero being taken as 100%; the horizontal axis plots the exposure time of NGF.
Figure 26A:
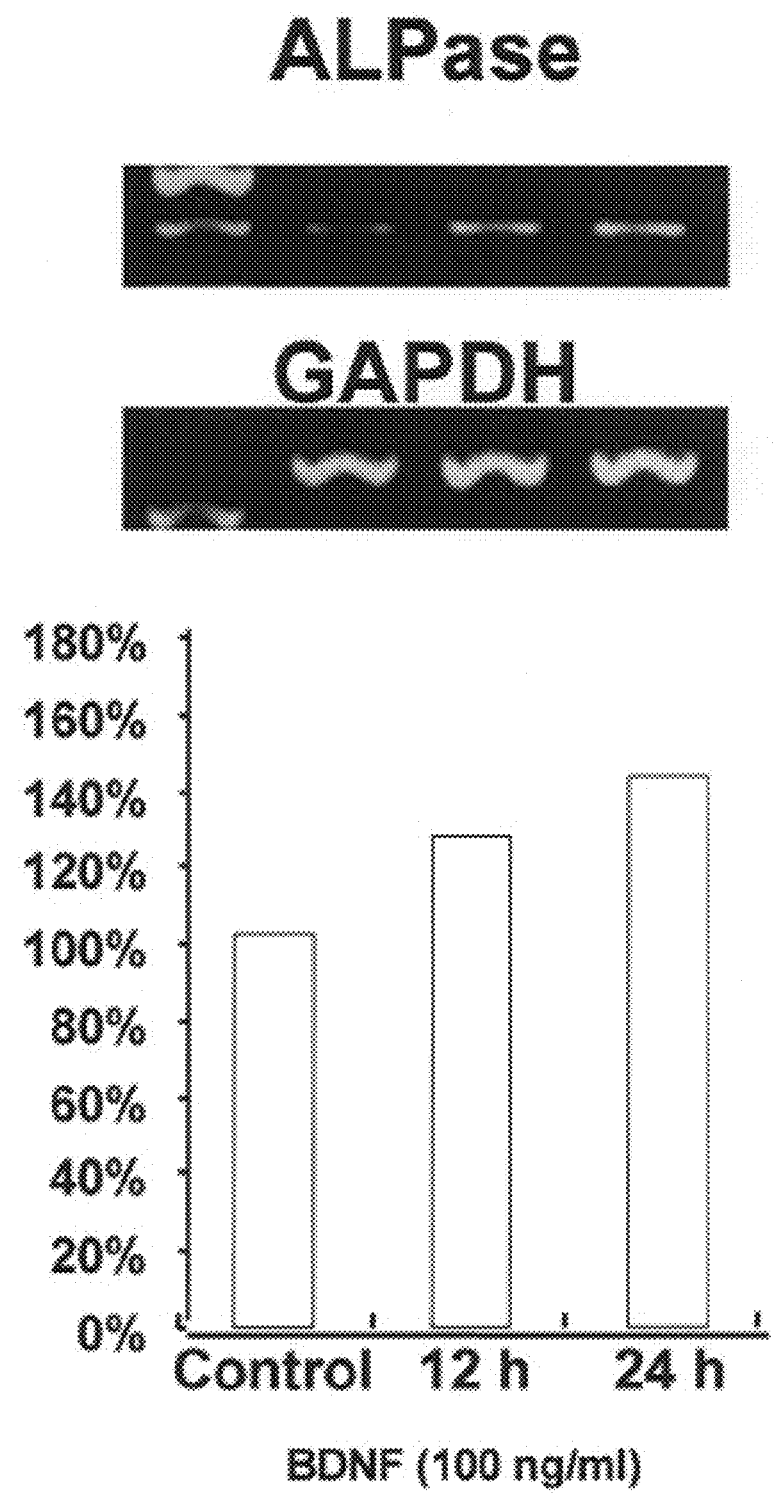
FIG. 26A shows by an electrophoretogram and a bar graph the relationship between the exposure time of BDNF and the amount of ALPase mRNA expression in HMS cells; it also shows an electrophoretogram depicting the relationship with the amount of GAPDH mRNA expression; HMS cells were all treated with BDNF at a final concentration of 100 ng/ml; the lane at the left end of each electrophoretogram is the marker; the vertical axis of the graph plots the percentage of the amount of mRNA expression for each exposure time of BDNF, with the amount of mRNA expression for exposure time zero being taken as 100%; the horizontal axis plots the exposure time of BDNF.
Figure 26B:
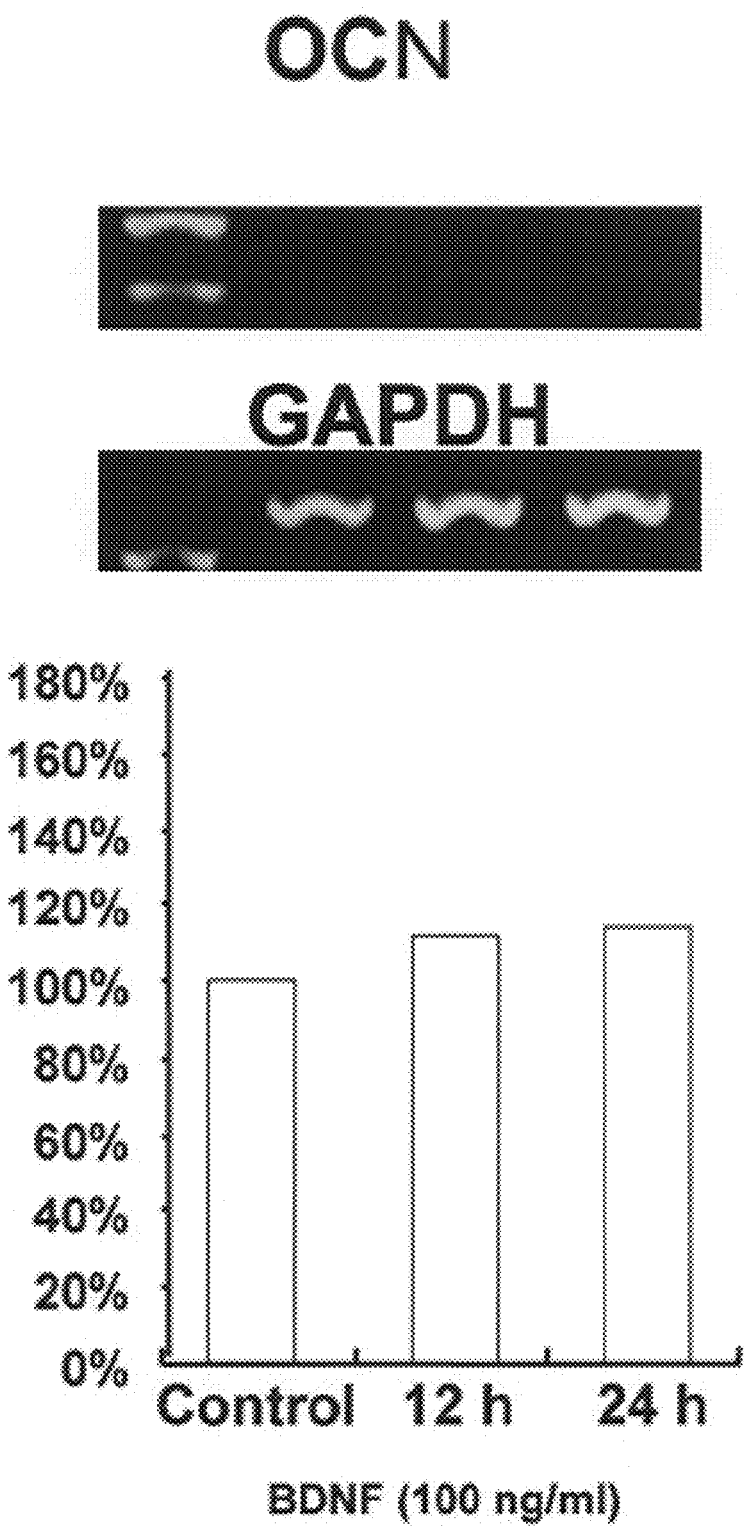
FIG. 26B shows by an electrophoretogram and a bar graph the relationship between the exposure time of BDNF and the amount of OCN mRNA expression in HMS cells; it also shows an electrophoretogram depicting the relationship with the amount of GAPDH mRNA expression; HMS cells were all treated with BDNF at a final concentration of 100 ng/ml; the lane at the left end of each electrophoretogram is the marker; the vertical axis of the graph plots the percentage of the amount of mRNA expression for each exposure time of BDNF, with the amount of mRNA expression for exposure time zero being taken as 100%; the horizontal axis plots the exposure time of BDNF.
Figure 26C:
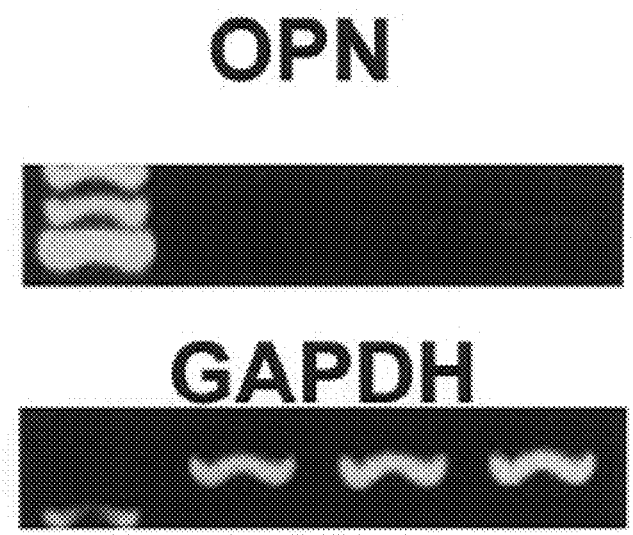
FIG. 26C shows by an electrophoretogram and a bar graph the relationship between the exposure time of BDNF and the amount of OPN mRNA expression in HMS cells; it also shows an electrophoretogram depicting the relationship with the amount of GAPDH mRNA expression; HMS cells were all treated with BDNF at a final concentration of 100 ng/ml; the lane at the left end of each electrophoretogram is the marker; the vertical axis of the graph plots the percentage of the amount of mRNA expression for each exposure time of BDNF, with the amount of mRNA expression for exposure time zero being taken as 100%; the horizontal axis plots the exposure time of BDNF.
Figure 26C:
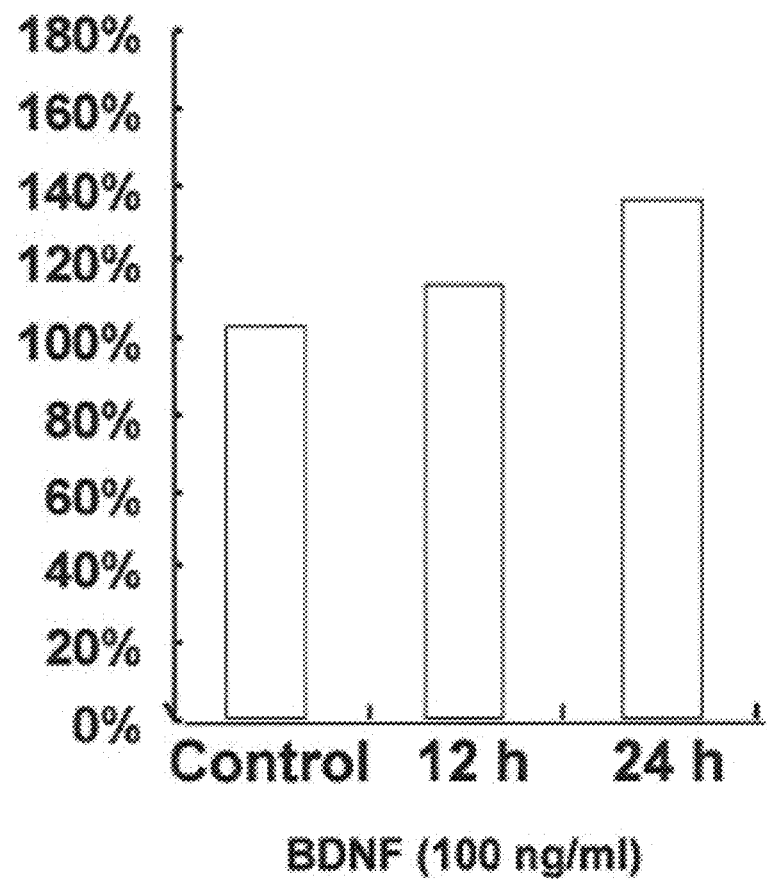
Figure 26D:
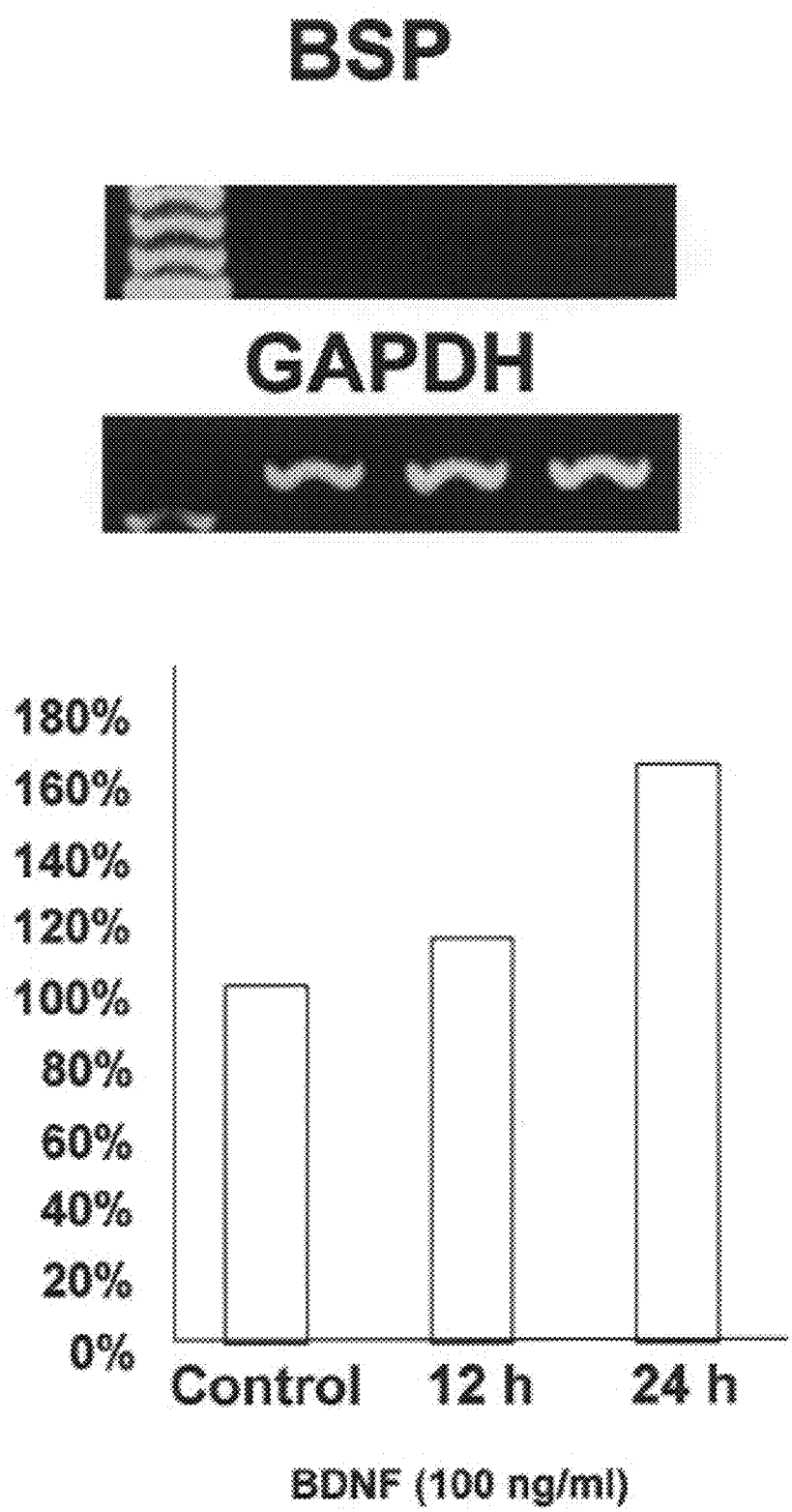
FIG. 26D shows by an electrophoretogram and a bar graph the relationship between the exposure time of BDNF and the amount of BSP mRNA expression in HMS cells; it also shows an electrophoretogram depicting the relationship with the amount of GAPDH mRNA expression; HMS cells were all treated with BDNF at a final concentration of 100 ng/ml; the lane at the left end of each electrophoretogram is the marker; the vertical axis of the graph plots the percentage of the amount of mRNA expression for each exposure time of BDNF, with the amount of mRNA expression for exposure time zero being taken as 100%; the horizontal axis plots the exposure time of BDNF.
Figure 26E:
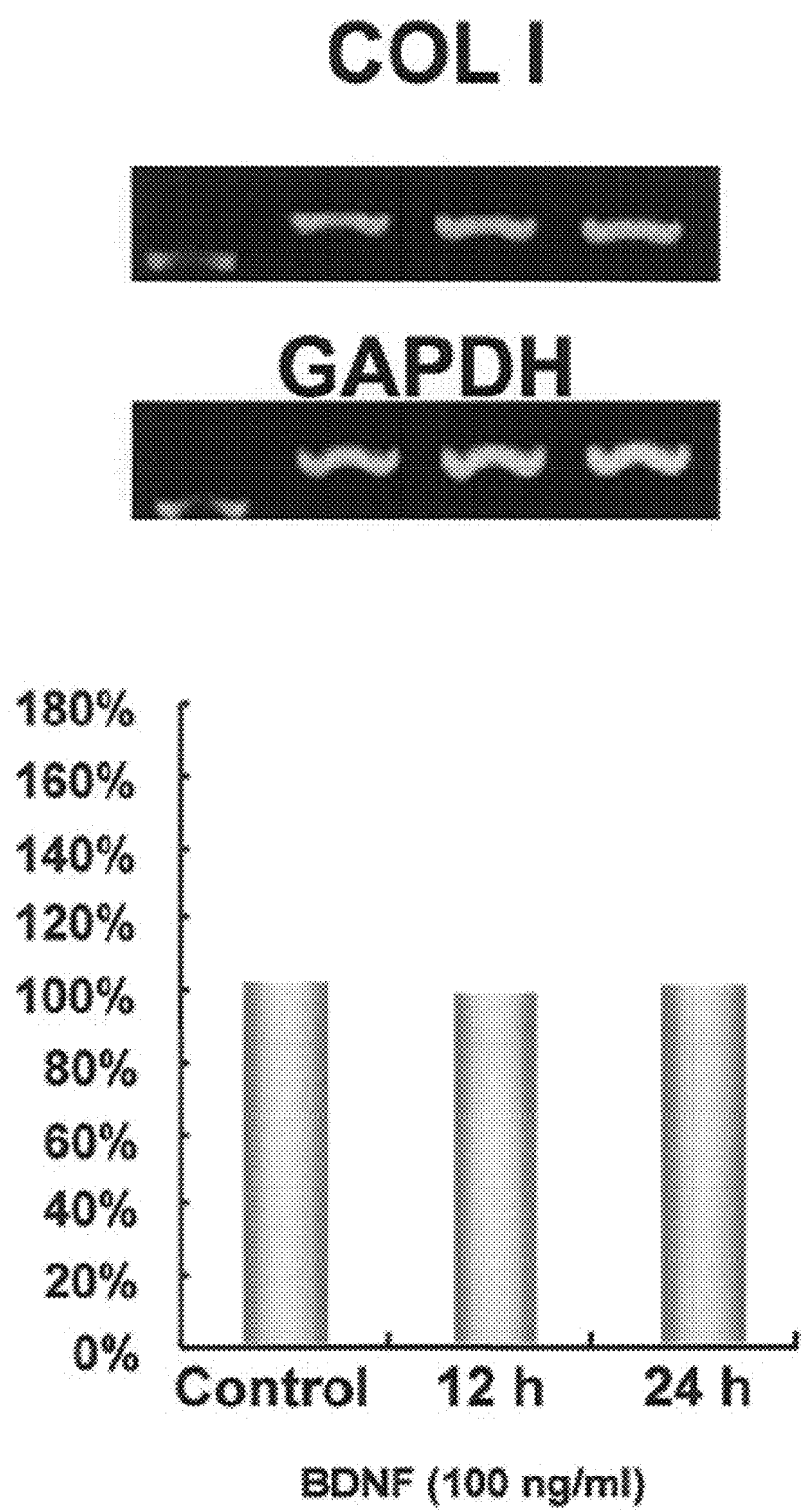
FIG. 26E shows by an electrophoretogram and a bar graph the relationship between the exposure time of BDNF and the amount of type I collagen mRNA expression in HMS cells; it also shows an electrophoretogram depicting the relationship with the amount of GAPDH mRNA expression; HMS cells were all treated with BDNF at a final concentration of 100 ng/ml; the lane at the left end of each electrophoretogram is the marker; the vertical axis of the graph plots the percentage of the amount of mRNA expression for each exposure time of BDNF, with the amount of mRNA expression for exposure time zero being taken as 100%; the horizontal axis plots the exposure time of BDNF.
Figure 27A:
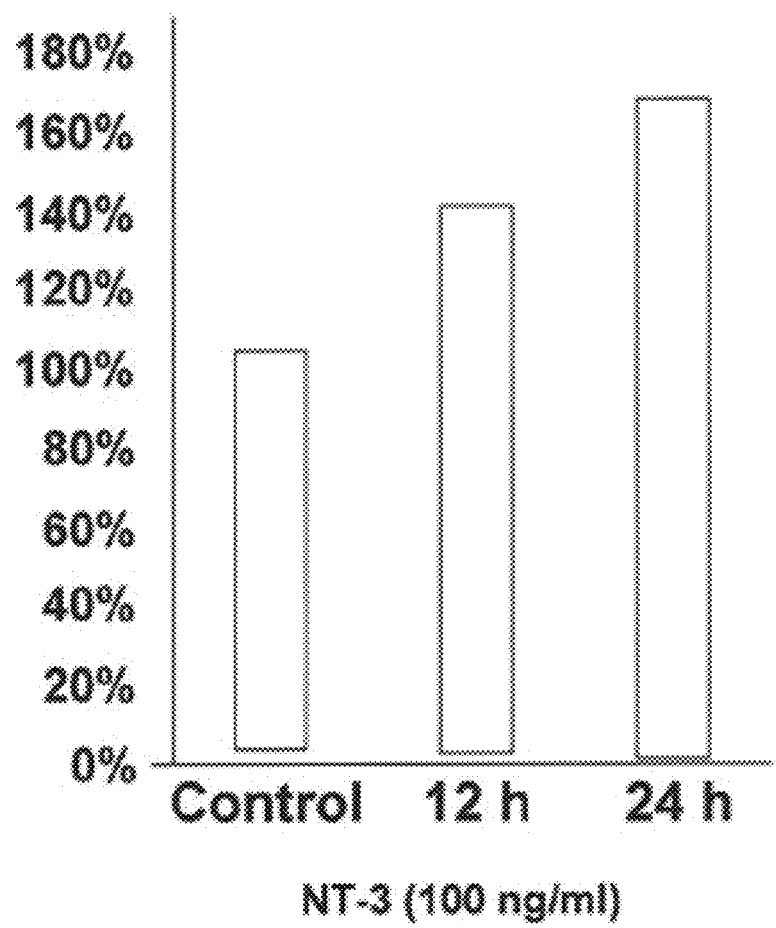
FIG. 27A shows by an electrophoretogram and a bar graph the relationship between the exposure time of NT-3 and the amount of ALPase mRNA expression in HMS cells; it also shows an electrophoretogram depicting the relationship with the amount of GAPDH mRNA expression; HMS cells were all treated with NT-3 at a final concentration of 100 ng/ml; the lane at the left end of each electrophoretogram is the marker; the vertical axis of the graph plots the percentage of the amount of mRNA expression for each exposure time of NT-3, with the amount of mRNA expression for exposure time zero being taken as 100%; the horizontal axis plots the exposure time of NT-3.
Figure 27B:
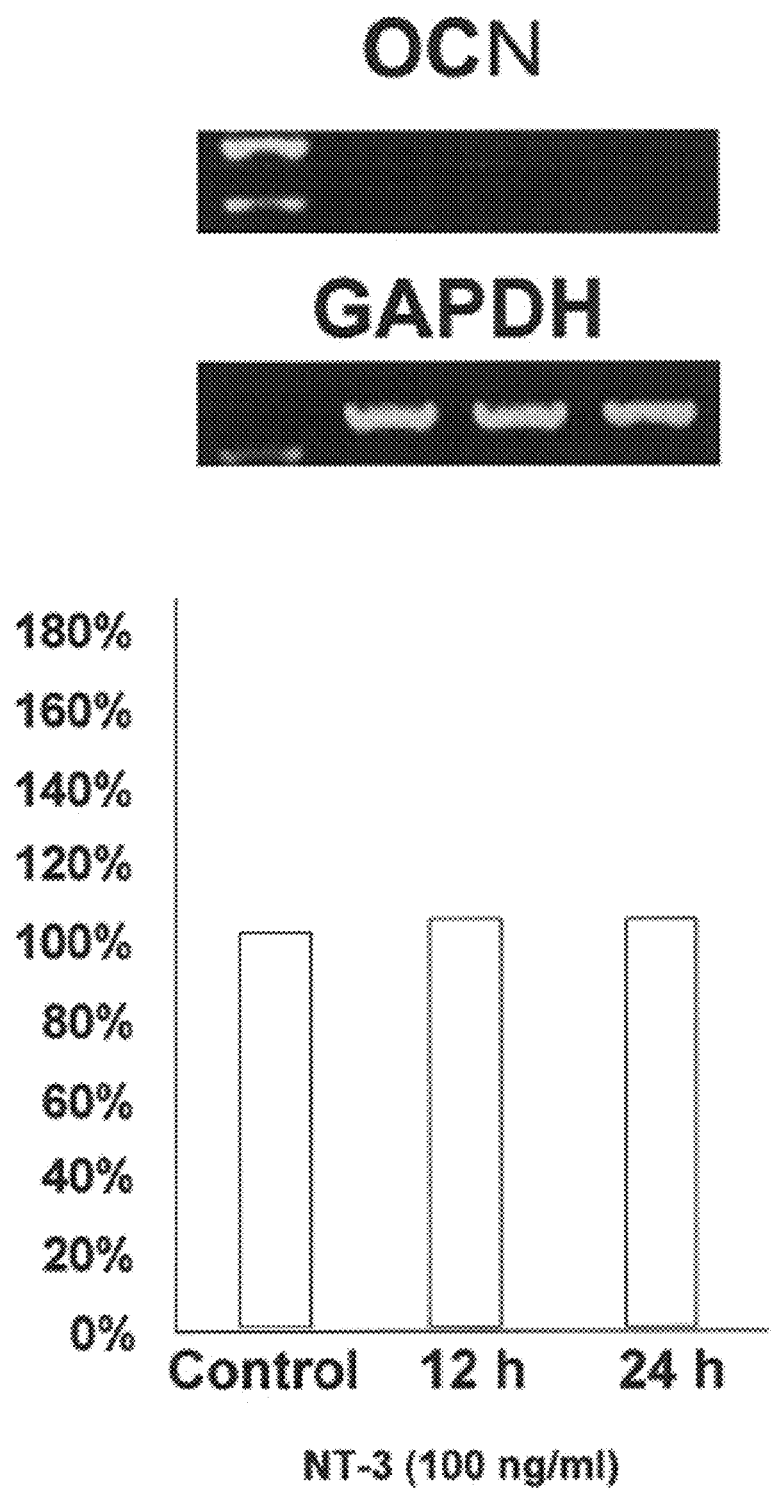
FIG. 27B shows by an electrophoretogram and a bar graph the relationship between the exposure time of NT-3 and the amount of OCN mRNA expression in HMS cells; it also shows an electrophoretogram depicting the relationship with the amount of GAPDH mRNA expression; HMS cells were all treated with NT-3 at a final concentration of 100 ng/ml; the lane at the left end of each electrophoretogram is the marker; the vertical axis of the graph plots the percentage of the amount of mRNA expression for each exposure time of NT-3, with the amount of mRNA expression for exposure time zero being taken as 100%; the horizontal axis plots the exposure time of NT-3.
Figure 27C:
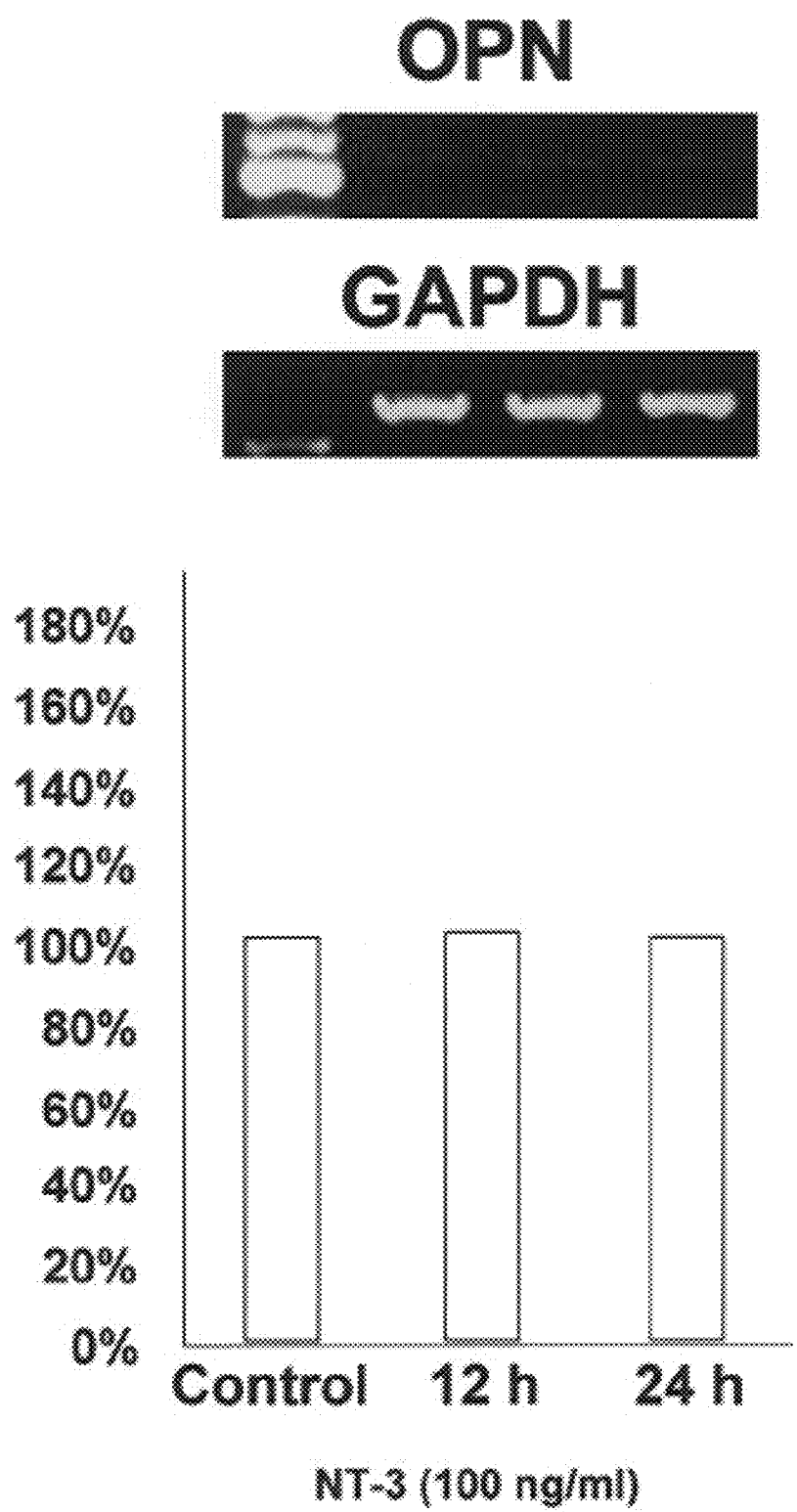
FIG. 27C shows by an electrophoretogram and a bar graph the relationship between the exposure time of NT-3 and the amount of OPN mRNA expression in HMS cells; it also shows an electrophoretogram depicting the relationship with the amount of GAPDH mRNA expression; HMS cells were all treated with NT-3 at a final concentration of 100 ng/ml; the lane at the left end of each electrophoretogram is the marker; the vertical axis of the graph plots the percentage of the amount of mRNA expression for each exposure time of NT-3, with the amount of mRNA expression for exposure time zero being taken as 100%; the horizontal axis plots the exposure time of NT-3.
Figure 27D:
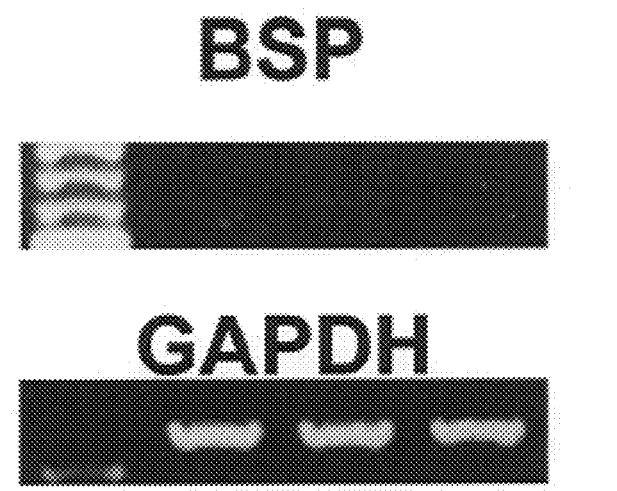
FIG. 27D shows by an electrophoretogram and a bar graph the relationship between the exposure time of NT-3 and the amount of BSP mRNA expression in HMS cells; it also shows an electrophoretogram depicting the relationship with the amount of GAPDH mRNA expression; HMS cells were all treated with NT-3 at a final concentration of 100 ng/ml; the lane at the left end of each electrophoretogram is the marker; the vertical axis of the graph plots the percentage of the amount of mRNA expression for each exposure time of NT-3, with the amount of mRNA expression for exposure time zero being taken as 100%; the horizontal axis plots the exposure time of NT-3.
Figure 27D:
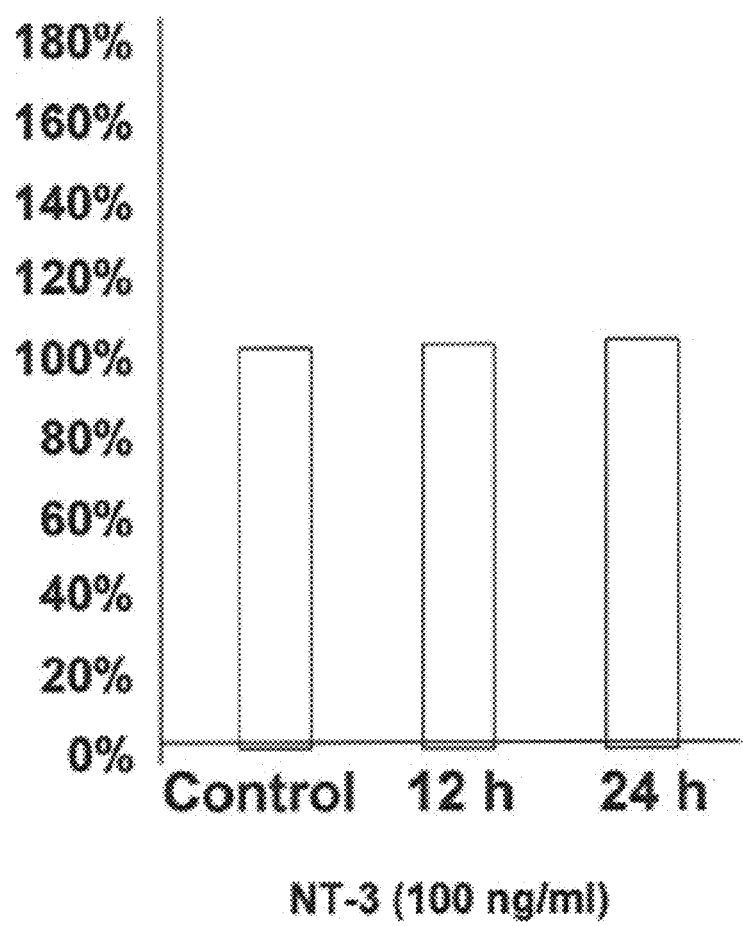
Figure 27E:
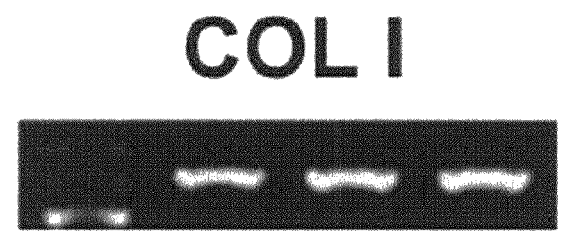
FIG. 27E shows by an electrophoretogram and a bar graph the relationship between the exposure time of NT-3 and the amount of type I collagen mRNA expression in HMS cells; it also shows an electrophoretogram depicting the relationship with the amount of GAPDH mRNA expression; HMS cells were all treated with NT-3 at a final concentration of 100 ng/ml; the lane at the left end of each electrophoretogram is the marker; the vertical axis of the graph plots the percentage of the amount of mRNA expression for each exposure time of NT-3, with the amount of mRNA expression for exposure time zero being taken as 100%; the horizontal axis plots the exposure time of NT-3.
Figure 27E:
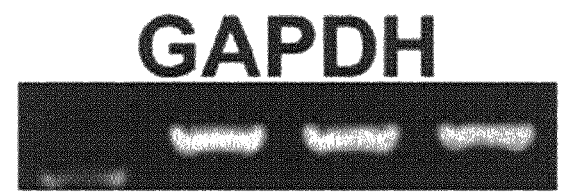
Figure 27E:
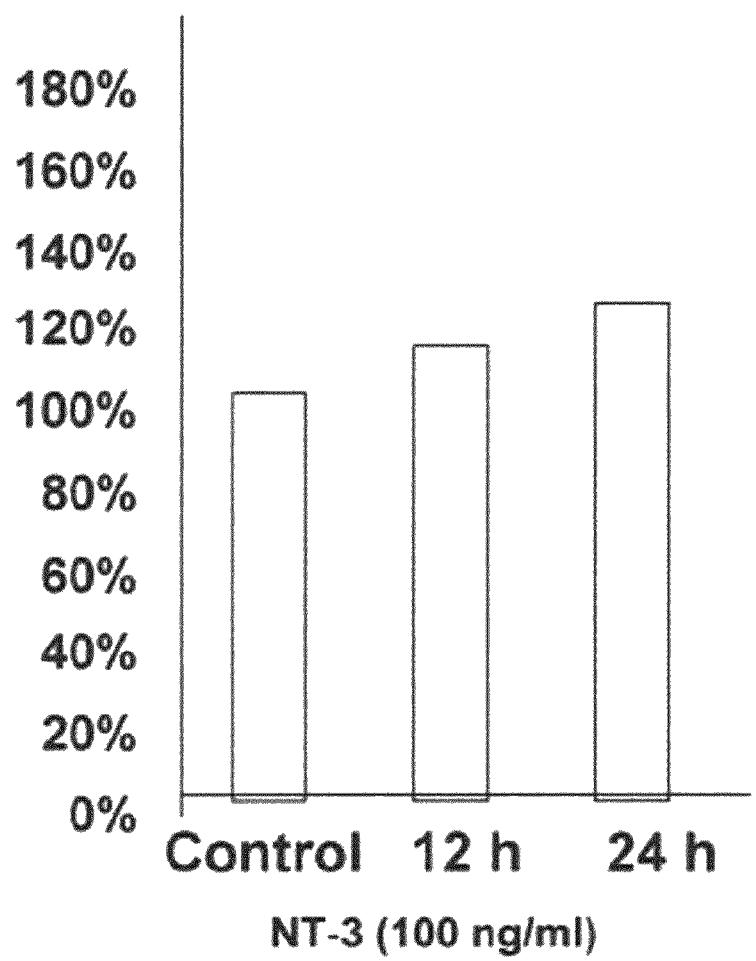

The results are shown in FIG. 24, from which it is clear that NGF, BDNF, NT-3 and NT-4/5 enhanced the DNA synthesizing ability of HP cells.

Example 7

The effects of NGF, BDNF, NT-3 and ascorbic acid on human mesenchymal stem cells (HMS cells) were investigated.

(1) Cells Used

HMS cells were separated in accordance with the method of Tsutsumi et al. (S. Tsutsumi: BBRC, 26, 288(2), 2001). To be specific, when a wisdom tooth was removed from patients who gave a fully informed consent to the experiment, the mandibular bone was punctured to aspirate bone marrow. The bone marrow was immediately mixed with Dulbecco's modified Eagle's medium (DMEM, Sigma, USA) supplemented with heparin sodium (200 U/ml, Sigma, USA) and the mixture was centrifuged (150 g, 5 min). After the centrifugation, the supernatant was removed and the resulting cell component was suspended in DMEM containing 10% fetal calf serum (FCS, Biological Industries, Israel), 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA) and the suspension was seeded on cell culture Petri dishes of 100 mm diameter (Corning, USA) such that the bone marrow was at 200-500 µl/dish and the medium was at 10 ml/dish. Culture was performed at 37° C. in a 5% $CO_2$ gas phase. Subsequently, medium change was done every four days. Just before the proliferating cells had reached confluence, phosphate buffered physiological saline (PBS, NISSUI PHARMACEUTICAL CO., LTD., Tokyo) containing 0.05% trypsin (Difco, USA), 0.02% EDTA (KATAYAMA CHEMICAL INDUSTRIES Co., Ltd., Osaka), 100 units/ml of penicillin and 100 µg/ml of streptomycin was used to disperse the cells. The cells thus dispersed were suspended in DMEM supplemented with 20% FCS, 10% dimethyl sulfoxide (DMSO, KATAYAMA CHEMICAL INDUSTRIES Co., Ltd., Osaka), 100 units/ml of penicillin and 100 µg/ml of streptomycin; the suspended cell density was $1.0 \times 10^6$ cells/ml; the suspension was distributed in 1-ml portions among serum tubes (SUMITOMO BAKELITE COMPANY LIMITED, Tokyo), cooled at −20° C. for 2 hours, then at −80° C. overnight before storage in liquid nitrogen.

(2) Expression of mRNA for Bone-Related Proteins in HMS Cells (i) Treatment of Cells with NGF, BDNF and NT-3

The HMS cells obtained in (1) above were suspended in 10% FCS containing DMEM (supplemented with 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA)) and the suspension was seeded on a 6-well cell culture plate at a density of $1.0 \times 10^5$ cells/well. The cells were cultivated for a week and just before they had reached confluence, the medium was changed for FCS-free DMEM (supplemented with 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA)) and either one of NGF, BDNF and NT-3 was allowed to act for 12 or 24 hours at a concentration of 100 ng/ml. After the end of culture, total RNA was extracted using ISOGEN (trade name).

(ii) Expression of mRNA

PCR was performed using primers specific to ALPase, OCN, OPN, bone sialoprotein (BSP) and type I collagen. The PCR consisted of denaturation at 94° C. for 2 minutes, 30 cycles of 94° C.×15 seconds, annealing for 30 seconds and 72° C.×50 seconds (but 35 cycles in the case of BSP), followed by extension at 72° C. for 7 minutes. The PCR products obtained were electrophoresed on a 2% agarose gel containing 0.002% ethidium bromide. The density of the bands after electrophoresis was measured using NIH image.

The results are shown in FIGS. 25A-25E, 26A-26E and 27A-27E. As is clear from the Figures, NGF had no marked effect on the expression of mRNA for any of ALPase, OCN, OPN, BSP and type I collagen in HMS cells. BDNF highly enhanced the expression of mRNA for ALPase, OPN, BSP and BMP-2 while enhancing the expression of the OCN gene to some extent. NT-3 enhanced the expression of mRNA for ALPase and type I collagen.

(3) The Effects of Ascorbic Acid, NGF, BDNF and NT-3 on the Proliferation of HMS Cells The HMS cells obtained in (1) above were suspended in 10% FCS containing DMEM (product of NISSUI PHARMACEUTICAL CO., LTD.; supplemented with 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA)) and the suspension was seeded on a 96-well cell culture plate (Corning, USA) at a density of $5.0 \times 10^3$ cells/well. In the test groups, 50 µg/ml of ascorbic acid (Sigma, USA) or 100 ng/ml of NGF (FUNAKOSHI, Tokyo) or 100 ng/ml of BDNF (FUNAKOSHI, Tokyo) or 100 ng/ml of NT-3 (FUNAKOSHI, Tokyo) was singly added to the culture medium 24 hours after the start of culture, and cultivation was continued for 7 more days. Medium change was done on day 4. The control group was cultivated on 10% FCS containing DMEM (product of NISSUI PHARMACEUTICAL CO., LTD.; supplemented with 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA)). After 7 days of culture, the mediums were entirely changed for 10% FCS containing DMEM (supplemented with 100 units/ml of penicillin (MEIJI SEIKA KAISHA, LTD., Tokyo), 100 µg/ml of streptomycin (MEIJI SEIKA KAISHA, LTD., Tokyo) and 1 µg/ml of amphotericin B (GIBCO, USA)) and the number of viable cells was counted by absorbance measurement at 490 nm with CellTiter 96 (trade name) AQueous One Solution Cell Proliferation Assay Kit (Promega, USA).

Figure 28:
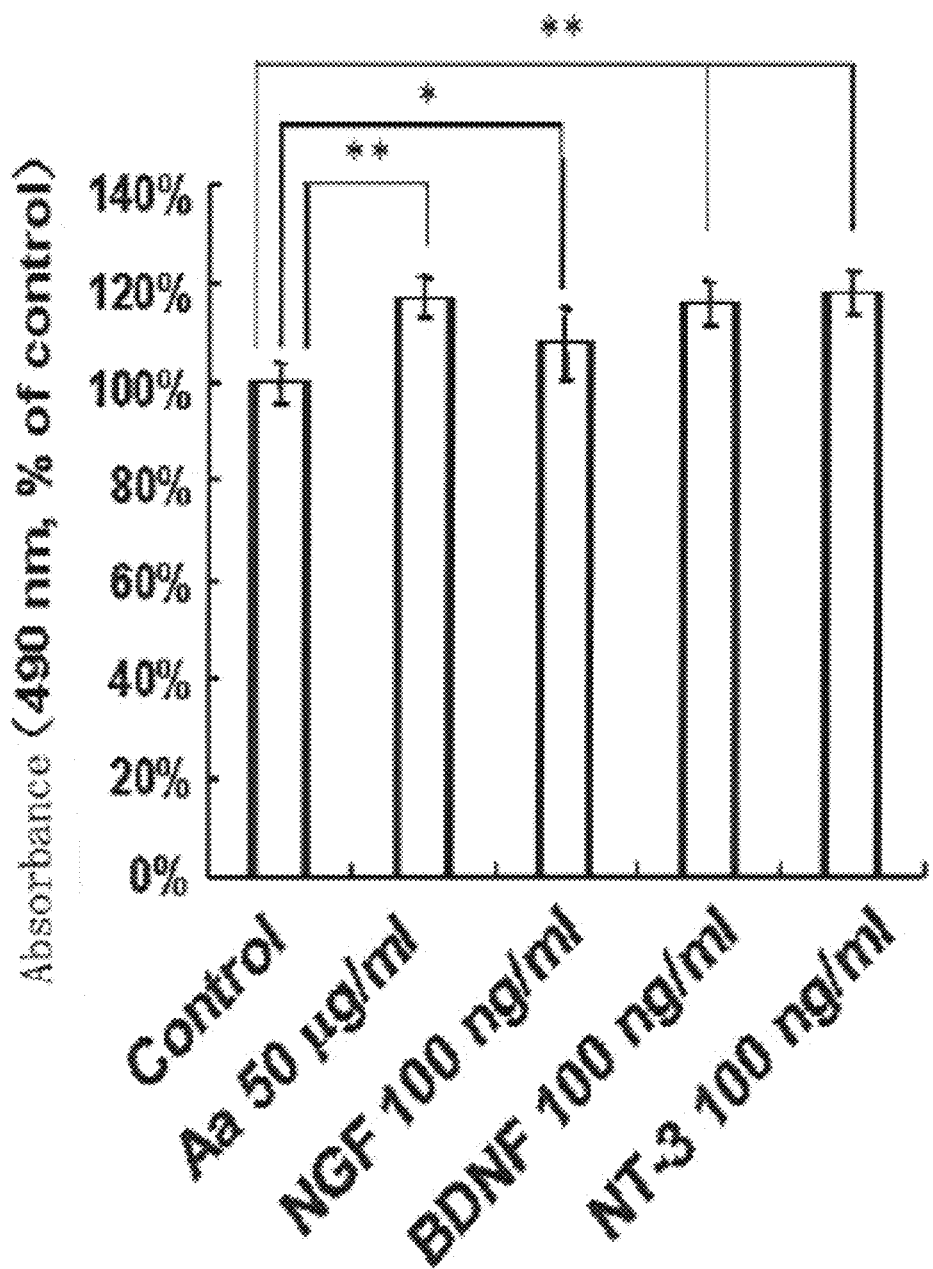
FIG. 28 is a bar graph showing the effects of ascorbic acid (Aa), NGF, BDNF and NT-3 on the proliferation of HMS cells; the vertical axis of the graph plots the percentage of the absorbance of each test group as relative to the control group; the vertical lines on the bars in the graph represent the range of mean±standard deviation; * and ** mean p<0.05 and p<0.01, respectively (statistical testing by t-test).

The results are shown in FIG. 28. The vertical axis of the graph plots the percentage of the absorbance in the test groups as against the control group. In the graph, * and ** mean $p<0.05$ and $p<0.01$, respectively (statistical testing by t-test). As is clear from the Figure, the HMS cells cultivated on the medium supplemented with either one of ascorbic acid, NGF, BDNF and NT-3 showed a significantly higher tendency to proliferate than the control. In particular, the proliferation enhancing effect of ascorbic acid, BDNF and NT-3 was stronger than that of NGF.

Example 8

The effects of NGF and NT-3 on beagle dogs as models of class III furcation defect were investigated.

Experiments were conducted as in Example 2, except that TERUPLUG® of 8 mm diameter×5 mm impregnated with 25 µl of a NGF solution (in sterile physiological saline) at a concentration of 100 µg/ml instead of the BDNF solutions (in sterile physiological saline) at concentrations of 5, 25 and 50 µg/ml, as well as TERUPLUG® of the same size which was impregnated with 25 µl of a NT-3 solution (in sterile physiological saline) at a concentration of 100 µg/ml were used as transplants. Among the tissue specimens prepared (and hematoxylin-eosin stained), those which were cut in the mesial-distal plane through the buccal-lingual extension of the tooth and which had been cut near the midroot were chosen and examined under an optical microscope (ECLIPSE E600, NIKON).

Figure 29A:
FIG. 29A is an optical microscopic view (×20) of a bone defect at furcation which was packed with a transplant containing NGF (100 μg/ml), prepared in Example 8.
Figure 29B:
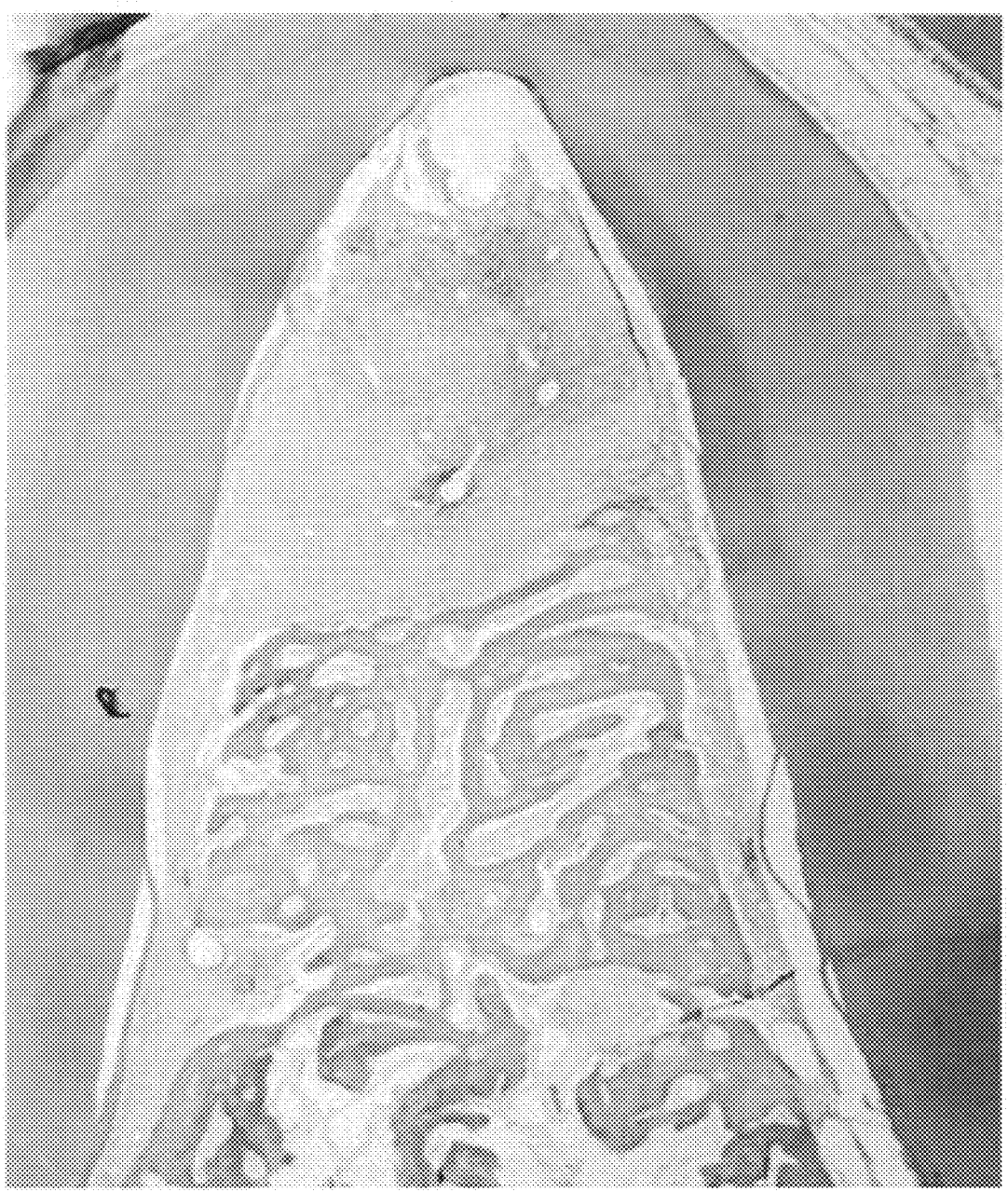
FIG. 29B is a microscopic view (×20) of a bone defect at furcation which was packed with a transplant containing NT-3 (100 μg/ml), prepared in Example 8.

FIG. 29A is an optical microscopic view of the bone defect at furcation packed with the NGF containing transplant, and FIG. 29B is an optical microscopic view (×20) of the bone defect at furcation packed with the NT-3 containing transplant. As is clear from the microphotographs, regenerated bone was observed in the dog models of class III furcation defect in response to the administration of NGF or NT-3.

INDUSTRIAL APPLICABILITY

The therapeutic agent for periodontal diseases, the repaired dentin morphogenesis enhancer, the therapeutic method, the transplant for periodontal tissue regeneration, and the method for regenerating the periodontal tissue according to the present invention have a potential to become effective in the treatment of periodontal diseases and endodontic therapy.

The invention claimed is:

1. A method for treatment of periodontal disease which comprises administering a transplant comprising:
   a therapeutically effective amount, per tooth or defect, of a neurotrophic factor for regenerating periodontal tissues, and
   a sheet or sponge impregnated with the neurotrophic factor, comprising a biodegradable protein material and a tissue absorbing material,
to a subject who is suffering or prone to suffer from the disease in order to regenerate periodontal tissues, wherein the neurotrophic factor is a brain-derived neurotrophic factor or neurotrophin-4/5, wherein the therapeutically effective amount is in the range of $1\times10^{-12}$ g to $1\times10^{-3}$ g per tooth or defect, and wherein the biodegradable protein material is selected from the group consisting of collagen, gelatin, albumin, and platelet-rich plasma (PRP), and the tissue absorbing material is selected from the group consisting of hyaluronic acid (HA) and tricalcium phosphate (TCP).

2. The method according to claim 1 which regenerates cementum.

3. The method according to claim 1 which regenerates periodontal ligament.

4. The method according to claim 1 which regenerates alveolar bone.

5. The method according to claim 1 which regenerates dental pulp.

6. The method according to claim 1 which reduces or inhibits the apical invasion of gingival epithelium along the dental root surface.

7. The method according to claim 1 which enhances production of repaired dentin in the pulp cavity.

8. The method according to claim 1 which enhances addition of repaired dentin to the inner surfaces of the pulp cavity.

* * * * *